(12) United States Patent
Braunschweig et al.

(10) Patent No.: US 9,296,688 B2
(45) Date of Patent: Mar. 29, 2016

(54) CARBOHYDRATE-SELECTIVE RECEPTORS

(71) Applicants: Adam B. Braunschweig, New York, NY (US); Stephen Rieth, New York, NY (US); Matthew Miner, Sunnyside, NY (US)

(72) Inventors: Adam B. Braunschweig, New York, NY (US); Stephen Rieth, New York, NY (US); Matthew Miner, Sunnyside, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/403,686

(22) PCT Filed: May 28, 2013

(86) PCT No.: PCT/US2013/042888
§ 371 (c)(1),
(2) Date: Nov. 25, 2014

(87) PCT Pub. No.: WO2014/031204
PCT Pub. Date: Feb. 27, 2014

(65) Prior Publication Data
US 2015/0141480 A1    May 21, 2015

Related U.S. Application Data

(60) Provisional application No. 61/708,893, filed on Oct. 2, 2012, provisional application No. 61/652,011, filed on May 25, 2012.

(51) Int. Cl.
| | |
|---|---|
| C07D 207/335 | (2006.01) |
| C07D 403/14 | (2006.01) |
| G01N 24/12 | (2006.01) |
| A61K 31/4025 | (2006.01) |
| G01N 33/53 | (2006.01) |

(52) U.S. Cl.
CPC ........ *C07D 207/335* (2013.01); *A61K 31/4025* (2013.01); *C07D 403/14* (2013.01); *G01N 24/12* (2013.01); *G01N 33/5308* (2013.01); *G01N 2400/00* (2013.01)

(58) Field of Classification Search
CPC ............. C07D 207/335; C07D 403/14; G01N 33/5308; G01N 24/12; A61K 31/4025
See application file for complete search history.

(56) References Cited

PUBLICATIONS

Mazik, Monika, "Molecular Recognition of Carbohydrates by Acyclic Receptors Employing Noncovalent Interactions," Chemical Society Reviews 38:935-956 (2009).
Davis, Anthony P., "Synthetic Lectins," Organic & Biomolecular Chemistry 7:3629-3638 (2009).
Walker et al., "Progress in Biomimetic Carbohydrate Recognition," Cellular and Molecular Life Sciences 66:3177-3191 (2009).
Nativi et al., "Pyrrolic Tripodal Receptors Effectively Recognizing Monosaccharides. Affinity Assessment Through a Generalized Binding Descriptor," J. Am. Chem. Soc. 129:4377-4385 (2007).
Nativi et al., "A beta-Mannoside-Selective Pyrrolic Tripodal Receptor," Organic Letters 9(23):4685-4688 (2007).
Rieth et al., "Saccharide Receptor Achieves Concentration Dependent Mannoside Selectivity Through Two Distinct Cooperative Binding Pathways," Chemical Science 4:357-367 (2013).
PCT International Search Report and Written Opinion for PCT/US2013/042888, filed May 28, 2013 (mailed Mar. 25, 2014).
Jin et al., "Carbohydrate Recognition by Boronolectins, Small Molecules, and Lectins," Med. Res. Rev. 30(2):171-257 (2010).

*Primary Examiner* — Robert Havlin
(74) *Attorney, Agent, or Firm* — LeClairRyan, a Professional Corporation

(57) ABSTRACT

The present invention is directed to a new class of synthetic carbohydrate receptor compounds comprising Formula I as described herein: (I). Other aspects of the present invention relate to pharmaceutical compositions and pharmaceutical delivery vehicles comprising the compound of Formula (I) The present invention is also directed to methods of treatment and diagnosis that involve the administration of a compound of Formula (I).

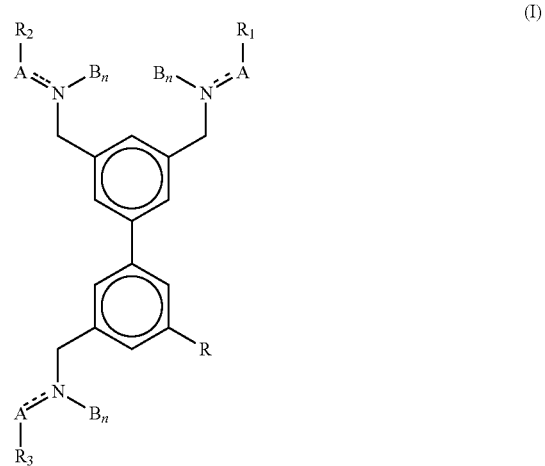

(I)

15 Claims, 56 Drawing Sheets

A.
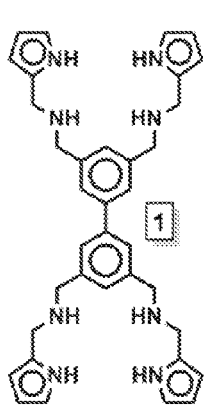
B.
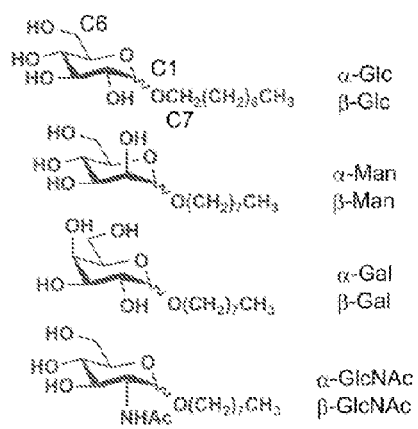
FIGURES 1A-1B
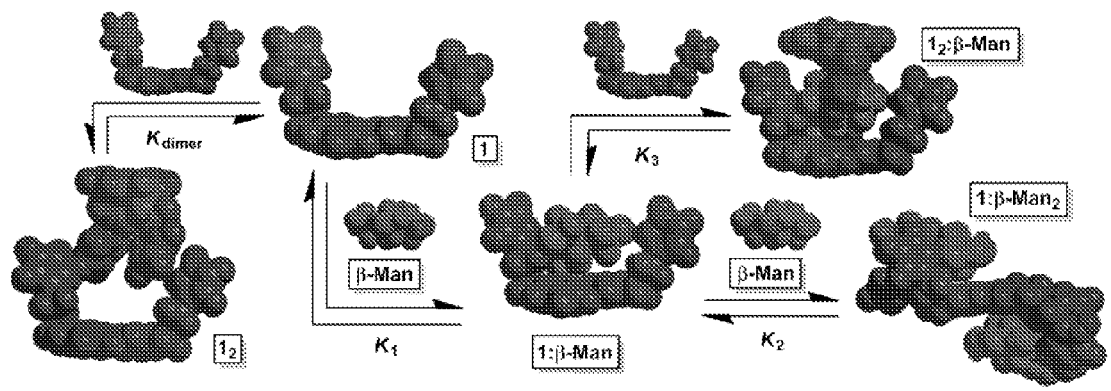
FIGURE 2

Determination of $K_1$ and $K_2$

A

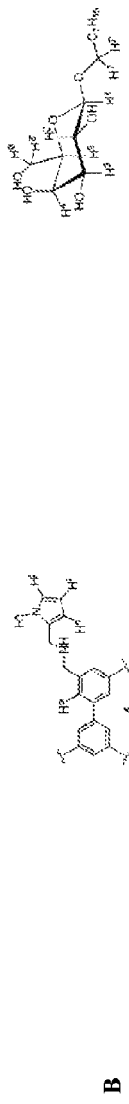

$^1$H NMR (600 MHz, 25°C) chemical shifts (ppm) of a 60 μM solution of 1 [H] in CDCl$_3$ upon incremental addition of β-Glc [G].

| Concentration | | | | | | |
|---|---|---|---|---|---|---|
| [H] mol L$^{-1}$ | [G] mol L$^{-1}$ | k H | a H | j H | i H | h H |
| 0.000058266 | 0 | 8.4821 | 7.4227 | 6.7435 | 6.1459 | 6.0532 |
| 5.71431E-05 | 0.000289725 | 8.5572 | 7.4234 | 6.7448 | 6.1438 | 6.0557 |
| 5.60442E-05 | 0.000663308 | 8.6551 | N/A | 6.7422 | 6.1354 | 6.0558 |
| 5.49860E-05 | 0.000836077 | 8.722 | N/A | 6.7434 | 6.1333 | 6.0591 |
| 5.39685E-05 | 0.001094519 | N/A | N/A | 6.7434 | 6.1296 | 6.0602 |
| 5.29873E-05 | 0.001343273 | N/A | N/A | 6.7463 | 6.1306 | 6.0639 |
| 5.06635E-05 | 0.001927304 | N/A | N/A | 6.7492 | 6.1278 | 6.0692 |
| 4.85717E-05 | 0.002462667 | N/A | N/A | 6.7548 | 6.1291 | N/A |

B

$^1$H NMR (600 MHz, 25°C) chemical shifts (ppm) of a 50 μM solution of 1 [H] in CDCl$_3$ upon incremental addition of β-Gal [G].

| Concentration | | | | | | |
|---|---|---|---|---|---|---|
| [H] mol L$^{-1}$ | [G] mol L$^{-1}$ | k H | a H | j H | i H | h H |
| 0.000047718 | 0 | 8.5082 | 7.4253 | 6.745 | 6.145 | 6.0537 |
| 4.67824E-05 | 0.000288324 | 8.5108 | N/A | 6.7443 | 6.1436 | 6.0541 |
| 4.58827E-05 | 0.000550538 | 8.5406 | N/A | 6.7443 | 6.1425 | 6.0539 |
| 4.5017E-05 | 0.000833774 | N/A | N/A | 6.7435 | 6.1414 | 6.0548 |
| 4.41836E-05 | 0.001091111 | 8.5671 | N/A | 6.7446 | 6.1413 | 6.0543 |
| 0.00004336 | 0.001339091 | 8.5702 | N/A | 6.7446 | 6.1368 | 6.0538 |
| 4.14936E-05 | 0.001921304 | N/A | N/A | 6.7455 | 6.1362 | 6.0582 |
| 0.000039765 | 0.002455 | N/A | N/A | 6.7521 | 6.1337 | 6.0557 |

N/A-Peak could not be resolved

FIGURES 15A-15B

C $^1$H NMR (600 MHz, 25° C) chemical shifts (ppm) of a 60 μM solution of 1 [H] in CDCl$_3$ upon incremental addition of β-GlcNAc [G].

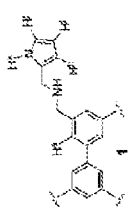

| Concentration | | k | j | a | i | h |
|---|---|---|---|---|---|---|
| [H] mol L$^{-1}$ | [G] mol L$^{-1}$ | H | H | H | H | H |
| 6.000058266 | 0 | 8.64 | 6.7488 | 7.548 | 6.141 | 6.0556 |
| 5.71431E-05 | 0.000254843 | 8.648 | 6.7482 | 7.73 | 6.1407 | 6.0575 |
| 5.60442E-05 | 0.000499035 | 8.663 | 8.749 | 7.4317 | 6.1404 | 6.0582 |
| 5.49866E-05 | 0.000735679 | 8.681 | 6.7496 | N/A | 6.1408 | 6.0591 |
| 5.38685E-05 | 0.000962741 | 8.695 | 6.7505 | N/A | 6.1409 | 6.0596 |
| 5.28873E-05 | 0.001181545 | 8.7105 | 6.7509 | N/A | 6.1405 | 6.0636 |
| 5.08835E-05 | 0.001695261 | 8.721 | 6.7514 | N/A | 6.1392 | 6.0623 |
| 4.89717E-05 | 0.002193167 | 8.776 | 6.7527 | N/A | 6.1386 | 6.0656 |

D $^1$H NMR (600 MHz, 25° C) chemical shifts (ppm) of a 60 μM solution of 1 [H] in CDCl$_3$ upon incremental addition of α-Glc [G].

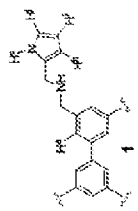

| Concentration | | k | j | a | i | h |
|---|---|---|---|---|---|---|
| [H] mol L$^{-1}$ | [G] mol L$^{-1}$ | H | H | H | H | H |
| 6.000058266 | 0 | 8.4935 | 6.7445 | 7.4236 | 6.1452 | 6.0539 |
| 5.71431E-05 | 0.000327255 | 8.5814 | 6.7445 | N/A | 6.1421 | 6.05680 |
| 5.60442E-05 | 0.000641923 | 8.6686 | 6.7436 | N/A | 6.1398 | 6.0593 |
| 5.49866E-05 | 0.000944717 | 8.7373 | 6.7441 | N/A | 6.1373 | 6.062 |
| 5.38685E-05 | 0.001236298 | 8.799 | 6.7444 | N/A | 6.1353 | 6.0646 |
| 5.29873E-05 | 0.001517273 | 8.857 | 6.7451 | N/A | 6.1335 | 6.0671 |
| 5.08835E-05 | 0.002078957 | 8.9497 | 6.7456 | N/A | 6.131 | 6.0715 |
| 4.89717E-05 | 0.002781967 | 9.04 | 6.7453 | 7.4311 | 6.129 | 6.076 |

N/A-Peak could not be resolved

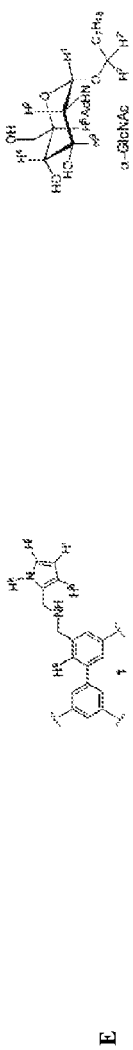

¹H NMR (600 MHz, 25° C) chemical shifts (ppm) of a 60 μM solution of 1 [H] in CDCl₃ upon incremental addition of α-GlcNAc [G].

| Concentration [H] mol·L⁻¹ | [G] mol·L⁻¹ | k H | a H | j H | i H | h H |
|---|---|---|---|---|---|---|
| 0.0000658286 | 0 | 8.533 | 7.4272 | 6.7461 | 6.1448 | 6.0545 |
| 5.71431E-05 | 0.000279528 | 8.614 | 7.4218 | 6.7458 | 6.1428 | 6.0573 |
| 5.60442E-05 | 0.000548308 | 8.6868 | N/A | 6.7478 | 6.1395 | 6.0608 |
| 5.49868E-05 | 0.000806943 | 8.749 | 7.4496 | 6.7513 | 6.138 | 6.0645 |
| 5.39685E-05 | 0.00101566 | 8.827 | 7.4592 | 6.7536 | 6.1381 | 6.0688 |
| 5.29073E-05 | 0.0012796 | N/A | 7.4688 | 6.7572 | 6.1391 | 6.0736 |
| 5.06835E-05 | 0.0013038478 | N/A | N/A | 6.7642 | 6.1329 | 6.0848 |
| 4.85717E-05 | 0.002376 | N/A | 7.4317 | N/A | N/A | N/A |

F

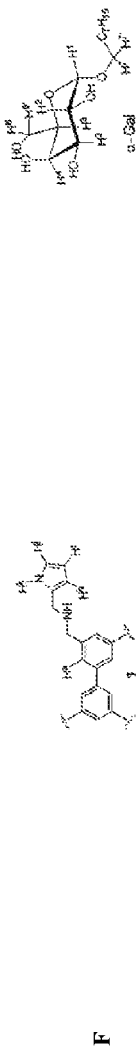

¹H NMR (600 MHz, 25° C) chemical shifts (ppm) of a 60 μM solution of 1 [H] in CDCl₃ upon incremental addition of α-Gal [G].

| Concentration [H] mol·L⁻¹ | [G] mol·L⁻¹ | k H | a H | j H | i H | h H |
|---|---|---|---|---|---|---|
| 0.0000477.18 | 0 | 8.5082 | 7.4253 | 6.745 | 6.145 | 6.0537 |
| 4.67824E-05 | 0.000312078 | 8.5105 | N/A | 6.7443 | 6.1436 | 6.0541 |
| 4.53282E-05 | 0.000463673 | 8.5406 | N/A | 6.7443 | 6.1425 | 6.0539 |
| 4.58927E-05 | 0.000612154 | N/A | N/A | 6.7435 | 6.1414 | 6.0546 |
| 4.50175E-05 | 0.000900986 | 8.5871 | N/A | 6.7446 | 6.1413 | 6.0543 |
| 4.41833E-05 | 0.001178963 | 8.5702 | N/A | 6.7448 | 6.1388 | 6.0538 |
| 4.22283E-05 | 0.001651044 | N/A | N/A | 6.7455 | 6.1352 | 6.0582 |
| 4.57824E-05 | 0.000312078 | N/A | N/A | 6.7521 | 6.1337 | 6.0557 |

N/A-Peak could not be resolved

FIGURES 15E-15F

I. $^1$H NMR (600 MHz, 20° C) chemical shifts (ppm) of a .06 mM solution of 1 [H] in CDCl$_3$ upon incremental addition of β-Man [G].

| Concentration [H], mol L$^{-1}$ | [G], mol L$^{-1}$ | k H | a H | j H | i H | h H |
|---|---|---|---|---|---|---|
| 0.000058626 | 0 | 8.4718 | 7.4227 | 6.7439 | 6.1463 | 6.0532 |
| 5.83E-05 | 5.82E-05 | 8.5181 | 7.4227 | 6.7442 | 6.1444 | 6.055 |
| 5.80E-05 | 0.000124288 | 8.5664 | 7.4232 | 6.7456 | 6.143 | 6.0579 |
| 5.78E-05 | 0.000020295 | 8.6188 | 7.4243 | 6.7474 | 6.1421 | 6.0508 |
| 5.75E-05 | 0.000277226 | 8.6754 | 7.4255 | 6.7489 | 6.1409 | 6.0638 |
| 5.69E-05 | 0.000441141 | 8.7952 | N/A | 6.7548 | 6.1388 | 6.0727 |
| 5.64E-05 | 0.000541531 | 8.8684 | N/A | 6.7605 | 6.1367 | 6.0794 |
| 5.53E-05 | 0.000938741 | 9.0907 | 7.4426 | 6.7737 | 6.1353 | 6.095 |
| 5.43E-05 | 0.001115231 | 9.237 | 7.4522 | 6.7835 | 6.1338 | 6.1055 |
| 5.33E-05 | 0.001411746 | 9.3172 | 7.463 | 6.7904 | 6.1322 | N/A |
| 5.23E-05 | 0.001168343 | 9.4077 | 7.4735 | 6.7982 | 6.1319 | N/A |
| 5.14E-05 | 0.000206793 | 9.4878 | N/A | 6.8053 | 6.1328 | N/A |
| 5.05E-05 | 0.002498138 | N/A | N/A | 6.8106 | 6.1326 | N/A |
| 4.97E-05 | 0.002884478 | N/A | N/A | 6.8149 | 6.133 | N/A |

N/A-Peak could not be resolved.

J. $^1$H NMR (600 MHz, 15° C) chemical shifts (ppm) of a .06 mM solution of 1 [H] in CDCl$_3$ upon incremental addition of β-Man [G].

| Concentration [H], mol L$^{-1}$ | [G], mol L$^{-1}$ | k H | a H | j H | i H | h H |
|---|---|---|---|---|---|---|
| 0.000058626 | 0 | 8.5121 | 7.4228 | 6.7506 | 6.1473 | 6.0546 |
| 5.83E-05 | 5.82E-05 | 8.6072 | 7.4225 | 6.7526 | 6.1448 | 6.0592 |
| 5.80E-05 | 0.000124288 | 8.7243 | 7.4244 | 6.7574 | 6.1426 | 6.0665 |
| 5.78E-05 | 0.000020295 | 8.8451 | 7.4289 | 6.764 | 6.1407 | 6.0748 |
| 5.75E-05 | 0.000277226 | 8.9616 | N/A | 6.7709 | 6.1396 | 6.0831 |
| 5.69E-05 | 0.000441141 | 9.169 | N/A | 6.7859 | 6.1378 | 6.0989 |
| 5.64E-05 | 0.000541531 | 9.2891 | 7.4426 | 6.7955 | 6.1369 | 6.1095 |
| 5.53E-05 | 0.000938741 | 9.4571 | 7.4519 | 6.8084 | 6.1344 | N/A |
| 5.43E-05 | 0.001115231 | 9.5324 | 7.4561 | 6.8136 | 6.1338 | N/A |
| 5.33E-05 | 0.001411746 | 9.5701 | 7.4619 | 6.8171 | 6.134 | N/A |
| 5.23E-05 | 0.001168343 | 9.6066 | 7.4662 | 6.8185 | 6.1338 | N/A |
| 5.14E-05 | 0.000209793 | 9.6353 | N/A | 6.8205 | 6.1336 | N/A |
| 5.05E-05 | 0.002498138 | 9.6356 | N/A | 6.822 | 6.1334 | N/A |
| 4.97E-05 | 0.002883478 | N/A | N/A | 6.822 | 6.1326 | N/A |

N/A-Peak could not be resolved.

FIGURES 15I-15J

¹H NMR (600 MHz, 10° C) chemical shifts (ppm) of a .06 mM solution of 1 [H] in CDCl₃ upon incremental addition of β-Man [G]

Concentration

| [H] mol L⁻¹ | [G] mol L⁻¹ | k H | a H | j H | i H | h H |
|---|---|---|---|---|---|---|
| 0.000058626 | 0 | 8.5372 | 7.4225 | 6.7544 | 6.1478 | 6.0554 |
| 5.83E-05 | 5.82E-05 | 8.6809 | 7.4226 | 6.7584 | 6.1444 | 6.0633 |
| 5.80E-05 | 0.000124299 | 8.8619 | 7.4262 | 6.7688 | 6.1419 | 6.076 |
| 5.78E-05 | 0.000202295 | 9.035 | N/A | 6.78 | 6.1407 | 6.0879 |
| 5.76E-05 | 0.000277226 | 9.1713 | N/A | 6.7901 | 6.1399 | 6.0891 |
| 5.69E-05 | 0.000441141 | 9.3733 | 7.4419 | 6.8062 | 6.1388 | 6.1153 |
| 5.64E-05 | 0.000541631 | 9.4782 | 7.4474 | 6.8153 | 6.1371 | N/A |
| 5.53E-05 | 0.000938741 | 9.5625 | 7.4532 | 6.8232 | 6.1361 | N/A |
| 5.43E-05 | 0.001152351 | 9.6177 | 7.4557 | 6.8255 | 6.1361 | N/A |
| 5.33E-05 | 0.001411746 | 9.6392 | 7.4589 | 6.8257 | 6.1357 | N/A |
| 5.23E-05 | 0.00168343 | 9.6586 | 7.4671 | 6.8255 | 6.1349 | N/A |
| 5.14E-05 | 0.002039793 | 9.6733 | 7.4713 | 6.8258 | 6.1345 | N/A |
| 5.05E-05 | 0.002428138 | 9.6911 | N/A | 6.8255 | 6.134 | N/A |
| 4.97E-05 | 0.002883478 | 8.5372 | N/A | 6.8262 | 6.1334 | N/A |

FIGURE 15K

Determination of $K_1$ and $K_3$

$^1$H NMR (900 MHz, 25° C) chemical shifts (ppm) of a 1.0 mM solution of α-Man [G] in CDCl$_3$ upon the incremental addition of 1 [H].

| Concentration | | $^1$H NMR Peak Shift (δ) | | | | | | | | |
|---|---|---|---|---|---|---|---|---|---|---|
| [H] mol L$^{-1}$ | [G] mol L$^{-1}$ | k H | a H | j H | i H | h H | 1 G | 7 G | 5 G | 7' G |
| 0.000000 | 0.000620 | N/A | N/A | N/A | N/A | N/A | 4.8356 | 3.5682 | 3.6223 | 3.4641 |
| 0.000212 | 0.000618 | 8.9233 | 7.4469 | 6.7571 | 6.1372 | 6.0770 | 4.7961 | 3.5426 | 3.5709 | 3.3827 |
| 0.000421 | 0.000615 | 8.8783 | 7.4358 | 6.7530 | 6.1371 | 6.0712 | 4.7727 | 3.6376 | 3.5482 | 3.3691 |
| 0.000630 | 0.000613 | 8.8103 | 7.4295 | 6.7495 | 6.1372 | 6.0652 | 4.7616 | 3.6220 | 3.5297 | 3.3602 |
| 0.000836 | 0.000610 | 8.7959 | 7.4259 | 6.7480 | 6.1371 | 6.0637 | 4.7490 | 3.6076 | 3.5159 | 3.3566 |
| 0.001245 | 0.000605 | 8.7710 | 7.4211 | 6.7459 | 6.1375 | 6.0617 | 4.7293 | 3.5948 | 3.4978 | 3.3393 |
| 0.001647 | 0.000601 | 8.7615 | 7.4182 | 6.7443 | 6.1371 | 6.0602 | 4.7170 | 3.5928 | 3.4847 | 3.3333 |
| 0.002042 | 0.000596 | 8.7560 | 7.4161 | 6.7434 | 6.1377 | 6.0598 | 4.7071 | 3.5924 | 3.4795 | 3.3263 |
| 0.002432 | 0.000592 | 8.7561 | 7.4143 | 6.7422 | 6.1377 | 6.0593 | 4.7060 | 3.5912 | 3.4762 | 3.3213 |
| 0.003333 | 0.000574 | 8.7635 | 7.4083 | 6.7385 | 6.1371 | 6.0578 | 4.6794 | 3.5887 | 3.4573 | 3.3065 |
| 0.008100 | 0.000525 | 8.8076 | 7.3960 | 6.7286 | 6.1342 | 6.0551 | 4.6650 | 3.5819 | 3.4441 | 3.2895 |
| 0.018225 | 0.000431 | 8.8868 | 7.3788 | 6.7132 | 6.1360 | 6.0520 | 4.6404 | N/A | N/A | N/A |

C  $^1$H NMR (500 MHz, 15° C) chemical shifts (ppm) of a 1.0 mM solution of α-Glc [G] in CDCl$_3$ upon the incremental addition of 1 [H].

| Concentration | | | | | | $^1$H NMR Peak Shift (G) | | | | | |
|---|---|---|---|---|---|---|---|---|---|---|---|
| [H] mol L$^{-1}$ | [G] mol L$^{-1}$ | k H | a H | j H | i H | h H | 1 G | 6 G | 4 G | 2 G | 7 G |
| 0.000000 | 0.001000 | N/A | N/A | N/A | N/A | N/A | 4.8681 | 3.8461 | 3.5717 | 3.4734 | 3.4388 |
| 0.000249 | 0.000998 | 8.9822 | 7.4398 | 6.7617 | 6.1317 | 6.0724 | 4.8426 | N/A | 3.5248 | N/A | N/A |
| 0.000496 | 0.000992 | 9.0528 | 7.4368 | 6.7508 | 6.1322 | 6.0897 | 4.8106 | 3.7937 | 3.458 | N/A | N/A |
| 0.000741 | 0.000988 | 9.0488 | 7.4323 | 6.7495 | 6.1328 | 6.0684 | 4.7848 | 3.7688 | 3.405 | 3.332 | 3.3876 |
| 0.000984 | 0.000984 | 8.935 | 7.429 | 6.7487 | 6.1328 | 6.0673 | 4.7628 | 3.7466 | 3.3602 | 3.2946 | 3.3583 |
| 0.001465 | 0.000977 | 8.9137 | 7.4235 | 6.7468 | 6.1335 | 6.0647 | 4.7316 | 3.7176 | 3.2973 | 3.2416 | 3.3482 |
| 0.001938 | 0.000969 | 8.8991 | 7.4167 | 6.7448 | 6.1335 | 6.063 | 4.7078 | 3.6954 | 3.2498 | 3.2053 | 3.3337 |
| 0.002404 | 0.000962 | 8.893 | 7.4152 | 6.7426 | 6.1336 | 6.0616 | 4.692 | 3.6814 | 3.2204 | 3.1891 | 3.3210 |
| 0.002863 | 0.000954 | 8.8872 | 7.4112 | 6.7408 | 6.1333 | 6.0603 | 4.68 | 3.668 | 3.1955 | 3.1646 | 3.3192 |
| 0.004630 | 0.000926 | 8.8957 | 7.401 | 6.7345 | 6.1325 | 6.0573 | 4.6612 | 3.6378 | 3.13 | 3.13 | 3.2857 |
| 0.009534 | 0.000847 | 8.9478 | 7.3808 | 6.7217 | 6.1296 | 6.0537 | 4.623 | 3.5988 | 3.0848 | 3.0849 | 3.2621 |
| 0.019097 | 0.000694 | 9.0466 | 7.3588 | 6.704 | 6.1248 | 6.0505 | 4.6073 | 3.584 | 3.0736 | 3.0736 | 3.2535 |

N/A - Peak could not be resolved.

D  $^1$H NMR (500 MHz, 10° C) chemical shifts (ppm) of a 1.0 mM solution of α-Glc [G] in CDCl$_3$ upon the incremental addition of 1 [H].

| Concentration | | | | | | $^1$H NMR Peak Shift (G) | | | | | |
|---|---|---|---|---|---|---|---|---|---|---|---|
| [H] mol L$^{-1}$ | [G] mol L$^{-1}$ | k H | a H | j H | i H | h H | 1 G | 6 G | 4 G | 2 G | 7 G |
| 0.000000 | 0.001000 | N/A | N/A | N/A | N/A | N/A | 4.8667 | 3.8476 | 3.5743 | 3.475 | 3.4342 |
| 0.000249 | 0.000998 | 9.0632 | 7.4453 | 6.7546 | 6.1285 | 6.0765 | 4.8365 | N/A | 3.5136 | 3.4265 | 3.4139 |
| 0.000496 | 0.000992 | 9.0528 | 7.4387 | 6.7527 | 6.1297 | 6.0739 | 4.7984 | 3.7809 | 3.4316 | N/A | N/A |
| 0.000741 | 0.000988 | 9.0323 | 7.4333 | 6.7516 | 6.1313 | 6.071 | 4.7652 | 3.7499 | 3.3671 | 3.297 | 3.3709 |
| 0.000984 | 0.000984 | 9.0147 | 7.4287 | 6.7505 | 6.1312 | 6.0695 | 4.7392 | 3.7278 | 3.3161 | 3.2536 | 3.3516 |
| 0.001465 | 0.000977 | 8.9938 | 7.4218 | 6.7493 | 6.1322 | 6.0663 | 4.705 | 3.6848 | 3.2481 | 3.1957 | 3.3291 |
| 0.001938 | 0.000969 | 8.9848 | 7.4157 | 6.7458 | 6.1324 | 6.064 | 4.6813 | 3.671 | 3.2 | 3.1581 | 3.3096 |
| 0.002404 | 0.000962 | 8.961 | 7.4114 | 6.744 | 6.1322 | 6.0625 | 4.6685 | 3.6563 | 3.1723 | 3.1353 | 3.2992 |
| 0.002863 | 0.000954 | 8.9546 | 7.4068 | 6.7417 | 6.1321 | 6.0612 | 4.6534 | 3.6433 | 3.1475 | 3.1154 | 3.2888 |
| 0.004630 | 0.000926 | 8.9653 | 7.3949 | 6.7351 | 6.131 | 6.0581 | N/A | 3.6144 | 3.0804 | 3.0904 | 3.2692 |
| 0.009534 | 0.000847 | 9.0218 | 7.3718 | 6.72 | 6.1278 | 6.0535 | N/A | 3.5852 | 3.0543 | 3.0543 | 3.2446 |
| 0.019097 | 0.000694 | 9.1238 | 7.3481 | 6.7012 | 6.1226 | 6.0499 | N/A | 3.5797 | 3.0522 | 3.0522 | 3.2317 |

N/A - Peak could not be resolved

FIGURES 17C-D

E $^1$H NMR (500 MHz, 5° C) chemical shifts (ppm) of a 1.0 mM solution of α-Glc [G] in CDCl$_3$ upon the incremental addition of 1 [H].

| Concentration | | | | | | $^1$H NMR Peak Shift (δ) | | | | | |
|---|---|---|---|---|---|---|---|---|---|---|---|
| [H] mol L$^{-1}$ | [G] mol L$^{-1}$ | k H | a H | j H | i H | h H | 1 G | 6 G | 4 G | 2 G | 7' G |
| 0.000000 | 0.001000 | N/A | N/A | N/A | N/A | N/A | 4.8669 | 3.8463 | 3.5769 | 3.4778 | 3.4305 |
| 0.000249 | 0.000996 | 9.208 | 7.4515 | 6.7567 | 6.1262 | 6.082 | 4.8272 | N/A | 3.498 | 3.4061 | 3.4061 |
| 0.000496 | 0.000992 | 9.1593 | 7.4418 | 6.7549 | 6.1273 | 6.0776 | 4.7779 | 3.7634 | 3.3984 | 3.3183 | 3.3731 |
| 0.000741 | 0.000988 | 9.1254 | 7.4344 | 6.7531 | 6.1285 | 6.074 | 4.7388 | 3.7287 | 3.3219 | 3.2515 | 3.3566 |
| 0.000984 | 0.000984 | 9.1019 | 7.4286 | 6.7522 | 6.129 | 6.0717 | 4.7114 | 3.7025 | 3.265 | 3.2036 | 3.3318 |
| 0.001465 | 0.000977 | 9.0625 | 7.4193 | 6.7495 | 6.1301 | 6.0677 | 4.6747 | 3.6681 | 3.1924 | 3.1439 | 3.3046 |
| 0.002404 | 0.000962 | 9.0372 | 7.4058 | 6.7441 | 6.1307 | 6.0632 | 4.6364 | 3.6292 | 3.1184 | 3.0852 | 3.2744 |
| 0.002863 | 0.000954 | 9.0334 | 7.4009 | 6.7422 | 6.1303 | 6.0619 | 4.6238 | 3.6173 | 3.0963 | 3.0649 | 3.2654 |
| 0.004630 | 0.000926 | 9.0468 | 7.3862 | 6.7339 | 6.1292 | 6.0581 | 4.5995 | 3.5888 | 3.0421 | 3.0421 | 3.2441 |
| 0.009534 | 0.000847 | 9.1079 | 7.3804 | 6.7176 | 6.1254 | 6.0531 | 4.5822 | 3.557 | 3.0185 | 3.0185 | 3.2297 |
| 0.019097 | 0.000694 | 9.2099 | 7.3346 | 6.8973 | 6.1201 | 6.0491 | N/A | 3.5455 | 3.0243 | 3.0243 | 3.2139 |

N/A-Peak could not be resolved.

FIGURE 17E

B   ¹H NMR (800 MHz, 20° C) chemical shifts (ppm) of a 1.0 mM solution of α-GlcNAc [G] in CDCl₃ upon the incremental addition of 1 [H].

| Concentration [H] mol L⁻¹ | [G] mol L⁻¹ | k H | a H | j H | i H | h H | 1 G | 7 G | 4 G | 7' G | Ac G |
|---|---|---|---|---|---|---|---|---|---|---|---|
| 0.000000 | 0.001008 | N/A | N/A | N/A | N/A | N/A | 4.7821 | 3.6464 | 3.5845 | 3.3964 | 2.0889 |
| 0.000214 | 0.001002 | 8.9414 | 7.4526 | 6.7532 | 6.1339 | 6.0695 | 4.7568 | 3.6257 | 3.5245 | 3.3821 | 2.0562 |
| 0.000427 | 0.000998 | 8.927 | 7.449 | 6.7533 | 6.1347 | 6.0696 | 4.7344 | 3.6078 | 3.4722 | 3.3699 | 2.044 |
| 0.000638 | 0.000994 | 8.9262 | 7.4412 | 6.7534 | 6.1354 | 6.0697 | 4.7113 | 3.5393 | 3.4193 | 3.3572 | 2.0319 |
| 0.000847 | 0.000990 | 8.9078 | 7.4378 | 6.7524 | 6.1357 | 6.0699 | 4.6915 | 3.5743 | 3.3721 | 3.347 | 2.0214 |
| 0.001261 | 0.000982 | 8.8912 | 7.4337 | 6.7512 | 6.1363 | 6.0673 | 4.6642 | 3.5538 | 3.3221 | 3.3221 | 2.0073 |
| 0.001668 | 0.000975 | 8.8713 | 7.4284 | 6.7492 | 6.1365 | 6.0653 | 4.6331 | 3.5298 | 3.2363 | 3.3147 | 1.991 |
| 0.002069 | 0.000967 | 8.8648 | 7.4247 | 6.7479 | 6.1368 | 6.0644 | 4.6113 | 3.5135 | 3.1894 | 3.3024 | 1.9798 |
| 0.002464 | 0.000960 | 8.8608 | 7.4199 | 6.7458 | 6.1364 | 6.0631 | 4.5936 | 3.4993 | 3.1488 | 3.2822 | 1.9688 |
| 0.003855 | 0.000931 | 8.8555 | 7.4097 | 6.7399 | 6.1366 | 6.0599 | 4.5529 | 3.467 | 3.0517 | 3.2762 | N/A |
| 0.008207 | 0.000853 | 8.9273 | 7.3962 | 6.7272 | 6.1329 | 6.0573 | 4.5003 | 3.4277 | 2.9381 | 3.2493 | N/A |
| 0.016439 | 0.000693 | 9.0375 | 7.362 | 6.7107 | 6.1267 | 6.0545 | 4.4853 | 3.4123 | 2.9046 | 3.2294 | N/A |

N/A-Peak could not be resolved.

C   ¹H NMR (800 MHz, 15° C) chemical shifts (ppm) of a 1.0 mM solution of α-GlcNAc [G] in CDCl₃ upon the incremental addition of mM 1 [H].

| Concentration [H] mol L⁻¹ | [G] mol L⁻¹ | k H | a H | j H | i H | h H | 1 G | 7 G | 4 G | 7' G | Ac G |
|---|---|---|---|---|---|---|---|---|---|---|---|
| 0.000000 | 0.001008 | N/A | N/A | N/A | N/A | N/A | 4.7807 | 3.6443 | 3.5877 | 3.3926 | 2.0715 |
| 0.000214 | 0.001002 | 9.0503 | 7.4615 | 6.7568 | 6.1331 | 6.0727 | 4.7482 | 3.6172 | 3.5105 | 3.3747 | 2.054 |
| 0.000427 | 0.000998 | 9.0242 | 7.449 | 6.7672 | 6.133 | 6.073 | 4.7212 | 3.5952 | 3.4464 | 3.3597 | 2.0387 |
| 0.000638 | 0.000994 | 9.0075 | 7.4465 | 6.7665 | 6.1337 | 6.072 | 4.693 | 3.573 | 3.3801 | 3.3442 | 2.0239 |
| 0.000847 | 0.000990 | 8.9907 | 7.4401 | 6.7658 | 6.1343 | 6.0712 | 4.6701 | 3.5662 | 3.3298 | 3.3286 | 2.0116 |
| 0.001261 | 0.000982 | 8.9662 | 7.4363 | 6.7544 | 6.1349 | 6.0692 | 4.6432 | 3.5345 | 3.266 | 3.3173 | 1.9983 |
| 0.001668 | 0.000975 | 8.9381 | 7.4281 | 6.752 | 6.1356 | 6.0668 | 4.6048 | 3.5066 | 3.1763 | 3.298 | 1.9774 |
| 0.002069 | 0.000967 | 8.9298 | 7.4235 | 6.7504 | 6.1358 | 6.0655 | 4.5817 | 3.4891 | 3.1243 | 3.2832 | 1.9655 |
| 0.002464 | 0.000960 | 8.9239 | 7.4173 | 6.748 | 6.135 | 6.064 | 4.5636 | 3.4745 | 3.084 | 3.2734 | 1.9552 |
| 0.003855 | 0.000931 | 8.9208 | 7.4046 | 6.7412 | 6.1346 | 6.0606 | 4.5253 | 3.4488 | 2.8943 | 3.2518 | N/A |
| 0.008207 | 0.000853 | 8.9951 | 7.3775 | 6.7269 | 6.1314 | 6.0573 | 4.4915 | 3.4111 | 2.8863 | 3.2252 | N/A |
| 0.016439 | 0.000693 | 9.1093 | 7.3511 | 6.7087 | 6.1269 | 6.0541 | 4.4729 | 3.4008 | 2.8779 | 3.217 | N/A |

N/A-Peak could not be resolved.

FIGURES 19B-19C

D $^1$H NMR (800 MHz, 10° C) chemical shifts (ppm) of a 1.0 mM solution of α-GlcNAc [G] in CDCl$_3$ upon the incremental addition of 1 [H].

| Concentration [H] mol L$^{-1}$ | [G] mol L$^{-1}$ | k H | a H | j H | i H | h H | $^1$H NMR Peak Shift (δ) 1 G | 7 G | 4 G | 7' G | Ac G |
|---|---|---|---|---|---|---|---|---|---|---|---|
| 0.000000 | 0.001006 | N/A | N/A | N/A | N/A | N/A | 4.779 | 3.6406 | 3.5024 | 3.388 | 2.073 |
| 0.000214 | 0.001002 | 9.1712 | 7.4715 | 6.76 | 6.13 | 6.076 | 4.7386 | 3.607 | 3.4939 | 3.3655 | 2.0505 |
| 0.000427 | 0.000998 | 9.1297 | 7.4544 | 6.7607 | 6.1312 | 6.0767 | 4.7066 | 3.5811 | 3.4187 | 3.3448 | 2.0324 |
| 0.000638 | 0.000994 | 9.1058 | 7.4519 | 6.7597 | 6.1319 | 6.0748 | 4.6727 | 3.5549 | 3.3334 | 3.3334 | 2.0143 |
| 0.000847 | 0.000990 | 9.0784 | 7.4435 | 6.7593 | 6.1329 | 6.074 | 4.647 | 3.5353 | 3.2758 | 3.3152 | 2.0004 |
| 0.001261 | 0.000982 | 9.0604 | 7.4402 | 6.7581 | 6.1332 | 6.0724 | 4.6324 | 3.5216 | 3.2423 | 3.3049 | 1.9933 |
| 0.001668 | 0.000975 | 9.011 | 7.4275 | 6.7545 | 6.1343 | 6.0604 | 4.5746 | 3.4816 | 3.1136 | 3.2763 | 1.9623 |
| 0.002069 | 0.000967 | 9.0008 | 7.4213 | 6.7528 | 6.1345 | 6.0868 | 4.5518 | 3.4651 | 3.0591 | 3.2644 | 1.9504 |
| 0.002464 | 0.000960 | 8.9831 | 7.4137 | 6.7499 | 6.1337 | 6.0847 | 4.5341 | 3.4512 | 3.0236 | 3.2539 | 1.9403 |
| 0.003985 | 0.000931 | 8.9885 | 7.398 | 6.742 | 6.1332 | 6.061 | 4.4984 | 3.4236 | 2.8881 | 3.2336 | N/A |
| 0.008207 | 0.000853 | 9.0723 | 7.3671 | 6.728 | 6.1297 | 6.0574 | 4.4849 | 3.3965 | 2.863 | 3.2113 | N/A |
| 0.016439 | 0.000699 | 9.1884 | 7.3368 | 6.7061 | 6.1248 | 6.0536 | 4.4623 | 3.3891 | 2.8543 | 3.2044 | N/A |

N/A=Peak could not be resolved.

E $^1$H NMR (800 MHz, 5° C) chemical shifts (ppm) of a 1.0 mM solution of α-GlcNAc [G] in CDCl$_3$ upon the incremental addition of 1 [H].

| Concentration [H] mol L$^{-1}$ | [G] mol L$^{-1}$ | k H | a H | j H | i H | h H | $^1$H NMR Peak Shift (δ) 1 G | 7 G | 4 G | 7' G | Ac G |
|---|---|---|---|---|---|---|---|---|---|---|---|
| 0.000000 | 0.001006 | N/A | N/A | N/A | N/A | N/A | 4.7768 | 3.6371 | 3.599 | 3.383 | 2.0738 |
| 0.000214 | 0.001002 | 9.2919 | 7.4817 | 6.7633 | 6.127 | 6.0797 | 4.7278 | 3.5955 | 3.4766 | 3.3556 | 2.0492 |
| 0.000427 | 0.000998 | 9.2385 | 7.4603 | 6.7643 | 6.1292 | 6.0803 | 4.6906 | 3.5656 | 3.3862 | 3.3354 | 2.0251 |
| 0.000638 | 0.000994 | 9.2061 | 7.4574 | 6.7627 | 6.13 | 6.0775 | 4.6511 | 3.5353 | 3.3334 | 3.3034 | 2.0038 |
| 0.000847 | 0.000990 | 9.188 | 7.4484 | 6.762 | 6.1311 | 6.0764 | 4.6222 | 3.5136 | 3.2233 | 3.2966 | 1.9883 |
| 0.001261 | 0.000982 | 9.1543 | 7.4435 | 6.7614 | 6.1315 | 6.0751 | 4.61 | 3.5014 | 3.1952 | 3.2893 | 1.9822 |
| 0.001668 | 0.000975 | 9.0862 | 7.4204 | 6.7586 | 6.1331 | 6.0699 | 4.5466 | 3.4687 | 3.0507 | 3.2583 | 1.9479 |
| 0.002069 | 0.000967 | 9.0734 | 7.4187 | 6.7544 | 6.1332 | 6.0678 | 4.5229 | 3.4415 | 2.9979 | 3.2452 | 1.9353 |
| 0.002464 | 0.000960 | 8.9643 | 7.4096 | 6.7515 | 6.1325 | 6.0658 | 4.5072 | 3.4287 | 2.9629 | 3.2358 | 1.9266 |
| 0.003985 | 0.000931 | 9.0574 | 7.3904 | 6.7423 | 6.1317 | 6.0612 | 4.4768 | 3.4047 | 2.89 | 3.2171 | N/A |
| 0.008207 | 0.000853 | 9.1501 | 7.3586 | 6.7248 | 6.1281 | 6.0572 | 4.4514 | 3.3827 | 2.8342 | 3.1989 | N/A |
| 0.016439 | 0.000699 | 9.2652 | 7.3252 | 6.7028 | 6.1227 | 6.0525 | 4.4537 | 3.3789 | N/A | 3.1927 | N/A |

N/A=Peak could not be resolved.

FIGURES 19D-19E

C  $^1$H NMR (500 MHz, 15° C) chemical shifts (ppm) of a 0.664 mM solution of α-Gal [G] in CDCl$_3$ upon the incremental addition of 1 [H].

| Concentration | | | | | | $^1$H NMR Peak Shift (δ) | | | | | | | |
|---|---|---|---|---|---|---|---|---|---|---|---|---|---|
| [H] mol L$^{-1}$ | [G] mol L$^{-1}$ | k H | a H | j H | i H | h H | 1 G | 6 G | 2' G | 5 G | 7 G | 4 G |
| 0.000000 | 0.000664 | N/A | N/A | N/A | N/A | N/A | 4.9906 | 3.7305 | 3.4472 | 3.8231 | 3.7208 | 4.1046 |
| 0.000175 | 0.000679 | 8.7692 | 7.4085 | 6.7487 | 6.1371 | 6.0654 | 4.9466 | 3.7254 | 3.4359 | 3.8062 | 3.7092 | 4.0722 |
| 0.000348 | 0.000675 | 8.7474 | 7.4041 | 6.748 | 6.136 | 6.0638 | 4.9345 | 3.7017 | 3.4261 | 3.7922 | N/A | 4.0417 |
| 0.000519 | 0.000671 | 8.7402 | 7.4048 | 6.7472 | 6.1361 | 6.0631 | 4.9215 | N/A | 3.4159 | 3.7731 | N/A | 4.0112 |
| 0.000689 | 0.000667 | 8.7385 | 7.4054 | 6.7469 | 6.1387 | 6.0625 | 4.911 | 3.682 | 3.4077 | 3.76 | N/A | 3.985 |
| 0.001021 | 0.000660 | 8.7304 | 7.4041 | 6.7455 | 6.1391 | 6.0612 | 4.8909 | 3.6468 | 3.391 | 3.7452 | 3.6623 | 3.9352 |
| 0.001346 | 0.000652 | 8.7258 | 7.4035 | 6.7445 | 6.1394 | 6.0602 | 4.8762 | 3.6218 | 3.3789 | 3.7115 | 3.6492 | 3.8966 |
| 0.001664 | 0.000645 | 8.7279 | 7.4016 | 6.7433 | 6.139 | 6.0594 | 4.8629 | 3.5981 | 3.368 | 3.6838 | 3.6361 | N/A |
| 0.002575 | 0.000624 | 8.7282 | 7.3978 | 6.7404 | 6.1393 | 6.0581 | 4.8345 | 3.5487 | 3.344 | 3.6656 | 3.6143 | N/A |
| 0.004735 | 0.000573 | 8.7498 | 7.3869 | 6.7337 | 6.1381 | 6.0554 | 4.7933 | 3.4808 | 3.3082 | 3.5879 | N/A | N/A |
| 0.007782 | 0.000502 | 8.7904 | 7.3736 | 6.726 | 6.1369 | 6.0535 | 4.7668 | 3.4432 | 3.2885 | 3.5632 | N/A | N/A |

N/A-Peak could not be resolved.

D  $^1$H NMR (500 MHz, 10° C) chemical shifts (ppm) of a 0.684 mM solution of α-Gal [G] in CDCl$_3$ upon the incremental addition of 1 [H].

| Concentration | | | | | | $^1$H NMR Peak Shift (δ) | | | | | | | |
|---|---|---|---|---|---|---|---|---|---|---|---|---|---|
| [H] mol L$^{-1}$ | [G] mol L$^{-1}$ | k H | a H | j H | i H | h H | 1 G | 6 G | 2' G | 5 G | 7 G | 4 G |
| 0.000000 | 0.000684 | N/A | N/A | N/A | N/A | N/A | 4.9625 | 3.7296 | 3.444 | 3.8227 | 3.7291 | 4.1066 |
| 0.000175 | 0.000679 | 8.8491 | 7.3957 | 6.7517 | 6.1348 | 6.0683 | 4.9446 | N/A | 3.4297 | 3.8012 | 3.7046 | 4.0655 |
| 0.000348 | 0.000675 | 8.8212 | 7.3997 | 6.7508 | 6.1364 | 6.0657 | 4.9283 | 3.7073 | 3.4167 | 3.7785 | 3.691 | 4.0253 |
| 0.000519 | 0.000671 | 8.8116 | 7.4004 | 6.7496 | 6.1366 | 6.0657 | 4.9123 | 3.6995 | 3.4036 | 3.7572 | 3.6773 | 3.9865 |
| 0.000689 | 0.000667 | 8.803 | 7.401 | 6.7491 | 6.1371 | 6.0648 | 4.8991 | N/A | 3.3925 | 3.7386 | N/A | 3.9534 |
| 0.001021 | 0.000660 | 8.7942 | 7.3997 | 6.7475 | 6.1377 | 6.0632 | 4.8751 | 3.6326 | 3.3727 | 3.7063 | 3.6454 | 3.8914 |
| 0.001346 | 0.000652 | 8.7863 | 7.3987 | 6.7464 | 6.1383 | 6.0621 | 4.8579 | 3.6007 | 3.3585 | 3.6823 | 3.6302 | N/A |
| 0.001664 | 0.000645 | 8.787 | 7.3969 | 6.745 | 6.136 | 6.0611 | 4.843 | 3.576 | 3.351 | 3.6621 | 3.6175 | N/A |
| 0.002575 | 0.000624 | 8.7853 | 7.3917 | 6.7416 | 6.1384 | 6.0588 | 4.8126 | 3.5211 | 3.3195 | 3.6197 | 3.5808 | N/A |
| 0.004735 | 0.000573 | 8.8056 | 7.3782 | 6.7337 | 6.1375 | 6.0557 | 4.773 | 3.4531 | 3.2848 | 3.5623 | 3.5562 | N/A |
| 0.007782 | 0.000502 | 8.8535 | 7.3628 | 6.7249 | 6.1357 | 6.0535 | 4.7493 | 3.4201 | 3.266 | 3.5352 | N/A | N/A |

N/A-Peak could not be resolved.

FIGURES 21C-21D

E  $^1$H NMR (500 MHz, 5° C) chemical shifts (ppm) of a 0.684 mM solution of α-Gal [G] in CDCl$_3$ upon the incremental addition of 1 [H].

| Concentration | | | | | | | $^1$H NMR Peak Shift (δ) | | | | | |
|---|---|---|---|---|---|---|---|---|---|---|---|---|
| [H] mol L$^{-1}$ | [G] mol L$^{-1}$ | k H | a H | j H | i H | h H | 1 G | 6 G | 7' G | 1' G | 5 G | 4 G |
| 0.000000 | 0.000684 | N/A | N/A | N/A | N/A | N/A | 4.964 | 3.728 | 3.4402 | N/A | 3.8222 | 4.1088 |
| 0.000175 | 0.000679 | 8.9307 | 7.3905 | 6.7541 | 6.1331 | 6.0712 | 4.9419 | N/A | 3.4228 | N/A | N/A | 4.0575 |
| 0.000348 | 0.000675 | 8.9061 | 7.3946 | 6.753 | 6.1341 | 6.0702 | 4.9208 | N/A | 3.4054 | N/A | 3.7665 | 4.004 |
| 0.000519 | 0.000671 | 8.889 | 7.3953 | 6.7519 | 6.135 | 6.0682 | 4.9011 | N/A | 3.3893 | N/A | 3.7384 | 3.9561 |
| 0.000689 | 0.000667 | 8.8777 | 7.3958 | 6.7508 | 6.1354 | 6.0671 | 4.8848 | N/A | 3.3756 | N/A | 3.7154 | 3.9145 |
| 0.001021 | 0.000660 | 8.8624 | 7.3947 | 6.7488 | 6.136 | 6.0648 | 4.8571 | 3.5928 | 3.3621 | 3.5265 | 3.6771 | N/A |
| 0.001346 | 0.000652 | 8.8522 | 7.3931 | 6.7476 | 6.1368 | 6.0636 | 4.8369 | 3.5567 | 3.3349 | 3.6106 | 3.6486 | N/A |
| 0.001664 | 0.000645 | 8.8512 | 7.3911 | 6.7458 | 6.1366 | 6.0624 | 4.8216 | 3.5266 | 3.3215 | 3.5822 | 3.6272 | N/A |
| 0.002575 | 0.000624 | 8.8491 | 7.3844 | 6.7421 | 6.1369 | 6.0590 | 4.7898 | 3.4689 | 3.2952 | 3.5703 | 3.5825 | N/A |
| 0.004735 | 0.000573 | 8.8758 | 7.3681 | 6.7334 | 6.1361 | 6.0561 | 4.7542 | 3.4075 | 3.2631 | N/A | N/A | N/A |
| 0.007782 | 0.000502 | 8.932 | 7.3498 | 6.7231 | 6.134 | 6.0531 | 4.7339 | N/A | 3.2433 | N/A | 3.5132 | N/A |

N/A-Peak could not be resolved.

FIGURE 21E

A     $^1$H NMR (500 MHz, 25° C) chemical shifts (ppm) of a 1.0 mM solution of β-Man [G] in CDCl₃ upon the incremental addition of 1 [H].

| Concentration | | | | | | $^1$H NMR Peak Shift (δ) | | | | |
|---|---|---|---|---|---|---|---|---|---|---|
| [H] mol L⁻¹ | [G] mol L⁻¹ | k H | a H | j H | i H | h H | 1 G | 7 G | 3 G | 5 G |
| 0.000000 | 0.000976 | N/A | N/A | N/A | N/A | N/A | 4.5329 | 3.5455 | 3.5154 | 3.2891 |
| 0.000249 | 0.000972 | 9.045 | 7.4475 | 6.7697 | 6.1319 | 6.0845 | 4.5012 | 3.531 | 3.4825 | 3.2336 |
| 0.000496 | 0.000968 | 8.976 | 7.4454 | 6.7603 | 6.1326 | 6.0788 | 4.4853 | 3.5239 | 3.4573 | 3.205 |
| 0.000741 | 0.000964 | 8.937 | 7.4399 | 6.7565 | 6.1332 | 6.074 | 4.4701 | 3.5169 | 3.4349 | 3.1781 |
| 0.000984 | 0.000961 | 8.9633 | 7.4365 | 6.7538 | 6.1334 | 6.071 | 4.4609 | 3.5123 | 3.4175 | 3.1615 |
| 0.001466 | 0.000953 | 8.8633 | 7.432 | 6.7498 | 6.1342 | 6.0663 | 4.4413 | 3.5034 | 3.3892 | 3.1297 |
| 0.001938 | 0.000946 | 8.8271 | 7.4268 | 6.7424 | 6.1345 | 6.0638 | 4.4305 | 3.4977 | 3.3685 | 3.1096 |
| 0.004198 | 0.000910 | 8.7938 | 7.4176 | 6.7399 | 6.1348 | 6.0583 | 4.3867 | 3.4803 | 3.3242 | 3.0653 |
| 0.008247 | 0.000847 | 8.1000 | 7.4043 | 6.7303 | 6.1338 | 6.0552 | 4.376 | 3.4707 | 3.2895 | 3.0388 |
| 0.018855 | 0.000682 | 8.8992 | 7.3821 | 6.7122 | 6.1301 | 6.052 | N/A | 3.468 | 3.287 | 3.012 |

N/A-Peak could not be resolved.

FIGURE 23A

B    $^1$H NMR (900 MHz, 20° C) chemical shifts (ppm) of a 1.0 mM solution of β-Man [G] in CDCl$_3$ upon the incremental addition of 1 [H].

| Concentration | | $^1$H NMR Peak Shift (δ) | | | | | | | |
|---|---|---|---|---|---|---|---|---|---|
| [H] mol L$^{-1}$ | [G] mol L$^{-1}$ | k H | a H | j H | i H | h H | 1 G | 7 G | 3 G | 5 G |
| 0.000000 | 0.000976 | N/A | N/A | N/A | N/A | N/A | 4.5307 | 3.5408 | 3.5198 | 3.2855 |
| 0.000249 | 0.000972 | 9.197 | 7.4551 | 6.7751 | 6.1297 | 6.0918 | 4.4915 | 3.5228 | 3.4781 | 3.2168 |
| 0.000496 | 0.000968 | 9.109 | 7.4486 | 6.7676 | 6.1311 | 6.0845 | 4.472 | 3.5147 | 3.4434 | 3.1794 |
| 0.000741 | 0.000964 | 9.0411 | 7.4413 | 6.7623 | 6.1310 | 6.0788 | 4.4545 | 3.5068 | 3.4135 | 3.1468 |
| 0.000984 | 0.000961 | 8.9919 | 7.4365 | 6.7587 | 6.132 | 6.0746 | 4.4442 | 3.5022 | 3.3928 | 3.1275 |
| 0.001465 | 0.000953 | 8.9275 | 7.4311 | 6.7534 | 6.1329 | 6.0685 | 4.4237 | 3.4931 | 3.359 | 3.0909 |
| 0.001938 | 0.000946 | 8.8911 | 7.4268 | 6.7533 | 6.1331 | 6.0653 | 4.4133 | 3.4881 | 3.3432 | 3.0759 |
| 0.004198 | 0.000910 | 8.8565 | 7.4136 | 6.7417 | 6.1332 | 6.0589 | 4.3827 | 3.472 | 3.3226 | 3.0408 |
| 0.008247 | 0.000847 | 8.6742 | 7.3928 | 6.7308 | 6.132 | 6.0549 | 4.3643 | 3.4646 | 3.2843 | 3.0288 |
| 0.018855 | 0.000682 | 8.9714 | 7.3727 | 6.7133 | 6.1275 | 6.0511 | 4.3538 | 3.463 | 3.279 | 3.017 |

N/A-Peak could not be resolved.

C    $^1$H NMR (900 MHz, 15° C) chemical shifts (ppm) of a 1.0 mM solution of β-Man [G] in CDCl$_3$ upon the incremental addition of 1 [H].

| Concentration | | $^1$H NMR Peak Shift (δ) | | | | | | | |
|---|---|---|---|---|---|---|---|---|---|
| [H] mol L$^{-1}$ | [G] mol L$^{-1}$ | k H | a H | j H | i H | h H | 1 G | 7 G | 3 G | 5 G |
| 0.000000 | 0.000976 | N/A | N/A | N/A | N/A | N/A | 4.5273 | 3.5353 | 3.5244 | 3.2637 |
| 0.000249 | 0.000972 | 9.317 | 7.4599 | 6.7854 | 6.1294 | 6.1025 | 4.4813 | 3.5146 | 3.4657 | 3.1963 |
| 0.000496 | 0.000968 | 9.2236 | 7.4502 | 6.7768 | 6.1306 | 6.0922 | 4.4582 | 3.5066 | 3.4215 | 3.1495 |
| 0.000741 | 0.000964 | 9.1452 | 7.4422 | 6.7699 | 6.1314 | 6.0851 | 4.4389 | 3.4971 | 3.3902 | 3.1127 |
| 0.000984 | 0.000961 | 9.0833 | 7.4372 | 6.765 | 6.1316 | 6.0793 | 4.4276 | 3.4929 | 3.3656 | 3.0905 |
| 0.001465 | 0.000953 | 9.0093 | 7.43 | 6.7578 | 6.1319 | 6.072 | 4.4071 | 3.4833 | 3.331 | 3.0557 |
| 0.001938 | 0.000946 | 8.9647 | 7.4252 | 6.7539 | 6.1323 | 6.0676 | 4.398 | 3.4794 | 3.3137 | 3.0396 |
| 0.004198 | 0.000910 | 8.9245 | 7.4091 | 6.7434 | 6.1318 | 6.0597 | 4.3702 | 3.4655 | 3.2653 | 3.0161 |
| 0.008247 | 0.000847 | 8.9453 | 7.3904 | 6.7308 | 6.1305 | 6.0552 | 4.3549 | 3.462 | 3.269 | 3.007 |
| 0.018855 | 0.000682 | 9.0499 | 7.3621 | 6.7078 | 6.1251 | 6.0604 | 4.342 | 3.4693 | 3.27 | 2.9999 |

N/A-Peak could not be resolved.

FIGURES 23B-23C

D  $^1$H NMR (900 MHz, 10° C) chemical shifts (ppm) of a 1.3 mM solution of β-Man [G] in CDCl$_3$ upon the incremental addition of 1 [H].

| Concentration | | | | | | $^1$H NMR Peak Shift (δ) | | | | |
|---|---|---|---|---|---|---|---|---|---|---|
| [H] mol L$^{-1}$ | [G] mol L$^{-1}$ | k H | a H | j H | i H | h H | 1 G | 7' G | 3 G | 5 G |
| 0.000000 | 0.000976 | N/A | N/A | N/A | N/A | N/A | 4.5216 | 3.5274 | 3.5343 | 3.2738 |
| 0.000249 | 0.000972 | 9.439 | 7.4657 | 6.7966 | 6.1299 | 6.1124 | 4.4707 | 3.5061 | 3.4587 | 3.1762 |
| 0.000496 | 0.000968 | 9.3526 | 7.4533 | 6.7869 | 6.1305 | 6.1066 | 4.4436 | 3.496 | 3.4033 | 3.1196 |
| 0.000741 | 0.000964 | 9.2965 | 7.4434 | 6.7782 | 6.1309 | 6.0915 | 4.4231 | 3.4662 | 3.3633 | 3.0787 |
| 0.000984 | 0.000961 | 9.1815 | 7.438 | 6.7716 | 6.131 | 6.0845 | 4.4109 | 3.4845 | 3.338 | 3.054 |
| 0.001465 | 0.000953 | 9.0896 | 7.4287 | 6.7623 | 6.1312 | 6.0752 | 4.3917 | 3.4748 | 3.304 | 3.0213 |
| 0.001938 | 0.000946 | 9.0398 | 7.4229 | 6.7575 | 6.1313 | 6.0701 | 4.3835 | 3.4715 | 3.2882 | 3.0099 |
| 0.004198 | 0.000910 | 8.9997 | 7.4034 | 6.7448 | 6.1308 | 6.0604 | 4.3595 | 3.4554 | 3.2673 | 2.9942 |
| 0.008247 | 0.000847 | 9.0283 | 7.3817 | 6.7305 | 6.1285 | 6.0554 | 4.3472 | 3.4462 | 3.261 | 2.984 |
| 0.018855 | 0.000682 | 9.132 | 7.3603 | 6.705 | 6.1228 | 6.0498 | N/A | 3.4403 | 3.2652 | 2.9841 |

N/A-Peak could not be resolved.

FIGURE 23D

A    ¹H NMR (900 MHz, 25° C) chemical shifts (ppm) of a 1.0 mM solution of β-Glc [G] in CDCl₃ upon the incremental addition of 1 [H].

| Concentration | | | | | | | | ¹H NMR Peak Shift (δ) | | | | | |
|---|---|---|---|---|---|---|---|---|---|---|---|---|---|
| [H] mol L⁻¹ | [G] mol L⁻¹ | k H | a H | j H | i H | h H | 1 G | 4 G | 3 G | 2" G | 5 G | 2 G |
| 0.000000 | 0.000964 | N/A | N/A | N/A | N/A | N/A | 4.3107 | 3.6064 | 3.6795 | 3.5287 | 3.4041 | 3.355 |
| 0.000249 | 0.000950 | 9.021 | 7.4519 | 6.749 | 6.1259 | 6.0749 | 4.2342 | 3.5417 | 3.5319 | 3.5073 | 3.3642 | 3.2483 |
| 0.000496 | 0.000946 | 8.9789 | 7.4469 | 6.7457 | 6.1272 | 6.0718 | 4.2645 | N/A | N/A | N/A | 3.3337 | 3.1693 |
| 0.000741 | 0.000943 | 8.9121 | 7.4378 | 6.7441 | 6.1289 | 6.0673 | 4.2258 | 3.3944 | N/A | N/A | 3.2772 | 3.0152 |
| 0.000984 | 0.000939 | 8.8921 | 7.4352 | 6.7436 | 6.1297 | 6.066 | 4.2119 | 3.3605 | 3.4134 | 3.4475 | 3.2676 | 2.9595 |
| 0.001465 | 0.000932 | 8.8518 | 7.4302 | 6.7417 | 6.1311 | 6.0634 | 4.1885 | 3.3043 | 3.373 | 3.4279 | 3.2255 | 2.8590 |
| 0.001938 | 0.000924 | 8.8314 | 7.4269 | 6.7408 | 6.1321 | 6.0615 | 4.1713 | 3.2639 | 3.3466 | 3.4138 | 3.2006 | 2.8048 |
| 0.002404 | 0.000917 | 8.8143 | 7.4243 | 6.7396 | 6.1324 | 6.06 | 4.1593 | 3.2365 | 3.3267 | 3.4027 | 3.1859 | 2.7624 |
| 0.002863 | 0.000910 | 8.8056 | 7.4219 | 6.7385 | 6.1326 | 6.0592 | 4.1496 | 3.2144 | 3.3103 | 3.3946 | 3.1707 | 2.7252 |
| 0.004536 | 0.000883 | 8.7885 | 7.4144 | 6.7343 | 6.1334 | 6.0562 | 4.126 | 3.161 | 3.2739 | 3.3742 | 3.1418 | 2.6491 |
| 0.006634 | 0.000808 | 8.8154 | 7.3998 | 6.7247 | 6.132 | 6.0531 | 4.1086 | N/A | 3.2437 | 3.3569 | N/A | 2.6081 |
| 0.019097 | 0.000853 | 8.8349 | 7.3817 | 6.7103 | 6.1291 | 6.0507 | 4.1038 | 3.0871 | 3.2391 | 3.3427 | 3.1133 | 2.6271 |

N/A = Peak could not be resolved.

FIGURE 25A

B $^1$H NMR (900 MHz, 20° C) chemical shifts (ppm) of a 1.0 mM solution of β-Glc [G] in CDCl$_3$ upon the incremental addition of 1 [H].

| Concentration | | | | | | | $^1$H NMR Peak Shift (δ) | | | | | |
|---|---|---|---|---|---|---|---|---|---|---|---|---|
| [H], mol L$^{-1}$ | [G], mol L$^{-1}$ | k H | a H | j H | i H | h H | 1 G | 4 G | 3 G | 7' G | 5 G | 2 G |
| 0.000000 | 0.000954 | N/A | N/A | N/A | N/A | N/A | 4.3113 | 3.6089 | 3.5822 | 3.5256 | 3.4047 | 3.3567 |
| 0.002249 | 0.000950 | 9.1372 | 7.4606 | 6.7519 | 6.1231 | 6.0811 | 4.2778 | 3.5282 | 3.5192 | 3.4933 | 3.3524 | 3.2196 |
| 0.000496 | 0.000946 | 9.0914 | 7.4533 | 6.7502 | 6.1241 | 6.0768 | 4.2524 | N/A | N/A | 3.463 | 3.3145 | 3.1162 |
| 0.000741 | 0.000943 | 8.9960 | 7.4413 | 6.7472 | 6.1271 | 6.0707 | 4.2067 | 3.3458 | 3.4054 | 3.4412 | 3.2485 | 2.9367 |
| 0.000984 | 0.000939 | 8.9713 | 7.4375 | 6.7463 | 6.1278 | 6.0688 | 4.1907 | 3.3068 | 3.3798 | 3.4274 | 3.2255 | 2.8674 |
| 0.001465 | 0.000932 | 8.9183 | 7.4308 | 6.7441 | 6.1295 | 6.0651 | 4.1655 | 3.2487 | 3.3368 | 3.4066 | 3.1912 | 2.7592 |
| 0.001938 | 0.000924 | 8.896 | 7.4267 | 6.743 | 6.1304 | 6.0631 | 4.1438 | 3.2095 | 3.3114 | 3.3907 | 3.1711 | 2.7057 |
| 0.002404 | 0.000917 | 8.8734 | 7.4231 | 6.7414 | 6.1312 | 6.0614 | 4.1383 | 3.1789 | 3.2848 | 3.3823 | 3.1568 | 2.6878 |
| 0.002863 | 0.000910 | 8.8672 | 7.4203 | 6.7404 | 6.1315 | 6.0601 | 4.1285 | N/A | 3.2706 | 3.3732 | N/A | 2.6344 |
| 0.004630 | 0.000883 | 8.8463 | 7.4109 | 6.7352 | 6.1319 | 6.0568 | 4.1106 | 3.1146 | 3.2601 | 3.3536 | 3.1146 | 2.5789 |
| 0.008534 | 0.000808 | 8.8632 | 7.3935 | 6.7243 | 6.1304 | 6.0533 | 4.0954 | 3.0869 | 3.2293 | 3.3411 | 3.0869 | 2.5565 |
| 0.019097 | 0.000663 | 8.9532 | 7.3728 | 6.7086 | 6.1275 | 6.0501 | 4.0935 | 3.0778 | 3.2296 | 3.334 | 3.0894 | 2.5969 |

N/A-Peak could not be resolved

C $^1$H NMR (900 MHz, 15° C) chemical shifts (ppm) of a 1.0 mM solution of β-Glc [G] in CDCl$_3$ upon the incremental addition of 1 [H].

| Concentration | | | | | | | $^1$H NMR Peak Shift (δ) | | | | | |
|---|---|---|---|---|---|---|---|---|---|---|---|---|
| [H], mol L$^{-1}$ | [G], mol L$^{-1}$ | k H | a H | j H | i H | h H | 1 G | 4 G | 3 G | 7' G | 5 G | 2 G |
| 0.000000 | 0.000954 | N/A | N/A | N/A | N/A | N/A | 4.3122 | 3.6112 | 3.5843 | 3.5225 | 3.3882 | N/A |
| 0.000249 | 0.000950 | 9.2619 | 7.4716 | 6.7561 | 6.1195 | 6.0862 | 4.2705 | 3.5153 | 3.5086 | 3.4908 | 3.3405 | 3.1876 |
| 0.000496 | 0.000948 | 9.201 | 7.4613 | 6.7535 | 6.121 | 6.0819 | 4.2388 | 3.4231 | N/A | N/A | 3.2921 | 3.0572 |
| 0.000743 | 0.000943 | 9.0841 | 7.4449 | 6.7496 | 6.1244 | 6.0736 | 4.186 | 3.2924 | 3.3733 | 3.4214 | 3.2162 | 2.8499 |
| 0.000984 | 0.000939 | 9.0568 | 7.4402 | 6.7488 | 6.1258 | 6.0714 | 4.1657 | 3.2489 | 3.3449 | 3.4088 | 3.1953 | 2.7697 |
| 0.001465 | 0.000932 | 8.9899 | 7.4312 | 6.7461 | 6.1275 | 6.0667 | 4.1431 | 3.1843 | 3.3041 | 3.3836 | 3.1618 | 2.6685 |
| 0.001938 | 0.000924 | 8.9645 | 7.4261 | 6.7447 | 6.1287 | 6.0644 | 4.1276 | N/A | 3.2808 | 3.3707 | N/A | 2.6119 |
| 0.002404 | 0.000917 | 8.9384 | 7.4215 | 6.7429 | 6.1295 | 6.0623 | 4.118 | N/A | 3.263 | 3.3613 | N/A | 2.5767 |
| 0.002863 | 0.000910 | 8.9348 | 7.418 | 6.7417 | 6.1298 | 6.0611 | 4.1055 | 3.11 | 3.251 | 3.3522 | 3.11 | 2.5501 |
| 0.004630 | 0.000883 | 8.9127 | 7.4054 | 6.7356 | 6.1303 | 6.0571 | 4.0939 | N/A | 3.2275 | 3.3381 | N/A | 2.508 |
| 0.008534 | 0.000808 | 8.8676 | 7.3854 | 6.7233 | 6.1284 | 6.053 | 4.094 | 3.0654 | 3.2137 | 3.5233 | 3.0854 | 2.5134 |
| 0.019097 | 0.000663 | 9.03 | 7.3623 | 6.736 | 6.1251 | 6.0496 | 4.0882 | 3.0657 | 3.2222 | 3.3222 | 3.0687 | 2.5674 |

N/A-Peak could not be resolved

FIGURES 25B-25C

D $^1$H NMR (900 MHz, 10° C) chemical shifts (ppm) of a 1.0 mM solution of β-Glc [G] in CDCl$_3$ upon the incremental addition of 1 [H].

| Concentration [H] mol L$^{-1}$ | [G] mol L$^{-1}$ | k H | a H | j H | i H | h H | $^1$H NMR Peak Shift (δ) 1 G | 4 G | 3 G | 7 G | 5 G | 2 G |
|---|---|---|---|---|---|---|---|---|---|---|---|---|
| 0.000000 | 0.000954 | N/A | N/A | N/A | N/A | N/A | 4.3126 | 3.6138 | 3.5862 | 3.5195 | 3.4031 | 3.3802 |
| 0.000249 | 0.000950 | 9.3744 | 7.4842 | 6.7596 | 6.1171 | 6.0912 | 4.253 | N/A | N/A | N/A | 3.3237 | 3.1567 |
| 0.000496 | 0.000946 | 9.3082 | 7.4761 | 6.7569 | 6.1184 | 6.0864 | 4.2247 | 3.3868 | 3.4382 | 3.4517 | 3.2675 | 2.9981 |
| 0.000741 | 0.000943 | 9.1732 | 7.4489 | 6.7522 | 6.1219 | 6.0766 | 4.1652 | 3.2375 | 3.3405 | 3.4016 | 3.1839 | 2.7499 |
| 0.000984 | 0.000939 | 9.1385 | 7.4428 | 6.751 | 6.1232 | 6.0738 | 4.1463 | 3.1999 | 3.312 | 3.3865 | 3.1622 | 2.6776 |
| 0.001465 | 0.000932 | 9.0658 | 7.4315 | 6.7477 | 6.1254 | 6.068 | 4.1216 | 3.1271 | 3.272 | 3.3631 | 3.1271 | 2.5771 |
| 0.001938 | 0.000924 | 9.045 | 7.4267 | 6.7467 | 6.1266 | 6.0662 | 4.1103 | N/A | 3.2524 | 3.3522 | N/A | 2.5358 |
| 0.002404 | 0.000917 | 9.0107 | 7.4195 | 6.7441 | 6.1278 | 6.0631 | 4.0985 | N/A | 3.237 | 3.342 | 3.0998 | 2.4999 |
| 0.002863 | 0.000910 | 9.0053 | 7.415 | 6.7425 | 6.128 | 6.0617 | 4.0916 | 3.0587 | 3.226 | 3.3371 | 3.0801 | 2.4785 |
| 0.004639 | 0.000883 | 8.9884 | 7.4012 | 6.7361 | 6.1287 | 6.0577 | 4.0797 | 3.0412 | 3.12 | 3.3233 | 3.065 | 2.4561 |
| 0.009534 | 0.000808 | 9.038 | 7.3764 | 6.7219 | 6.1261 | 6.0529 | 4.0734 | 3.0318 | 3.2022 | 3.3094 | 3.0467 | 2.4759 |
| 0.019097 | 0.000663 | 9.1131 | 7.3507 | 6.7032 | 6.1227 | 6.049 | 4.0796 | 3.0518 | 3.2156 | 3.3097 | 3.0518 | 2.5417 |

N/A-Peak could not be resolved.

E $^1$H NMR (900 MHz, 5° C) chemical shifts (ppm) of a 1.0 mM solution of β-Glc [G] in CDCl$_3$ upon the incremental addition of 1 [H].

| Concentration [H] mol L$^{-1}$ | [G] mol L$^{-1}$ | k H | a H | j H | i H | h H | $^1$H NMR Peak Shift (δ) 1 G | 4 G | 3 G | 7 G | 5 G | 2 G |
|---|---|---|---|---|---|---|---|---|---|---|---|---|
| 0.000000 | 0.000954 | N/A | N/A | N/A | N/A | N/A | 4.3123 | 3.6172 | 3.5852 | 3.516 | 3.3953 | 3.3621 |
| 0.000249 | 0.000950 | 9.4746 | 7.4963 | 6.7642 | 6.115 | 6.0969 | 4.2554 | N/A | N/A | N/A | 3.3079 | 3.1292 |
| 0.000496 | 0.000946 | 9.4003 | 7.4790 | 6.7598 | 6.1152 | 6.0901 | 4.2109 | 3.3513 | 3.4145 | 3.4386 | 3.2402 | 2.9415 |
| 0.000741 | 0.000943 | 9.2602 | 7.4527 | 6.7545 | 6.1198 | 6.0794 | 4.1446 | 3.1819 | 3.3091 | 3.3833 | 3.1551 | 2.6644 |
| 0.000984 | 0.000939 | 9.2195 | 7.4453 | 6.7526 | 6.1211 | 6.0760 | 4.1273 | 3.1399 | 3.2822 | 3.3692 | 3.1313 | 2.5949 |
| 0.001485 | 0.000932 | 9.1439 | 7.4317 | 6.7493 | 6.1238 | 6.0698 | 4.1021 | 3.0754 | 3.2446 | 3.3442 | 3.0920 | 2.4983 |
| 0.001938 | 0.000924 | 9.1236 | 7.4263 | 6.7478 | 6.1245 | 6.0677 | 4.0923 | 3.0637 | 3.2311 | 3.3372 | 3.0802 | 2.4685 |
| 0.002404 | 0.000917 | 9.0891 | 7.4171 | 6.7450 | 6.1259 | 6.0643 | 4.0817 | 3.0393 | 3.2151 | 3.325 | 3.0696 | 2.4331 |
| 0.002863 | 0.000910 | 9.0801 | 7.4110 | 6.7427 | 6.1261 | 6.0620 | 4.0768 | 3.0193 | 3.207 | 3.3292 | 3.0573 | 2.4158 |
| 0.004639 | 0.000883 | 9.0725 | 7.3947 | 6.7355 | 6.1263 | 6.0576 | 4.067 | 3.0032 | 3.1949 | 3.3084 | 3.0468 | 2.4040 |
| 0.009534 | 0.000808 | 9.1208 | 7.3664 | 6.7193 | 6.1239 | 6.0526 | 4.0651 | 3.0114 | 3.1842 | 3.298 | 3.0337 | 2.4446 |
| 0.019097 | 0.000663 | 9.2015 | 7.3373 | 6.6994 | 6.1200 | 6.0481 | 4.0755 | 3.0381 | 3.2082 | 3.2981 | 3.0381 | 2.5305 |

N/A-Peak could not be resolved.

FIGURES 25D-25E

C  $^1$H NMR (900 MHz, 15° C) chemical shifts (ppm) of a 1.0 mM solution of β-GlcNAc [G] in CDCl$_3$ upon the incremental addition of 1 [H].

| Concentration | | $^1$H NMR Peak Shift (δ) | | | | | | | | | | |
|---|---|---|---|---|---|---|---|---|---|---|---|---|
| [H] mol L$^{-1}$ | [G] mol L$^{-1}$ | k H | a H | j H | i H | h H | N-H G | 1 G | 4 G | 7' G | 5 G | 2 G |
| 0.000000 | 0.000996 | N/A | N/A | N/A | N/A | N/A | 5.7673 | 4.4162 | 3.533 | 3.4701 | 3.4099 | 3.3497 |
| 0.000212 | 0.000992 | 8.8849 | 7.4396 | 6.7685 | 6.1374 | 6.0683 | 5.7897 | 4.3836 | N/A | N/A | 3.3728 | 3.3292 |
| 0.000421 | 0.000988 | 8.8385 | 7.4426 | 6.7592 | 6.1358 | 6.0711 | 5.8416 | 4.3719 | 3.3998 | 3.4367 | 3.3356 | 3.3164 |
| 0.000630 | 0.000984 | 8.8572 | 7.4339 | 6.756 | 6.1367 | 6.0666 | 5.8328 | 4.3597 | 3.351 | 3.4253 | N/A | N/A |
| 0.000836 | 0.000980 | 8.9188 | 7.4355 | 6.7558 | 6.1353 | 6.0674 | 5.8489 | 4.3489 | N/A | 3.4175 | N/A | N/A |
| 0.001245 | 0.000973 | 8.8901 | 7.428 | 6.7529 | 6.1358 | 6.0642 | 5.8717 | 4.3332 | N/A | 3.4026 | N/A | N/A |
| 0.001647 | 0.000965 | 8.8079 | 7.4285 | 6.7514 | 6.1347 | 6.0639 | 5.869 | 4.3203 | N/A | 3.3913 | N/A | 3.2684 |
| 0.002042 | 0.000958 | 8.9046 | 7.4227 | 6.7497 | 6.1347 | 6.0627 | N/A | 4.3101 | 3.1935 | 3.3819 | 3.2239 | 3.2627 |
| 0.002432 | 0.000950 | 8.9071 | 7.42 | 6.748 | 6.1341 | 6.0618 | N/A | 4.3018 | 3.1693 | 3.3745 | 3.2092 | 3.2553 |
| 0.002933 | 0.000922 | 8.9162 | 7.4096 | 6.7422 | 6.1331 | 6.0589 | N/A | 4.2811 | 3.1028 | 3.3567 | 3.1705 | 3.2412 |
| 0.008100 | 0.000844 | 8.9494 | 7.3894 | 6.7297 | 6.1306 | 6.0552 | N/A | 4.2479 | 3.0148 | 3.3235 | 3.1147 | 3.2235 |
| 0.016225 | 0.000692 | 9.0302 | 7.3661 | 6.7131 | 6.1267 | 6.0517 | N/A | 4.2208 | 2.9716 | 3.2991 | 3.0735 | 3.2208 |

N/A - Peak could not be resolved.

FIGURE 27C

B    $^1$H NMR (500 MHz, 20° C) chemical shifts (ppm) of a 1.0 mM solution of β-Gal [G] in CDCl$_3$ upon the incremental addition of 1 [H].

| Concentration [H]$_t$ mol L$^{-1}$ | [G]$_t$ mol L$^{-1}$ | k H | a H | j H | i H | h H | 1 G | 3 G | 5 G | 7 G |
|---|---|---|---|---|---|---|---|---|---|---|
| 0.000000 | 0.000684 | N/A | N/A | N/A | N/A | N/A | 4.2567 | 3.6425 | 3.5636 | 3.5186 |
| 0.000175 | 0.000680 | 8.6616 | 7.422 | 6.7485 | 6.1372 | 6.0566 | 4.2419 | 3.6056 | 3.5413 | 3.5019 |
| 0.000349 | 0.000676 | 8.6642 | 7.4212 | 6.7434 | 6.1378 | 6.0564 | 4.2261 | N/A | 3.5213 | 3.4863 |
| 0.000520 | 0.000672 | 8.6614 | 7.4207 | 6.7399 | 6.1378 | 6.0562 | 4.2168 | N/A | 3.5047 | 3.4731 |
| 0.000689 | 0.000668 | 8.6611 | 7.4198 | 6.7397 | 6.138 | 6.0562 | 4.2061 | N/A | 3.4899 | 3.4602 |
| 0.001022 | 0.000660 | 8.6501 | 7.4184 | 6.739 | 6.1384 | 6.0578 | 4.198 | 3.5012 | 3.4598 | N/A |
| 0.001347 | 0.000653 | 8.6477 | 7.4165 | 6.7384 | 6.1386 | 6.0569 | 4.1725 | 3.4743 | N/A | N/A |
| 0.001664 | 0.000645 | 8.6426 | 7.4161 | 6.7378 | 6.1388 | 6.0565 | 4.1624 | 3.462 | 3.4167 | N/A |
| 0.002575 | 0.000624 | 8.6366 | 7.4118 | 6.736 | 6.1394 | 6.0553 | 4.1298 | 3.4075 | 3.3425 | N/A |
| 0.004736 | 0.000574 | 8.6416 | 7.4041 | 6.7322 | 6.1394 | 6.0541 | 4.0977 | N/A | 3.2645 | N/A |
| 0.007762 | 0.000503 | 8.6661 | 7.3945 | 6.7272 | 6.1387 | 6.0525 | 4.071 | N/A | 3.2239 | N/A |

N/A–Peak could not be resolved.

C    $^1$H NMR (500 MHz, 15° C) chemical shifts (ppm) of a 0.684 mM solution of β-Gal [G] in CDCl$_3$ upon the incremental addition of 1 [H].

| Concentration [H]$_t$ mol L$^{-1}$ | [G]$_t$ mol L$^{-1}$ | k H | a H | j H | i H | h H | 1 G | 3 G | 5 G | 7 G |
|---|---|---|---|---|---|---|---|---|---|---|
| 0.000000 | 0.000684 | N/A | N/A | N/A | N/A | N/A | 4.26 | 3.6429 | 3.5661 | 3.5112 |
| 0.000175 | 0.000680 | 8.8371 | 7.4211 | 6.7442 | 6.1323 | 6.0634 | 4.2323 | N/A | 3.5261 | 3.48 |
| 0.000349 | 0.000676 | 8.8291 | 7.4195 | 6.7434 | 6.1328 | 6.0627 | 4.209 | N/A | 3.4518 | 3.4518 |
| 0.000520 | 0.000672 | 8.812 | 7.4181 | 6.7432 | 6.1338 | 6.0619 | 4.1994 | 3.5045 | 3.4488 | 3.4304 |
| 0.000689 | 0.000668 | 8.803 | 7.4164 | 6.7428 | 6.1342 | 6.0615 | 4.1729 | 3.4749 | N/A | N/A |
| 0.001022 | 0.000660 | 8.7788 | 7.4139 | 6.7421 | 6.1354 | 6.0601 | 4.1478 | 3.4328 | 3.3842 | 3.3692 |
| 0.001347 | 0.000653 | 8.7652 | 7.4113 | 6.7412 | 6.1359 | 6.0591 | 4.1272 | 3.3987 | 3.3031 | N/A |
| 0.001664 | 0.000645 | 8.7562 | 7.4102 | 6.7407 | 6.1363 | 6.0588 | 4.1122 | 3.383 | 3.2817 | N/A |
| 0.002575 | 0.000624 | 8.7392 | 7.4038 | 6.7382 | 6.1373 | 6.0569 | 4.0854 | 3.328 | 3.2058 | N/A |
| 0.004736 | 0.000574 | 8.7426 | 7.3921 | 6.7337 | 6.1378 | 6.0546 | 4.0535 | N/A | 3.1519 | N/A |
| 0.007762 | 0.000503 | 8.7816 | 7.3782 | 6.7268 | 6.1364 | 6.0531 | 4.0362 | N/A | 3.136 | N/A |
| 0.009535 | 0.000462 | 8.8091 | 7.3718 | 6.7235 | 6.1359 | 6.0523 | 4.0303 | N/A | 3.1375 | N/A |

N/A–Peak could not be resolved.

FIGURES 29B-29C

D    $^1$H NMR (500 MHz, 10° C) chemical shifts (ppm) of a 0.684 mM solution of β-Gal [G] in CDCl$_3$ upon the incremental addition of 1 [H].

| Concentration | | k | a | j | i | h | 1 | 3 | 5 | 7 |
|---|---|---|---|---|---|---|---|---|---|---|
| [H] mol L$^{-1}$ | [G] mol L$^{-1}$ | H | H | H | H | H | G | G | G | G |
| 0.000000 | 0.000684 | N/A | N/A | N/A | N/A | N/A | 4.262 | 3.6451 | 3.5975 | 3.5361 |
| 0.000175 | 0.000680 | 8.9336 | 7.4217 | 6.7449 | 6.1293 | 6.0658 | 4.2266 | N/A | 3.5166 | 3.4675 |
| 0.000349 | 0.000676 | 8.9178 | 7.4169 | 6.7442 | 6.1299 | 6.0654 | 4.1971 | 3.5155 | N/A | 3.4328 |
| 0.000520 | 0.000672 | 8.8944 | 7.417 | 6.744 | 6.1312 | 6.0639 | 4.1744 | 3.4772 | N/A | N/A |
| 0.000689 | 0.000668 | 8.8762 | 7.4145 | 6.7434 | 6.1317 | 6.063 | 4.1545 | 3.4436 | 3.3637 | 3.382 |
| 0.001022 | 0.000660 | 8.8451 | 7.4118 | 6.7434 | 6.1343 | 6.0622 | 4.1265 | 3.397 | 3.2911 | 3.25 |
| 0.001347 | 0.000653 | 8.8283 | 7.4081 | 6.7415 | 6.1344 | 6.0599 | 4.1204 | 3.3901 | 3.2387 | N/A |
| 0.001664 | 0.000645 | 8.8142 | 7.4064 | 6.7413 | 6.1352 | 6.0592 | 4.1106 | N/A | 3.2132 | N/A |
| 0.002575 | 0.000624 | 8.7943 | 7.3983 | 6.7386 | 6.1364 | 6.0572 | 4.0836 | N/A | 3.1471 | N/A |
| 0.004738 | 0.000574 | 8.8007 | 7.3843 | 6.7334 | 6.1368 | 6.0546 | 4.0354 | N/A | 3.108 | N/A |
| 0.007782 | 0.000503 | 8.8463 | 7.368 | 6.7261 | 6.1358 | 6.0527 | 4.0198 | N/A | 3.1092 | N/A |
| 0.009535 | 0.000462 | 8.8732 | 7.3604 | 6.7221 | 6.1347 | 6.0522 | 4.0156 | N/A | N/A | N/A |

N/A–Peak could not be resolved

E    $^1$H NMR (500 MHz, 5°C) chemical shift (ppm) of a 0.684 mM solution of β-Gal [G] in CDCl$_3$ upon the incremental addition of 1 [H].

| Concentration | | k | a | j | i | h | 1 | 3 | 5 | 7 |
|---|---|---|---|---|---|---|---|---|---|---|
| [H] mol L$^{-1}$ | [G] mol L$^{-1}$ | H | H | H | H | H | G | G | G | G |
| 0.000000 | 0.000684 | N/A | N/A | N/A | N/A | N/A | 4.2653 | 3.6462 | 3.5687 | 3.5046 |
| 0.000175 | 0.000680 | 9.0393 | 7.422 | 6.7449 | 6.1249 | 6.0685 | 4.2196 | 3.5528 | 3.5048 | 3.4538 |
| 0.000349 | 0.000676 | 9.0125 | 7.4185 | 6.7442 | 6.1264 | 6.0671 | 4.1841 | 3.4919 | 3.4312 | 3.4124 |
| 0.000520 | 0.000672 | 8.9805 | 7.4153 | 6.7439 | 6.1278 | 6.0656 | 4.1565 | 3.446 | 3.3646 | 3.3804 |
| 0.000689 | 0.000668 | 8.9571 | 7.4123 | 6.7433 | 6.1289 | 6.0642 | 4.1343 | 3.4088 | 3.303 | 3.3535 |
| 0.001022 | 0.000650 | 8.9167 | 7.4076 | 6.7425 | 6.1309 | 6.0623 | 4.103 | 3.3576 | 3.224 | N/A |
| 0.001347 | 0.000653 | 8.898 | 7.4037 | 6.7415 | 6.1322 | 6.0608 | 4.0818 | 3.3197 | 3.1734 | N/A |
| 0.001664 | 0.000645 | 8.8757 | 7.4006 | 6.7409 | 6.1332 | 6.0597 | 4.0708 | N/A | 3.1461 | N/A |
| 0.002575 | 0.000624 | 8.8536 | 7.3917 | 6.7385 | 6.1347 | 6.0575 | 4.0432 | 3.2592 | 3.0956 | N/A |
| 0.004738 | 0.000574 | 8.8684 | 7.3745 | 6.7325 | 6.135 | 6.0553 | 4.018 | N/A | 3.0705 | N/A |
| 0.007782 | 0.000503 | 8.9189 | 7.3556 | 6.7242 | 6.1338 | 6.0527 | 4.0053 | 3.2051 | N/A | N/A |
| 0.009535 | 0.000462 | 8.9508 | 7.347 | 6.7205 | 6.1325 | 6.0519 | 4.0011 | N/A | N/A | N/A |

N/A–Peak could not be resolved

FIGURES 29D-29E

| Sugar | Temperature (°C) | Log $K_1$ | Log $K_2$ | Log $K_3$ |
|---|---|---|---|---|
| α-Glc | 25 | 2.73 ± 0.01 | - | - |
|  | 20 | 2.86 ± 0.01 | - | - |
|  | 15 | 3.02 ± 0.02 | - | - |
|  | 10 | 3.20 ± 0.02 | - | - |
|  | 5 | 3.38 ± 0.03 | - | - |
| β-Glc | 25 | 3.23 ± 0.02 | - | - |
|  | 20 | 3.47 ± 0.03 | - | - |
|  | 15 | 3.65 ± 0.04 | - | 0.45 ± 0.04 |
|  | 10 | 3.87 ± 0.08 | - | 0.57 ± 0.04 |
|  | 5 | 4.12 ± 0.11 | - | 0.63 ± 0.04 |
| α-GlcNAc | 25 | 2.69 ± 0.03 | - | - |
|  | 20 | 2.83 ± 0.02 | - | - |
|  | 15 | 2.98 ± 0.03 | - | - |
|  | 10 | 3.16 ± 0.03 | - | - |
|  | 5 | 3.22 ± 0.04 | - | - |
| β-GlcNAc | 25 | 2.65 ± 0.02 | - | - |
|  | 20 | 2.84 ± 0.02 | - | - |
|  | 15 | 2.93 ± 0.02 | - | - |
| α-Man | 25 | 2.57 ± 0.19 | 3.71 ± 0.10 | - |
| β-Man | 25 | 2.46 ± 0.31 | 3.34 ± 0.11 | 2.45 ± 0.09 |
|  | 20 | 2.75 ± 0.12 | 3.57 ± 0.04 | 2.57 ± 0.04 |
|  | 15 | 2.97 ± 0.08 | 3.89 ± 0.03 | 2.74 ± 0.07 |
|  | 10 | 3.27 ± 0.07 | 4.10 ± 0.03 | 2.87 ± 0.07 |
| α-Gal | 25 | 2.18 ± 0.02 | - | - |
|  | 20 | 2.31 ± 0.03 | - | - |
|  | 15 | 2.51 ± 0.03 | - | - |
|  | 10 | 2.66 ± 0.04 | - | - |
|  | 5 | 2.87 ± 0.05 | - | - |
| β-Gal | 25 | 2.59 ± 0.03 | - | - |
|  | 20 | 2.78 ± 0.03 | - | - |
|  | 15 | 3.05 ± 0.04 | - | - |
|  | 10 | 3.20 ± 0.04 | - | - |
|  | 5 | 3.40 ± 0.05 | - | - |

FIGURE 31

| Glycoside | Complexation-Induced Shifts (ppm) | Observed Intermolecular Cross-Peaks and Calculated Distances (Å) |
|---|---|---|
| βGlc | $H_1 - 0.207$<br>$H_2 - 0.728$<br>$H_3 - 0.340$<br>$H_4 - 0.519$<br>$H_6 - 0.291$<br>$H_7 - 0.186$ | 1:β-Glc<br>$H_1, H_a - w\ (2.94)$<br>$H_2, H_a - m\ (3.06)$<br>$H_3, H_a - w\ (3.83)$<br>$H_4, H_a - m\ (2.92)$<br>$H_5, H_a - w\ (3.06)$ |
| βMan | $H_1 - 0.157$<br>$H_3 - 0.228$<br>$H_4 - 0.730$<br>$H_6 - 0.277$<br>$H_7 - 0.078$ | 1:β-Man<br>$H_4, H_a - m\ (3.33)$<br>$1_2$:β-Man<br>$H_3, H_8\ H_3, H_9$<br>$H_1, H_9\ H_h, H_9$ |

FIGURE 35

CARBOHYDRATE-SELECTIVE RECEPTORS

This application is a national stage application under 35 U.S.C. 371 of PCT Application No. PCT/US2013/042888, filed May 28, 2013, which claims the benefit of U.S. Provisional Patent Application Ser. Nos. 61/652,011, filed May 25, 2012, and 61/708,893, filed Oct. 2, 2012, which are hereby incorporated by reference in their entirety.

This invention was made with government support under Air Force Office of Scientific Research grant number FA9550-11-1-0032. The government has certain rights in this invention.

FIELD OF THE INVENTION

The present invention is directed to synthetic carbohydrate receptors and methods of making the same. The present invention further relates to methods of diagnosing and treating carbohydrate-mediated disorders.

BACKGROUND OF THE INVENTION

Natural saccharide-binding proteins, including lectins and periplasmic substrate-binding proteins, use water desolvation, hydrogen bonding (H-bonding), and C—H$\cdots\pi$ interactions to selectively recognize glycans that may differ only by the orientation of a single hydroxyl group to achieve binding affinities, $K_a$s, as high at $10^6$ M$^{-1}$ (ESSENTIALS OF GLYCOBIOLOGY (Ajit Varki et al. eds., Cold Spring Harbor Laboratory Press 1999); BEAT ERNST et al., CARBOHYDRATES IN CHEMISTRY AND BIOLOGY PART II: BIOLOGY OF SACCHARIDES (Wiley-VCH 2000); Ambrosi et al., *Org. Biomol. Chem.* 3:1593-1608 (2005); Toone, *Curr. Opin. Struct. Biol.* 4:719-728 (1994); Lemieux, *Acc. Chem. Res.* 29:373-380 (1996)). Selective carbohydrate recognition with artificial receptors remains a major area of investigation because of the challenge of differentiating between molecules with subtle structural differences, their ability to reveal fundamental aspects of saccharide binding, and their potential applications in disease detection, therapy, or catalysis (Davis, *Org. Biomol. Chem.* 7:3629-3638 (2009); Davis & Wareham, *Angew. Chem. Int. Ed.* 38:2978-2996 (1999); Mazik, *RSC Adv.* 2:2630-2642 (2012); Mazik, *Chem. Soc. Rev.* 38:935-956 (2009); Kubik, *Angew. Chem. Int. Ed.* 48:1722-1725 (2009); Jin et al., *Med. Res. Rev.* 30:171-257 (2010); Walker et al., *Cell. Mol. Life Sci.* 66:3177-3191 (2009)). These receptors employ both covalent and noncovalent interactions to stabilize complexation. For example, the reversible reaction of boronic acids to syn-diols has been employed successfully to selectively bind sugars, such as glucose and ribose, and sugar alcohols, like sorbitol and mannitol (Jin et al., *Med. Res. Rev.* 30:171-257 (2010); TONY D. JAMES et al., BORONIC ACIDS IN SACCHARIDE RECOGNITION (The Royal Society of Chemistry 2006); James et al., *Angew. Chem. Int. Ed.* 35:1910-1922 (1996)), but the recognition of monosaccharides possessing axial hydroxyl groups, such as mannose, remains challenging by this approach. Alternatively, by following Cram's principles of electronic complementarity and structural preorganization (D. J. CRAM & J. M. CRAM, CONTAINER MOLECULES AND THEIR GUESTS (The Royal Society of Chemistry 1997); Artz & Cram, *J. Am. Chem. Soc.* 106:2160-2171 (1984); Cram et al., *J. Am. Chem. Soc.* 103:6228-6232 (1981); D. J. Cram and J. M. Cram, *Acc. Chem. Res.* 11:8-14 (1978)), molecules were created that bind through only noncovalent interactions and do not distort significantly upon binding. In these receptors, recognition groups are rigidly positioned in three dimensional space, like natural lectins (Weis & Drickamer, *Annu. Rev. Biochem.* 65:441-473 (1996)), to overcome entropy-enthalpy compensation whereby any favorable enthalpic change that arises from the formation of noncovalent bonds is offset by the entropically unfavorable decrease of the internal motions of host and guest upon binding (Liu & Guo, *Chem. Rev.* 101:673-695 (2001)).

Noteworthy examples of preorganized synthetic saccharide receptors that bind through only noncovalent interactions are the "temple" family of hosts developed by Davis and coworkers and the "tripodal" receptors pioneered by the Roelens (Arda et al., *Chem. Eur. J.* 17:4821-4829 (2011); Cacciarini et al., *Org. Biomol. Chem.* 9:1085-1091 (2011); Nativi et al., *Chem. Eur. J.* 17:4814-4820 (2011); Arda et al., *Eur. J. Org. Chem.* 2010:64-71 (2010); Arda et al., *Chem. Eur. J.* 16:414-418 (2010); Nativi et al., *J. Am. Chem. Soc.* 129:4377-4385 (2007); Nativi et al., *Org. Lett.* 9:4685-4688 (2007); Cacciarini et al., *J. Org. Chem.* 72:3933-3936 (2007); Vacca et al., *J. Am. Chem. Soc.* 126:16456-16465 (2004)) and Mazik groups (Mazik & Buthe, *Org. Biomol. Chem.* 6:1558-1568 (2008); Mazik & Hartmann, *J. Org. Chem.* 73:7444-7450 (2008); Mazik et al., *Chem. Eur. J.* 15:9147-9159 (2009); Mazik & Sonnenberg, *J. Org. Chem.* 75:6416-6423 (2010); Mazik & Geffert, *Org. Biomol. Chem.* 9:2319-2326 (2011)). The temple receptors position polar amidopyridine groups between apolar aromatic surfaces, and these receptors are highly selective for mono- and disaccharides containing all equatorial hydroxide groups, such as β-glucose (Glc) (Barwell et al., *Angew. Chem. Int. Ed.* 48:7673-7676 (2009)), β-N-acetylglucosamine (GlcNAc) (Ferrand et al., *Angew. Chem. Int. Ed.* 48:1775-1779 (2009)), and β-D-cellobioside (Sookcharoenpinyo et al., *Angew. Chem. Int. Ed.* 51:4586-4590 (2012); Ferrand et al., *Science* 318:619-622 (2007)) in water. The tripodal receptors rely upon a 1,3,5-triethylbenzene scaffold to rigidly orient three aminopyrrolitic arms that can form hydrogen bonds with saccharide hydroxyl groups. The preorganization induced by the three ethyl arms add an estimated 4.5 kcal mol$^{-1}$ in additional stabilization upon complexation (Stack et al., *J. Am. Chem. Soc.* 115:6466-6467 (1993)). The tripodal receptors bind strongly to glycosides with an affinity of $10^2$ to $10^5$ M$^{-1}$ in chloroform and acetonitrile, and by changing to a chiral diaminopyrrolic motif, high selectivity for octylmannosides in acetonitrile has been observed, ranging from 1:7 β-GlcNAc:α-Man to 1:38 α-Gal:β-Man (Nativi et al., *Chem. Eur. J.* 17:4814-4820 (2011)). Mannose is a particularly interesting monosaccharide target, because it is a biomarker for several cancers (de Leoz et al., *Mol. Cell. Proteomics* 10:M110.002717 (2011); Ann et al., *Curr. Opin. Chem. Biol.* 13:601-607 (2009)), and as a consequence developing mannose specific synthetic receptors remains an active area of research (Arda et al., *Chem. Eur. J.* 17:4821-4829 (2011); Nativi et al., *Chem. Eur. J.* 17:4814-4820 (2011); Arda et al., *Eur. J. Org. Chem.* 2010:64-71 (2010); Arda et al., *Chem. Eur. J.* 16:414-418 (2010); Nativi et al., *Org. Lett.* 9:4685-4688 (2007); Nakagawa et al., *J. Am. Chem. Soc.* 133:17485-17493 (2011)). However, synthetic carbohydrate receptors with increased binding affinity, expanded substrate scope beyond all-equatorial glycosides, and increased selectivity to levels comparable with their biological counterparts are still needed before these receptors become more widely utilized.

SUMMARY OF THE INVENTION

A first aspect of the present invention is directed to a compound comprising Formula (I):

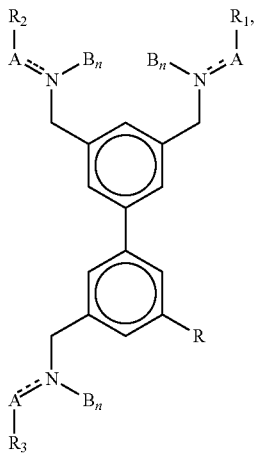

(I)

wherein
R is a targeting moiety, a tag, a pharmaceutically active moiety, a surface immobilization moiety, a moiety of Formula II

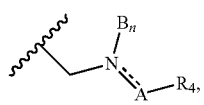

(II)

or a
moiety of Formula III

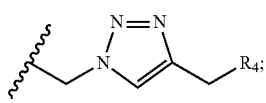

(III)

≡≡≡ is a single or a double bond;
A is selected from the group consisting of: (1) —CH$_2$—; (2) —C(O)—; and 3) =CH—;
B is H, and n is 0 or 1;
each of $R_1$, $R_2$, $R_3$, and $R_4$ is a heterocycle or a heteroaryl containing 1-5 heteroatoms selected from the group consisting of nitrogen, sulfur, and oxygen, wherein $R_1$, $R_2$, $R_3$, and $R_4$ can be the same or different;
$R_1$, $R_2$, $R_3$, and $R_4$ can be optionally substituted 1 to 4 times with substituents selected from the group consisting of halogen, $C_{1-6}$ alkyl, $C_{2-6}$ alkenyl, $C_{2-6}$ alkynyl, $C_{3-6}$ cycloalkyl, aryl, —OR$_5$, —CN, —NO$_2$, —NR$_5$R$_6$, —COOR$_5$, —COR$_5$, —CONHR$_5$, and —CN;
and
each of $R_5$ and $R_6$ is independently H or $C_{1-6}$ alkyl.

Other aspects of the present invention relate to pharmaceutical compositions and pharmaceutical delivery vehicles comprising the compound of Formula I. Other aspects of the present invention relate to methods of treatment and diagnosis that involve the administration of a compound of Formula I.

Other aspects of the present invention relate to methods of making a compound of Formula (I)

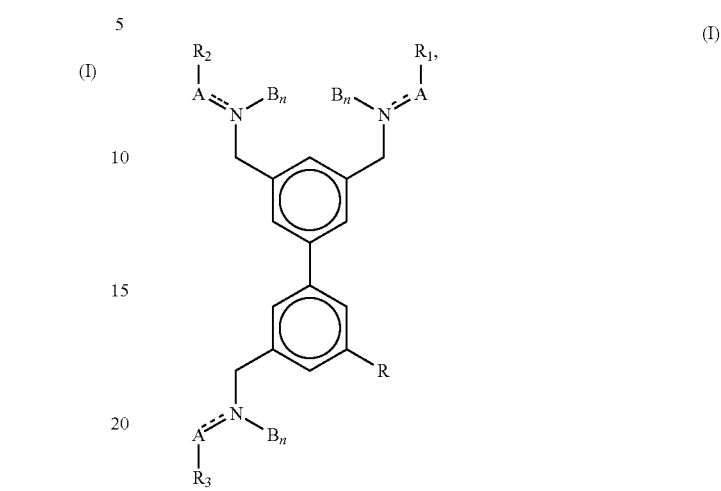

(I)

wherein
R is a targeting moiety, a tag, a pharmaceutically active moiety, a surface immobilization moiety, a moiety of Formula II

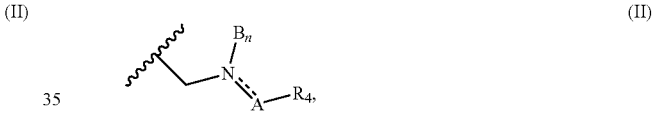

(II)

or a moiety of Formula III;

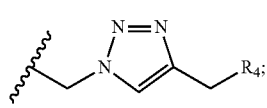

(III)

≡≡≡ is a single or a double bond;
A is selected from the group consisting of: (1) —CH$_2$—; (2) —C(O)—; and 3) =CH—;
B is H, and n is 0 or 1;
each of $R_1$, $R_2$, $R_3$, and $R_4$ is a heterocycle or a heteroaryl containing 1-5 heteroatoms selected from the group consisting of nitrogen, sulfur, and oxygen, wherein $R_1$, $R_2$, $R_3$, and $R_4$ can be the same or different;
$R_1$, $R_2$, $R_3$, and $R_4$ can be optionally substituted 1 to 4 times with substituents selected from the group consisting of halogen, $C_{1-6}$ alkyl, $C_{2-6}$ alkenyl, $C_{2-6}$ alkynyl, $C_{3-6}$ cycloalkyl, aryl, —OR$_5$, —CN, —NO$_2$, —NR$_5$R$_6$, —COOR$_5$, —COR$_5$, —CONHR$_5$, and —CN;
and
each of $R_5$ and $R_6$ is independently H or $C_{1-6}$ alkyl.

In accordance with one aspect of the present invention, the compound of Formula I above is made by providing a compound of Formula IV:

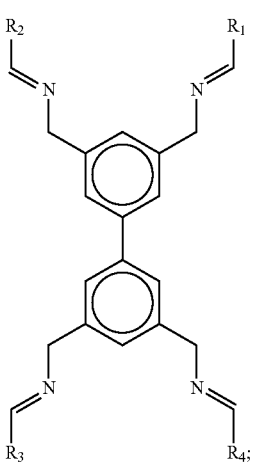

(IV)

and reacting the compound of Formula IV with a reducing agent under conditions effective to produce the compound of Formula I.

In another aspect of the present invention, the compound of Formula I is made by providing a compound of Formula IX:

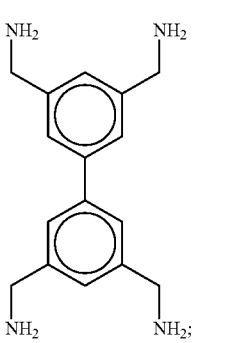

(IX)

and reacting the compound of Formula IX with a carboxylic acid or a reactive derivative thereof under conditions effective to produce the compound of Formula I.

In yet another aspect of the present invention, the compound of Formula I is made by providing a compound of Formula X:

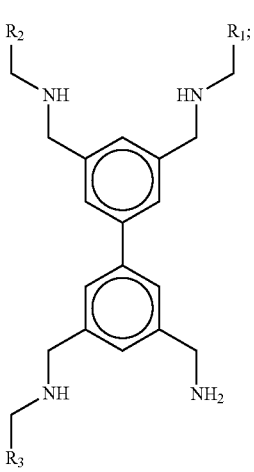

(X)

and reacting a compound of Formula X with a carboxylic acid or a reactive derivative thereof under conditions effective to produce a compound of Formula I.

To address the challenges associated with synthetic carbohydrate receptor synthesis, an alternate approach towards synthetic saccharide receptors was pursued that involves preparing a flexible host that does not possess rigid preorganization and, as a result, is capable of binding carbohydrates through pathways that arise from conformational rearrangements and positive homotropiccooperativity. Homotropiccooperativity, whereby an initial association of a target substrate induces conformational restrictions that enhance further binding of the same substrate, has been employed previously in synthetic receptors to increase binding strength and specificity towards targets such as diacids and syn-diols (Shinkai et al., *Acc. Chem. Res.* 34:494-503 (2001); Takeuchi et al., *Acc. Chem. Res.* 34:865-873 (2001); Kovbasyuk & Kramer, *Chem. Rev.* 104:3161-3187 (2004); Tabushi, *Pure Appl. Chem.* 60:581-586 (1988), which are hereby incorporated by reference in their entirety). However, synthetic receptors that utilize homotropiccooperativity remain rare (Wakabayashi et al., *Angew. Chem. Int. Ed.* 48:6667-6670 (2009); Ikeda et al., *J. Am. Chem. Soc.* 128:16008-16009 (2006); Ayabe et al., *Angew. Chem. Int. Ed.* 41:2790-2792 (2002); Sugasaki et al., *Angew. Chem. Int. Ed.* 39:3839-3842 (2000); Setsune & Watanabe, *J. Am. Chem. Soc.* 130:2404-2405 (2008); Chang et al., *Chem. Commun.* 2026-2027 (2003); Goswami et al., *New. J. Chem.* 35:2811-2819 (2011); Lusterberger et al., *Helv. Chem. Acta* 81:2190-2200 (1998); Embeyer & Rebek, *Angew. Chem. Int. Ed.* 29:1148-1150 (1990); Rebek et al., *J. Am. Chem. Soc.* 107:7481-7487 (1985); Schmuck & Geiger, *J. Am. Chem. Soc.* 127:10486-10487 (2005); Kawai et al., *J. Am. Chem. Soc.* 126:5034-5035 (2004); Huang et al., *J. Am. Chem. Soc.* 125:9272-9273 (2003); Ishi-I et al., *J. Am. Chem. Soc.* 124:14631-14641 (2002); Raker & Glass, *J. Org. Chem.* 67:6113-6116 (2002); Borovkov et al., *J. Am. Chem. Soc.* 124:2993-3006 (2001); Sugasaki et al., *J. Am. Chem. Soc.* 123:10239-10244 (2001); Sugasaki et al., *Tetrahedron* 56:4717-4723 (2000), which are hereby incorporated by reference in their entirety), and few examples exist of hosts that rely on cooperativity to enhance saccharide binding (Sugasaki et al., *Angew. Chem. Int. Ed.* 39:3839-3842 (2000); Sugasaki et al., *J. Am. Chem. Soc.* 123:10239-10244 (2001); Sugasaki et al., *Tetrahedron* 56:4717-4723 (2000), which are hereby incorporated by reference in their entirety), despite the fact that cooperativity and multivalency are ubiquitous elements of carbohydrate recognition in biology (ESSENTIALS OF GLYCOBIOLOGY (Ajit Varki et al. eds., Cold Spring Harbor Laboratory Press 1999), which is hereby incorporated by reference in its entirety). The advantages that arise with carbohydrate receptors that employ positive allosteric cooperativity include (1) shorter synthetic sequences because specificity and affinity are the direct result of allostery, (2) increased solubility associated with receptor flexibility, and (3) employing the same binding mechanisms as natural saccharide receptors could provide fundamental insights into the complex carbohydrate recognition motifs that are prevalent in nature. As described herein, a new synthetic carbohydrate receptor has been designed that contains the aminopyrrolitic groups pioneered by Roelens (Cacciarini et al., *Org. Biomol. Chem.* 9:1085-1091 (2011); Nativi et al., *J. Am. Chem. Soc.* 129:4377-4385 (2007), which are hereby incorporated by reference in their entirety), but they are appended to a flexible scaffold with eight freely rotating methylene groups and a freely rotating biphenyl bond (FIG. 1). Thus, this carbohydrate receptor is designed to dynamically explore thermodynamic and conformational space and confirm that increased receptor flexibility can induce specificity for carbohydrate guests through allostery despite a higher entropic penalty experienced in an initial association step. The synthetic carbohydrate receptor described herein achieves excellent selectivity for octylmannosides through two allosteric cooperative pathways with an overall selectivity as high as 18.9:1 α-Man: α-Gal in chloroform. Moreover, the selectivity is directly dependent on pyranoside concentration, where the receptor binds preferentially to β-Glc at low concentration (<0.3 mM), then binds α- and β-Man at higher concentrations. Accord ingly, described herein is the first synthetic carbohydrate receptor that (1) relies on cooperativity to increase selectivity and (2) whose selectivity switches with saccharide concentration.

BRIEF DESCRIPTION OF THE DRAWINGS

FIGS. 1A-1B show the chemical structure of a synthetic carbohydrate receptor 1 (also referred to herein as a compound of Formula IB) of the present invention. FIG. 1A shows the chemical structure of compound 1 and FIG. 1B shows the chemical structures of the octyl pyranosides that were evaluated for binding with compound 1. The carbon numbering scheme is also shown in FIG. 1B.

FIG. 2 shows the equilibria present in a chloroform mixture of compound 1 and β-Man at 25° C. Upon increasing the β-Man:1 ratio, $K_2$ determines the dominate species in solution. If instead, β-Man:1 decreases, $K_3$ controls the equilibrium mixture.

FIG. 3A shows $^1$H NMR (600 MHz, CDCl$_3$, 25° C.) spectra obtained after the incremental addition of a 10.4 mM solution of β-Man to a 58.6 μM solution of Compound 1 (scheme 5), with dashed lines illustrating the induced changes in chemical shifts. In FIG. 3B, the chemical shift dependences of H$^j$ of compound 1 (58.6 μM) are plotted as a function of molar equivalents of each of the eight added pyranosides from the $^1$H NMR titrations. As shown in FIG. 3C, the fittings of the H$^j$ chemical shift changes in response to the addition of β-Man to a model containing $K_1$ (dashed line) and $K_1+K_2$ (solid line).

In FIG. 5A, the intermolecular H-bonds are denoted by black dashed lines and C—H˙··π interactions are denoted by orange dashed lines. Three H-bonds occur between the hydroxyl group of C2 and both amino H$^e$ and one pyrrole H$^k$ protons of the receptor. Additionally, a C—H˙··π interaction between the phenyl ring and H$^4$ and two more H-bonds between the hydroxyl group of C3 and an amino H$^e$ and pyrrole H$^k$ proton of the receptor were observed. Side views, parallel (FIG. 5B) and perpendicular (FIG. 5C) to the biphenyl linkage of the energy minimized structure (DFT, B3LYP/6-31+(d)) for $C_2$ symmetrical 1:β-Man$_2$. The biphenyl dihedral is denoted by p.

FIG. 7A is the portion of the spectra corresponding to a CDCl$_3$ solution of β-Man (1.0 mM) with 0.50 molar equivalents of compound 1 at 600 MHz, 25° C., and with a 600 ms mixing time, and FIG. 7B corresponds to a CDCl$_3$ solution of β-Man (6.0 mM) with 2.0 molar equivalents of compound 1 at 400 MHz, −10° C., and with a 500 ms mixing time.

FIG. 10A is a $^1$HNMR of Compound 3 (500 Mhz, 25° C.) in CDCl$_3$. FIG. 10B is a 13C NMR of Compound 3 (100 MHz, 25° C.) in CDCl$_3$. FIG. 10C shows the HRMS data for intermediate compound 3.

FIG. 11A is a $^1$H NMR of compound 4 (400 MHz, 25° C.) in CDCl3. FIG. 11B is a $^{13}$C NMR of compound 4 (100 MHz, 25° C.) in CDCl$_3$ and FIG. 11C shows the HRMS for compound 4.

FIG. 12A is a $^1$H NMR of compound 1 (400 MHz, 25° C.) in CDCl$_3$. FIG. 12B is a 13C NMR of compound 1 (100 MHz, 25° C.) in DMSO-D$_6$. FIG. 12C is a $^{13}$C DEPT-135 NMR of 1 (100 MHz, 25° C.) in DMSO-D$_6$. FIG. 12D shows the HRMS of compound 1.

FIGS. 15A-15K are tables showing $^1$H NMR (600 MHz) chemical shift data for a solution of compound 1 (Scheme 5) in CDCl$_3$ upon incremental addition of various octyl pyranosides. The table of FIG. 15A shows $^1$H NMR (600 MHz, 25° C.) chemical shifts (ppm) of a 60 μM solution of 1 [H] in CDCl$_3$ upon incremental addition of β-Glc [G]. The table of FIG. 15B shows $^1$H NMR (600 MHz, 25° C.) chemical shifts (ppm) of a 50 μM solution of 1 [H] in CDCl$_3$ upon incremental addition of β-Gal [G]. The table of FIG. 15C shows $^1$H NMR (600 MHz, 25° C.) chemical shifts (ppm) of a 60 μM solution of 1 [H] in CDCl$_3$ upon incremental addition of β-GlcNAc [G]. The table of FIG. 15D shows 1H NMR (600 MHz, 25° C.) chemical shifts (ppm) of a 60 μM solution of 1 [H] in CDCl$_3$ upon incremental addition of α-Glc [G]. The table of FIG. 15E shows $^1$H NMR (600 MHz, 25° C.) chemical shifts (ppm) of a 60 μM solution of 1 [H] in CDCl$_3$ upon incremental addition of α-GlcNAc [G]. The table of FIG. 15F shows $^1$H NMR (600 MHz, 25° C.) chemical shifts (ppm) of a 60 μM solution of 1 [H] in CDCl$_3$ upon incremental addition of α-Gal [G]. The table of FIG. 15G shows $^1$H NMR (600 MHz, 25° C.) chemical shifts (ppm) of a 60 μM solution of 1 [H] in CDCl$_3$ upon incremental addition of α-Man [G]. The table of FIG. 15H shows $^1$H NMR (600 MHz, 25° C.) chemical shifts (ppm) of a 60 μM solution of 1 [H] in CDCl$_3$ upon incremental addition of β-Man [G]. The table of FIG. 15I shows $^1$H NMR (600 MHz, 20° C.) chemical shifts (ppm) of a 0.06 mM solution of 1 [H] in CDCl$_3$ upon incremental addition of β-Man [G]. The table of FIG. 15J shows $^1$H NMR (600 MHz, 15° C.) chemical shifts (ppm) of a 0.06 mM solution of 1 [H] in CDCl$_3$ upon incremental addition of β-Man [G]. The table of FIG. 15K shows $^1$H NMR (600 MHz, 10° C.) chemical shifts (ppm) of a 0.06 mM solution of 1 [H] in CDCl$_3$ upon incremental addition of β-Man [G].

FIGS. 17A-17E are tables showing $^1$H NMR (500 MHz) chemical shift data for solutions of α-Glc in CDCl$_3$ upon incremental addition of compound 1 at various temperatures. The Table of FIG. 17A shows $^1$H NMR (500 MHz, 25° C.) chemical shifts (ppm) of a 1.0 mM solution of α-Glc [G] in CDCl$_3$ upon the incremental addition of mM 1 [H]. The table of FIG. 17B shows $^1$H NMR (500 MHz, 20° C.) chemical shifts (ppm) of a 1.0 mM solution of α-Glc [G] in CDCl$_3$ upon the incremental addition of mM 1 [H]. The table of FIG. 17C shows $^1$H NMR (500 MHz, 15° C.) chemical shifts (ppm) of a 1.0 mM solution of α-Glc [G] in CDCl$_3$ upon the incremental addition of 1 [H]. The table of FIG. 17D shows $^1$H NMR (500 MHz, 10° C.) chemical shifts (ppm) of a 1.0 mM solution of α-Glc [G] in CDCl$_3$ upon the incremental addition of 1 [H]. The table of FIG. 17E shows $^1$H NMR (500 MHz, 5° C.) chemical shifts (ppm) of a 1.0 mM solution of α-Glc [G] in CDCl$_3$ upon the incremental addition of 1 [H].

FIGS. 19A-19E are tables showing $^1$H NMR (800 MHz) chemical shift data for solutions of α-GlcNAc in CDCl$_3$ upon incremental addition of compound 1 (Scheme 5) at various temperatures. The table of FIG. 19A shows 1H NMR (800 MHz, 25° C.) chemical shifts (ppm) of a 1.0 mM solution of α-GlcNAc [G] in CDCl$_3$ upon the incremental addition of 1 [H]. The table of FIG. 19B shows $^1$H NMR (800 MHz, 20° C.) chemical shifts (ppm) of a 1.0 mM solution of α-GlcNAc [G] in CDCl$_3$ upon the incremental addition of 1 [H]. The table of FIG. 19C shows $^1$H NMR (800 MHz, 15° C.) chemical shifts (ppm) of a 1.0 mM solution of α-GlcNAc [G] in CDCl$_3$ upon the incremental addition of mM 1 [H]. The table of FIG. 19D shows $^1$H NMR (800 MHz, 10° C.) chemical shifts (ppm) of a 1.0 mM solution of α-GlcNAc [G] in CDCl$_3$ upon the incremental addition of 1 [H]. The table of FIG. 19E shows $^1$H NMR (800 MHz, 5° C.) chemical shifts (ppm) of a 1.0 mM solution of α-GlcNAc [G] in CDCl$_3$ upon the incremental addition of 1 [H].

FIGS. 21A-21E are tables showing $^1$H NMR (500 MHz) chemical shift data for solutions of α-Gal in CDCl$_3$ upon incremental addition of compound 1 (Scheme 5) at various temperatures. The table of FIG. 21A shows 1H NMR (500 MHz, 25° C.) chemical shifts (ppm) of a 0.684 mM solution of α-Gal [G] in CDCl$_3$ upon the incremental addition of 1 [H]. The table of FIG. 21B shows $^1$H NMR (500 MHz, 20° C.) chemical shifts (ppm) of a 0.684 mM solution of α-Gal [G] in CDCl$_3$ upon the incremental addition of 1 [H]. The table of FIG. 21C shows $^1$H NMR (500 MHz, 15° C.) chemical shifts (ppm) of a 0.684 mM solution of α-Gal [G] in CDCl$_3$ upon the incremental addition of 1 [H]. The table of FIG. 21D shows $^1$H NMR (500 MHz, 10° C.) chemical shifts (ppm) of a 0.684 mM solution of α-Gal [G] in CDCl$_3$ upon the incremental addition of 1 [H]. The table of FIG. 21E shows $^1$H NMR (500 MHz, 5° C.) chemical shifts (ppm) of a 0.684 mM solution of α-Gal [G] in CDCl$_3$ upon the incremental addition of 1 [H].

FIGS. 23A-23D are tables showing $^1$H NMR (900 MHz) chemical shift data for solutions of β-Man in CDCl$_3$ upon incremental addition of compound 1 at various temperatures. The table of FIG. 23A shows $^1$H NMR (900 MHz, 25° C.) chemical shifts (ppm) of a 1.0 mM solution of β-Man [G] in CDCl$_3$ upon the incremental addition of 1 [H]. The table of FIG. 23B shows $^1$H NMR (900 MHz, 20° C.) chemical shifts (ppm) of a 1.0 mM solution of β-Man [G] in CDCl$_3$ upon the incremental addition of 1 [H]. The table of FIG. 23C shows $^1$H NMR (900 MHz, 15° C.) chemical shifts (ppm) of a 1.0 mM solution of β-Man [G] in CDCl$_3$ upon the incremental addition of 1 [H]. The table of FIG. 23D shows $^1$H NMR (900 MHz, 10° C.) chemical shifts (ppm) of a 1.0 mM solution of β-Man [G] in CDCl$_3$ upon the incremental addition of 1 [H].

FIGS. 25A-25E are tables showing $^1$H NMR (900 MHz) chemical shift data for solutions of β-Glc in CDCl$_3$ upon incremental addition of compound 1 (Scheme 5) at various temperatures. The table of FIG. 25A shows 1H NMR (900 MHz, 25° C.) chemical shifts (ppm) of a 1.0 mM solution of β-Glc [G] in CDCl$_3$ upon the incremental addition of 1 [H]. The table of FIG. 25B shows $^1$H NMR (900 MHz, 20° C.) chemical shifts (ppm) of a 1.0 mM solution of β-Glc [G] in CDCl$_3$ upon the incremental addition of 1 [H]. The table of FIG. 25C shows $^1$H NMR (900 MHz, 15° C.) chemical shifts (ppm) of a 1.0 mM solution of β-Glc [G] in CDCl$_3$ upon the incremental addition of 1 [H]. The table of FIG. 25D shows $^1$H NMR (900 MHz, 10° C.) chemical shifts (ppm) of a 1.0 mM solution of β-Glc [G] in CDCl$_3$ upon the incremental addition of 1 [H]. The table of FIG. 25E shows $^1$H NMR (900 MHz, 5° C.) chemical shifts (ppm) of a 1.0 mM solution of β-Glc [G] in CDCl$_3$ upon the incremental addition of 1 [H].

FIGS. 27A-27C are tables showing $^1$H NMR (900 MHz) chemical shift data for solutions of β-GlcNAc in CDCl$_3$ upon incremental addition of compound 1 (Scheme 5) at various temperatures. The table of FIG. 27A shows 1H NMR (900 MHz, 25° C.) chemical shifts (ppm) of a 1.0 mM solution of β-GlcNAc [G] in CDCl$_3$ upon the incremental addition of 1 [H]. The table of FIG. 27B shows $^1$H NMR (900 MHz, 20° C.) chemical shifts (ppm) of a 1.0 mM solution of β-GlcNAc [G] in CDCl$_3$ upon the incremental addition of 1 [H]. The table of FIG. 27C shows $^1$H NMR (900 MHz, 15° C.) chemical shifts (ppm) of a 1.0 mM solution of β-GlcNAc [G] in CDCl$_3$ upon the incremental addition of 1 [H].

FIGS. 29A-29E are tables showing $^1$H NMR (500 MHz) chemical shift data for solutions of β-Gal in CDCl$_3$ upon incremental addition of compound 1 (Scheme 5) at various temperatures. The table of FIG. 29A shows 1H NMR (500 MHz, 25° C.) chemical shifts (ppm) of a 1.0 mM solution of β-Gal [G] in CDCl$_3$ upon the incremental addition of 1 [H].

Figure 29A:
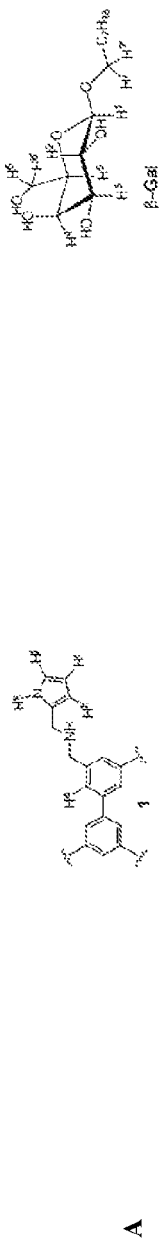
Figures 30A, 30B, 30C, 30D, 30E:
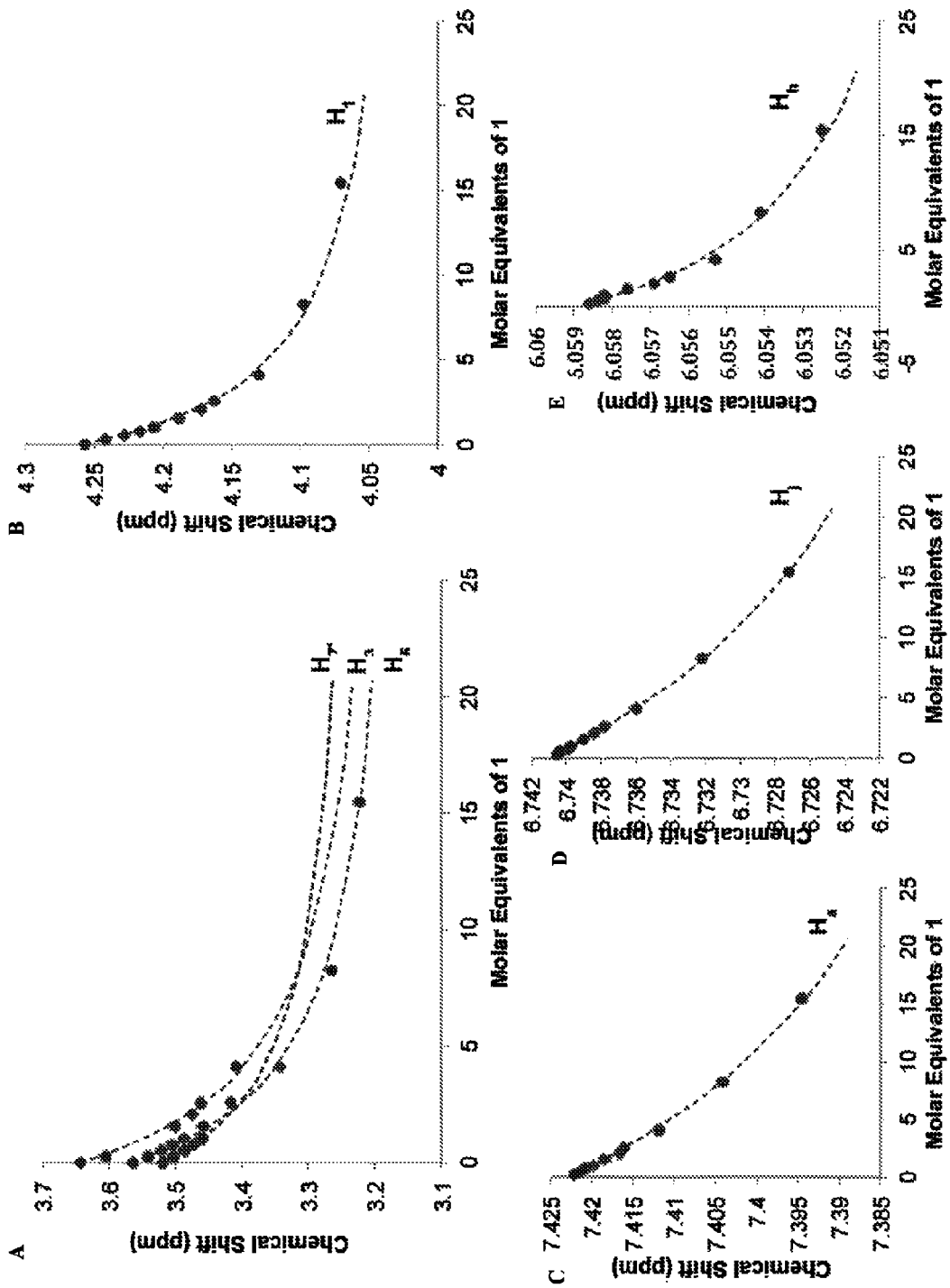

The table of FIG. 29B shows $^1$H NMR (500 MHz, 20° C.) chemical shifts (ppm) of a 1.0 mM solution of β-Gal [G] in CDCl$_3$ upon the incremental addition of 1 [H]. The table of FIG. 29C shows $^1$H NMR (500 MHz, 15° C.) chemical shifts (ppm) of a 0.684 mM solution of β-Gal [G] in CDCl$_3$ upon the incremental addition of 1 [H]. The table of FIG. 29D shows $^1$H NMR (500 MHz, 10° C.) chemical shifts (ppm) of a 0.684 mM solution of β-Gal [G] in CDCl$_3$ upon the incremental addition of 1 [H]. The table of FIG. 29E shows $^1$H NMR (500 MHz, 5° C.) chemical shifts (ppm) of a 0.684 mM solution of β-Gal [G] in CDCl$_3$ upon the incremental addition of 1 [H].

FIGS. 30A-30E are graphs fitting the experimental data (circles) with the 1:1 model (dashed line) and 2:1 model (solid line) corresponding to the $^1$H NMR titration of β-Gal with compound 1 (Scheme 5) at 25° C.

FIG. 31 is a complete table of binding constants at all temperatures observed by $^1$H NMR titrations for each pyranoside in CDCl$_3$ with compound 1 (Scheme 5).

Figure 32A:
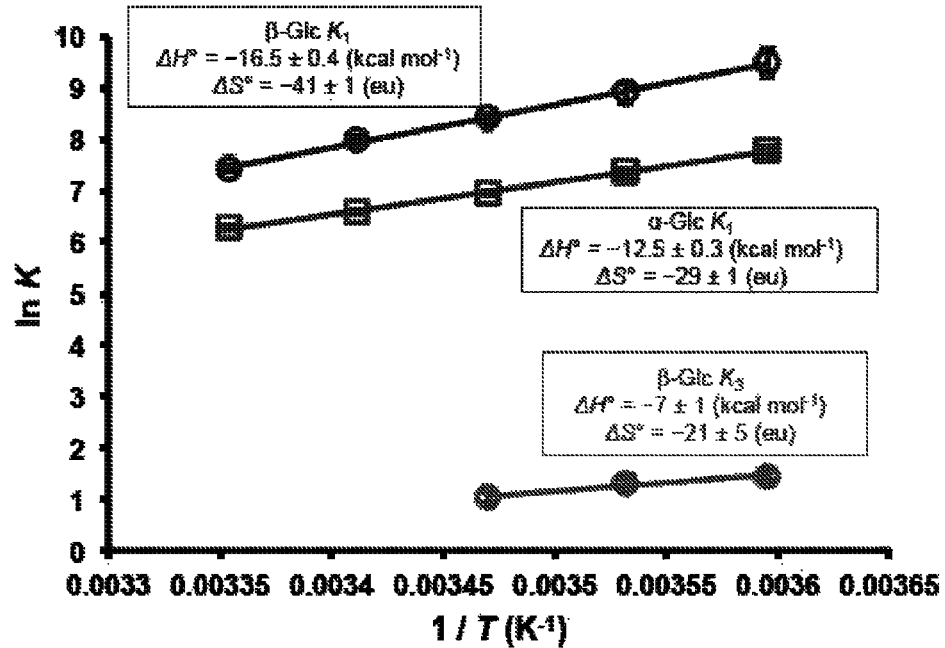
Figure 32B:
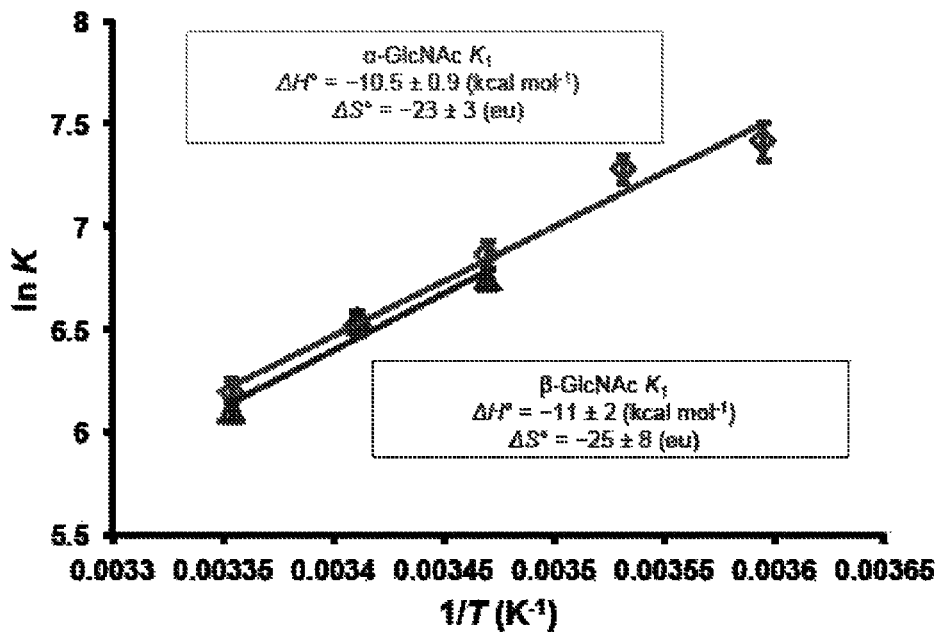
Figure 32C:
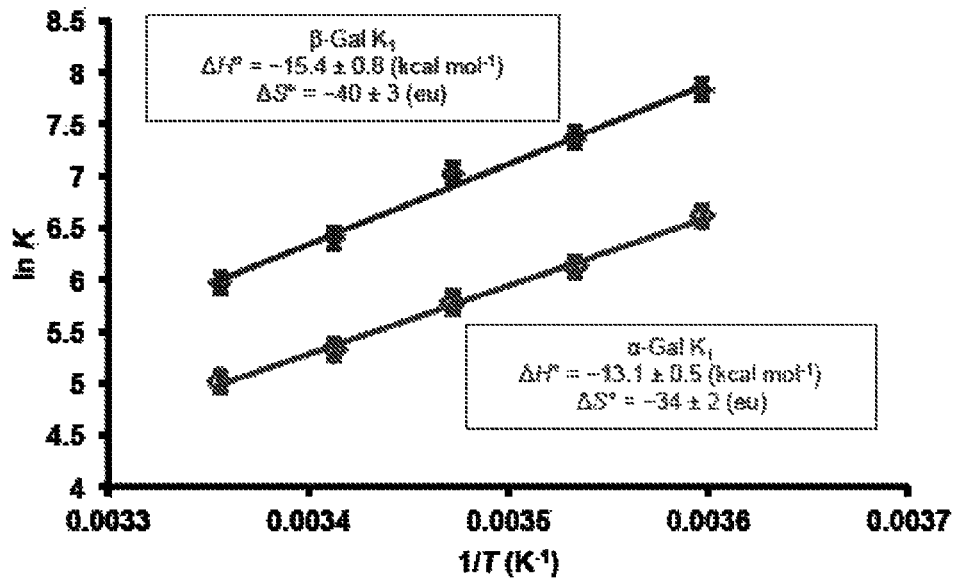
Figure 32D:
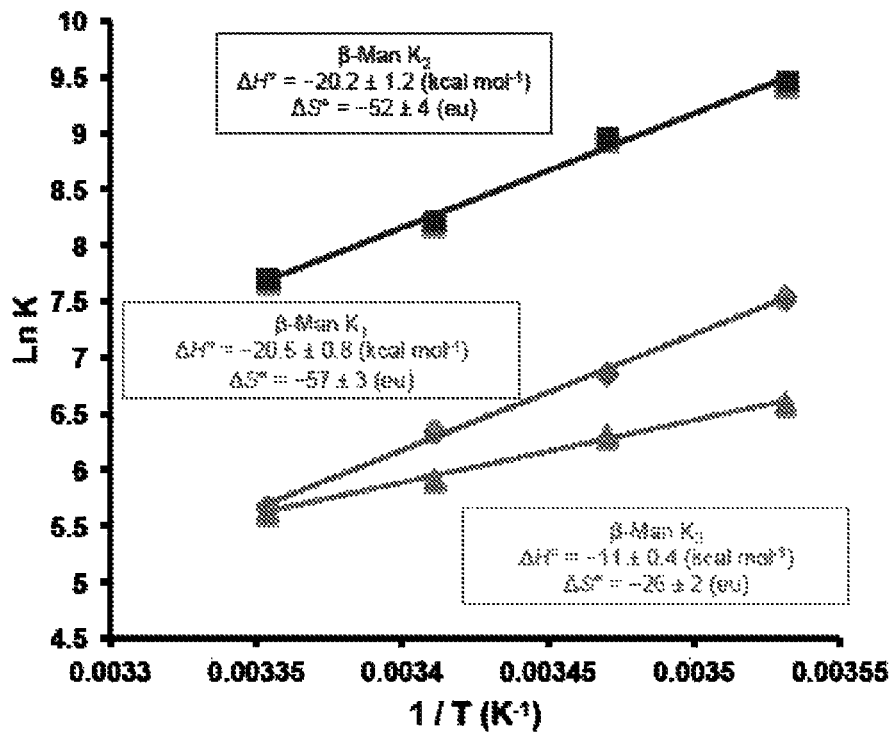

FIGS. 32A-32D are Van't Hoff Plots showing K$_1$ and K$_3$ of β-Glc and α-Glc binding to compound 1 in CDCl$_3$ (FIG. 32A), K$_1$ of α-GlcNAc and β-GlcNAc binding to compound 1 in CDCl$_3$ (FIG. 32B), K$_1$ of α-Gal and β-Gal binding to compound 1 in CDCl$_3$ (FIG. 32C), and K$_1$, K$_2$ and K$_3$ of β-Man binding to compound 1 in CDCl$_3$ (FIG. 32D).

Figure 33:
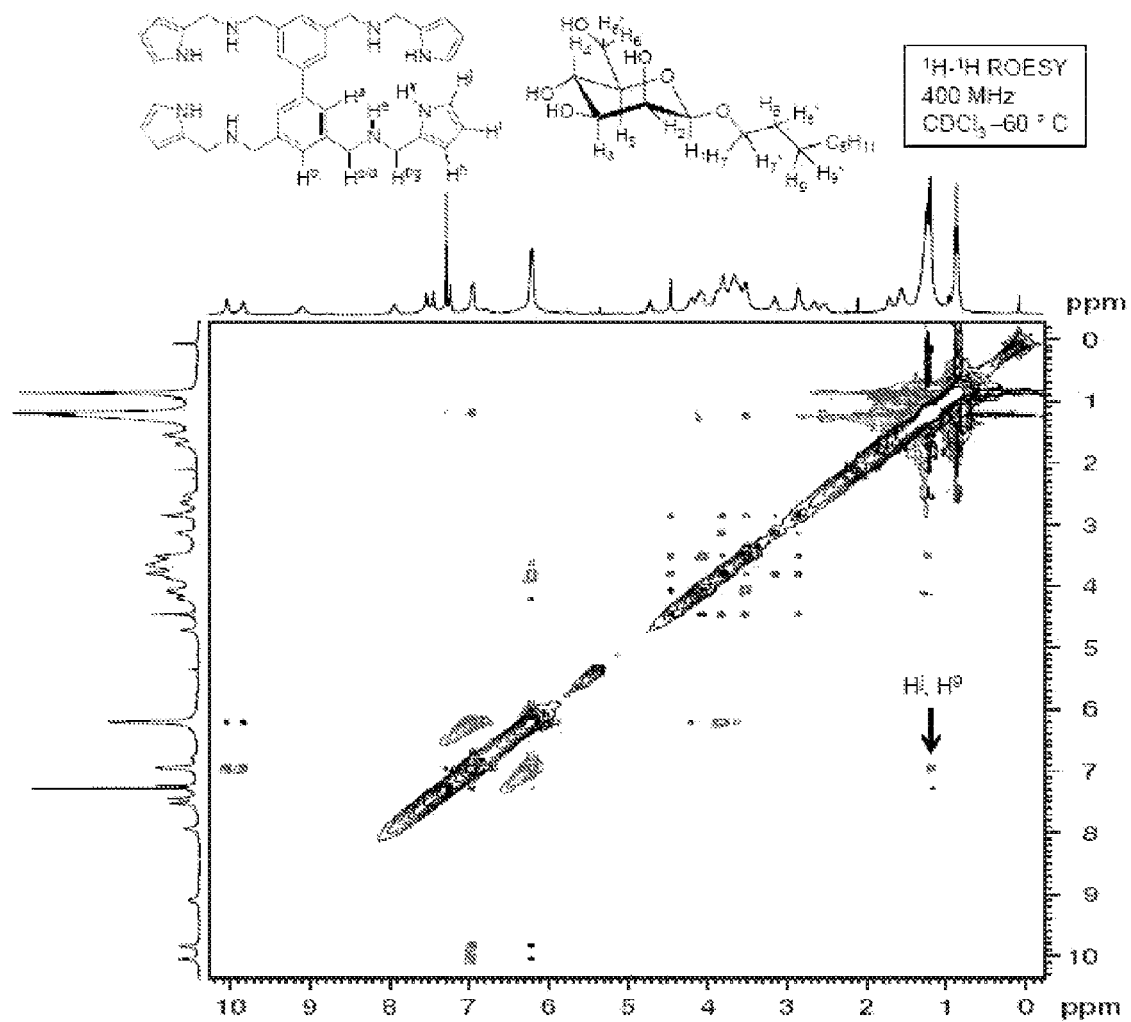

FIG. 33 shows $_1$H-$^1$H ROESY spectrum of β-Man (12.0 mM) with compound 1 (6.0 mM) at −60° C. 400 MHz in CDCl$_3$.

Figure 34:
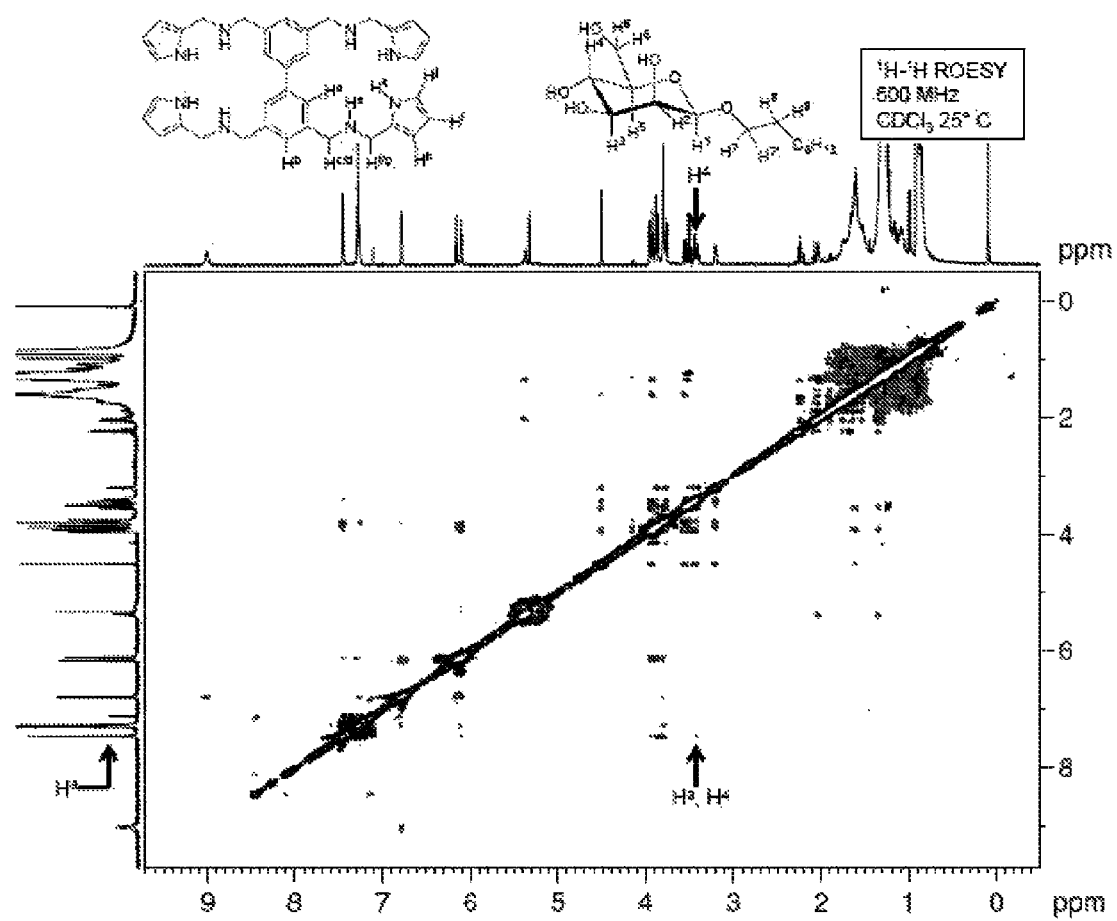

FIG. 34 shows $^1$H-$^1$H ROESY spectrum of β-Man (1.0 mM) with 1 (0.5 M) at 25° C. 600 MHz in CDCl$_3$.

FIG. 35 is a table showing complexation induced shifts for each observable pyranoside proton obtained from $^1$H NMR titrations. The observed intermolecular cross-peaks obtained from a $^1$H-$^1$H ROESY analysis. The corresponding distance between the protons in the calculated structures is indicated in parenthesis.

Figure 36:
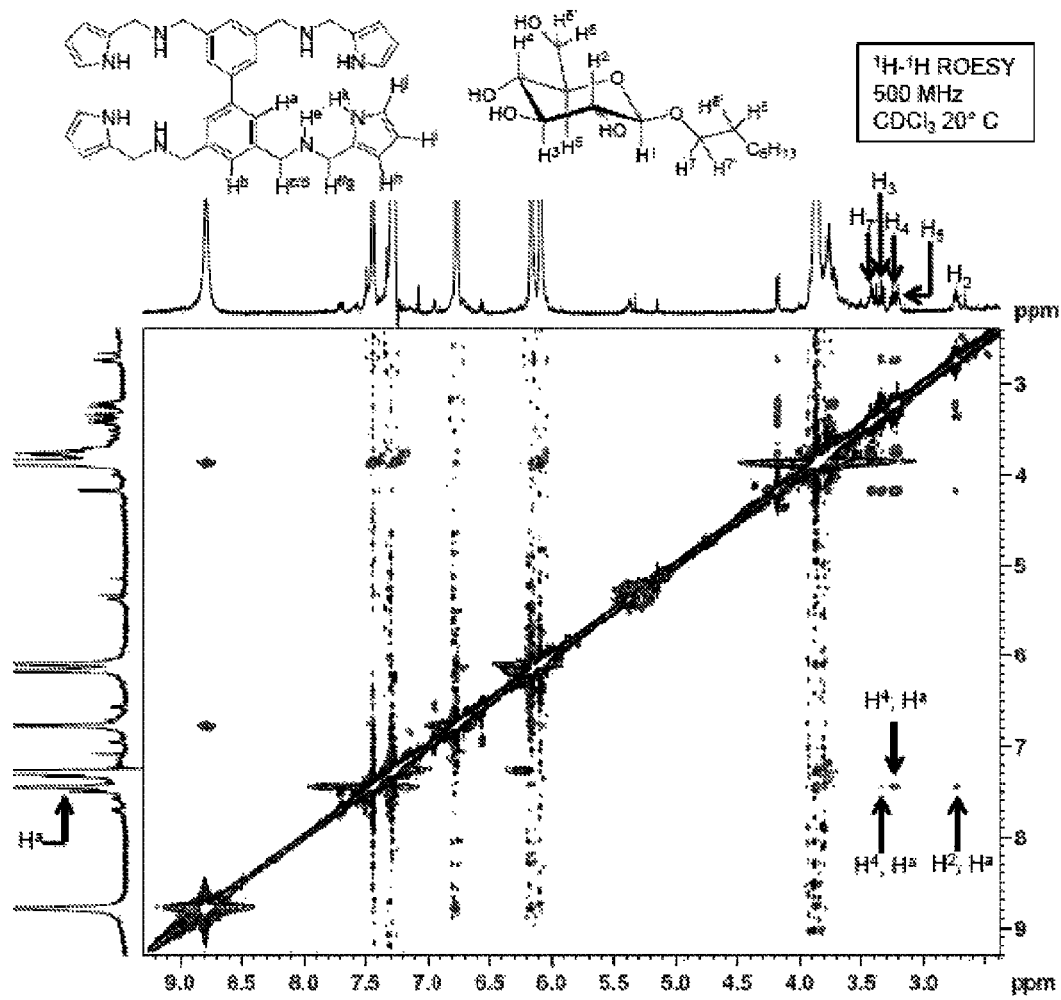

FIG. 36 shows $^1$H-$^1$H ROESY spectrum of β-Glc (1.0 mM) and 1 (3.0 mM) at 20° C. 500 MHz in CDCl$_3$.

DETAILED DESCRIPTION OF THE INVENTION

The present invention is generally directed to a new class of synthetic carbohydrate receptor compounds. Accordingly, a first aspect of the present invention is directed to a compound comprising Formula I:

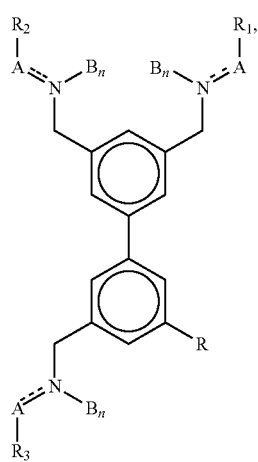

(I)

wherein
R is a targeting moiety, a tag, a pharmaceutically active moiety, a surface, immobilization moiety, a moiety of Formula II

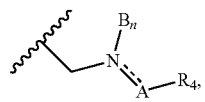

(II)

or a moiety of Formula III;

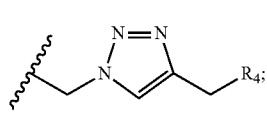

(III)

≡≡≡ is a single or a double bond;
A is selected from the group consisting of: (1) —CH$_2$—; (2) —C(O)—; and 3) =CH—;
B is H, and n is 0 or 1;
each of R$_1$, R$_2$, R$_3$, and R$_4$ is a heterocycle or a heteroaryl containing 1-5 heteroatoms selected from the group consisting of nitrogen, sulfur, and oxygen, wherein R$_1$, R$_2$, R$_3$, and R$_4$ can be the same or different;
R$_1$, R$_2$, R$_3$, and R$_4$ can be optionally substituted 1 to 4 times with substituents selected from the group consisting of halogen, C$_{1-6}$ alkyl, C$_{2-6}$ alkenyl, C$_{2-6}$ alkynyl, C$_{3-6}$ cycloalkyl, aryl, —OR$_5$, —CN, —NO$_2$, —NR$_5$R$_6$, —COOR$_5$, —COR$_5$, —CONHR$_5$, and —CN;
and
each of R$_5$ and R$_6$ is independently H or C$_{1-6}$ alkyl.

As used above, and throughout the description of the present invention, the following terms, unless otherwise indicated, shall be understood to have the following meanings. If not defined otherwise herein, all technical and scientific terms used herein have the same meaning as is commonly understood by one of ordinary skill in the art to which this invention belongs.

The term "heterocycle" refers to a stable 3- to 18-membered ring which consists of carbon atoms and from one to five heteroatoms selected from the group consisting of nitrogen, oxygen, and sulfur. The heterocycle may be a monocyclic, or a polycyclic ring system, which may include fused, bridged, or spiro ring systems; and the nitrogen, carbon, or sulfur atoms in the heterocycle may be optionally oxidized, the nitrogen atom may be optionally quaternized, and the ring may be partially or fully saturated. Examples of such "heterocycle" groups include, without limitation, azepinyl, azocanyl, pyranyl, dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiomorpholinyl, thiomorpholinyl sulfoxide, and thiomorpholinyl sulfone. Unless otherwise noted, the heterocycle is attached to its pendant group at any heteroatom or carbon atom that results in a stable structure.

The term "heteroaryl" means an aromatic monocyclic or multi-cyclic ring system of about 5 to about 14 ring atoms, or about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include, without limitation, pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like. Additional heteroaryls that are also encompassed by the present invention are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

As used herein, the term "halo" or "halogen" means fluoro, chloro, bromo, or iodo.

The term "alkyl" means an aliphatic hydrocarbon group which may be straight or branched having about 1 to about 6 carbon atoms in the chain (or the number of carbons designated by "$C_{n-n}$", where n-n is the numerical range of carbon atoms). Branched means that one or more lower alkyl groups such as methyl, ethyl or propyl are attached to a linear alkyl chain. Exemplary alkyl groups include, without limitation, methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkenyl chain. Exemplary alkenyl groups include, without limitation, ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkynyl chain. Exemplary alkynyl groups include, without limitation, ethynyl, propynyl, n-butynyl, 2-butynyl, 3-methylbutynyl, and n-pentynyl.

As used herein, "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "aryl" refers to an aromatic monocyclic or polycyclic ring system containing from 6 to 19 carbon atoms, where the ring system may be optionally substituted.

Suitable aryl groups for the substituents of the present invention, include, but are not limited to, phenyl, naphthyl, azulenyl, fluorenyl, phenanthrenyl, anthracenyl, pyrenyl, triphenylenyl, chrysenyl, and naphthacenyl. Suitable heteroaryl groups of the present invention include, but are not limited to pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolinyl, tetrahydroisoquinolinyl, cinnolinyl, quinazolinyl, quinolizilinyl, phthalazinyl, benzotriazinyl, chromenyl, and naphthyridinyl. Exemplary substituted hetroaryl include without limitation pyridyl, 2-oxo-pyridin-1-yl, pyrimidinyl, pyridazinyl, pyrazinyl, 1,2,4-triazinyl, 1,3,5-triazinyl, furanyl, pyrrolyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, tetrazolyl, indolyl, isoindolyl, benzofuranyl, benzothiophenyl, indolinyl, oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, furo[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 2-oxo-2,3-dihydro-1H-benzo[d]imidazole, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridinyl.

The term "optionally substituted" indicates that a group may have a substituent at each substitutable atom of the group (including more than one substituent on a single atom), and the identity of each substituent is independent of the others.

The term "substituted" or "substitution" means that one or more hydrogen on a designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds. By "stable compound" it is meant a compound that is sufficiently robust to survive isolation to a useful degree of purity from a reaction mixture, and formulation into an efficacious therapeutic agent. Exemplary substituents include, without limitation, oxo, thio (i.e., =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, and monocyclic.

Compounds described herein may contain one or more asymmetric centers and may thus give rise to enantiomers, diastereomers, and other stereoisomeric forms. Each chiral center may be defined, in terms of absolute stereochemistry, as (R)— or (S)—. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

As used herein "carbohydrate" is a generic term used interchangeably with sugar, saccharide, or glycan. The term includes monosaccharides, oligosaccharides, and polysaccharides as well as derivatives of these compounds. As used herein, "glycan" is a generic term for any sugars or assembly of sugars, in free form or attached to another molecule (e.g., attached to a protein). The term "sugar" is a generic term often used to refer to any carbohydrate, but most frequently to low molecular weight carbohydrates.

In accordance with this aspect of the present invention, one or more of $R_1$, $R_2$, $R_3$, and $R_4$ may comprises a substituted or unsubstituted heteroaromatic ring selected from the group of pyridine, pyrazine, pyrimidine, pyridazine, imidazole, pyrrole, oxazole, isoxazole, triazine, thiazole, isothiazole, indazole, purine, quinoline, isoquinoline, quinoxaline, quinazoline, cinnoline, acridine, benzoxazole, benzisoxazole, benzothiazole, thiophene, furan, benzofuran, benzothiophene, and oxadiazole.

One exemplary compound of the present invention is the compound of Formula IA

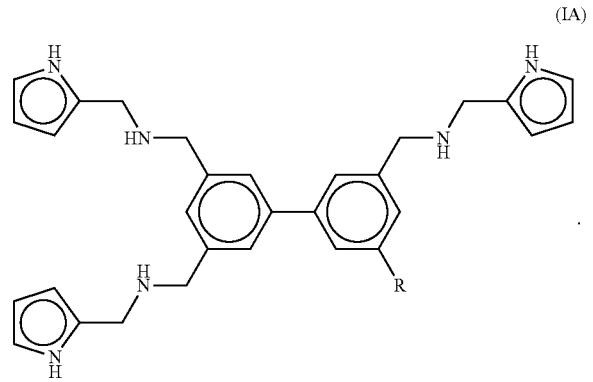

(IA)

Another exemplary compound of the present invention is the compound of Formula IB (also referred to herein as Compound 1)

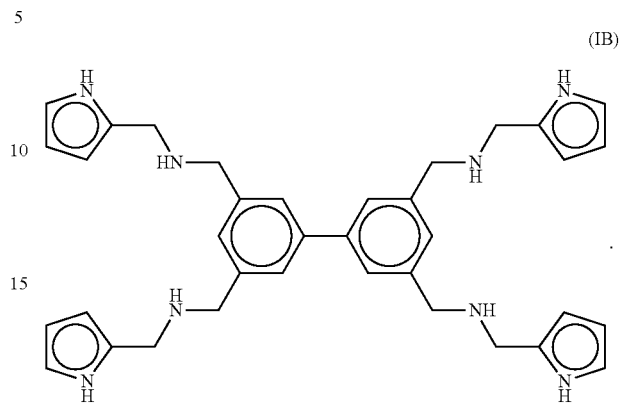

(IB)

Another exemplary compound of the present invention is the compound of Formula IC

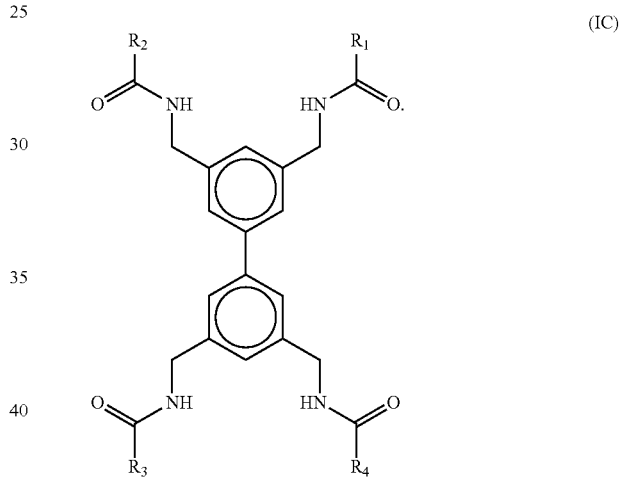

(IC)

Another exemplary compound of the present invention is the compound of Formula ID

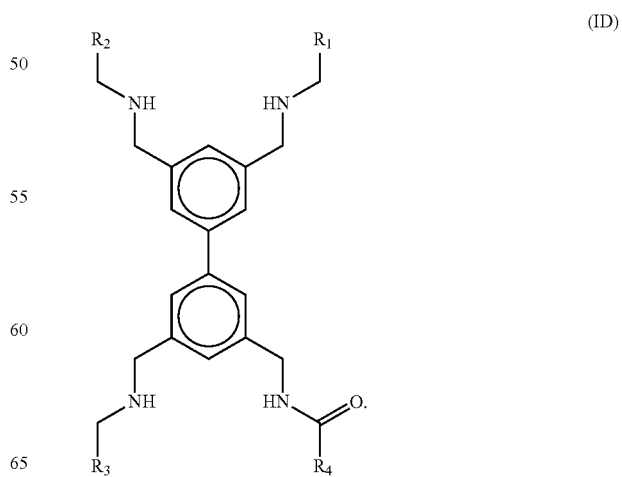

(ID)

Another exemplary compound of the present invention is the compound of Formula IE

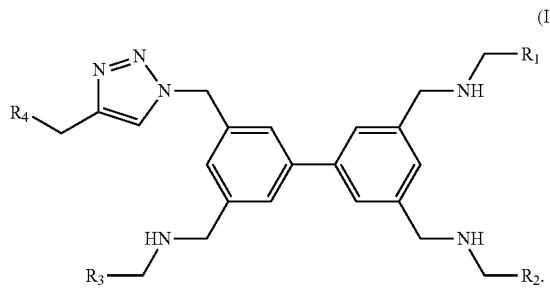

(IE)

In one embodiment of the present invention, the compound of the present invention comprises a targeting moiety. A "targeting moiety" functions to target a compound of the present invention (i.e., the synthetic carbohydrate receptor of Formula I) to a particular cell or tissue type. In one embodiment of the present invention, the targeting moiety is a signaling peptide sequence, e.g., a tissue-specific signaling peptide sequence or a cell specific signaling peptide sequence. Suitable signaling peptide sequences can include at least a portion of a ligand binding protein sequence such as high-affinity antibody fragments (e.g., Fab, Fab' and F(ab')$_2$), single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins.

Cell specific targeting of the compounds of the present invention can be achieved by targeting cell specific surface markers. For example, if the target cell is a cancer cell, the compound of the present invention may be conjugated to an anti-C3B(I) antibody as disclosed by U.S. Pat. No. 6,572,856 to Taylor et al., which is hereby incorporated by reference in its entirety. Alternatively, the compound of the present invention may be conjugated to an alphafeto protein receptor, as disclosed by U.S. Pat. No. 6,514,685 to Moro which is hereby incorporated by reference in its entirety, or to a monoclonal GAH antibody, as disclosed by U.S. Pat. No. 5,837,845 to Hosokawa, which are hereby incorporated by reference in their entirety. For targeting to a cardiac cell, the compound of the present invention may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety), cardiac troponin I, connexin-43, or any cardiac cell-surface membrane receptor that is known in the art. For targeting to a hepatic cell, the compound of the present invention may include a ligand domain specific to the hepatocyte-specific asialoglycoprotein receptor.

In another embodiment of the present invention, the compound of the present invention comprises a tag moiety. A "tag" as used herein includes any labeling moiety that facilitates the detection, quantitation, separation, and/or purification of the compounds of the present invention. Compounds of the present invention comprising a tag are particularly suitable for diagnostic and prognostic applications as described herein. Suitable tags for separation or purification, detection, and quantitation are described in more detail below.

Tags suitable for separation and/or purification include, without limitation, a poly-histidine (His$_6$-) tag, a glutathione-S-transferase (GST-) tag, or a maltose-binding protein (MBP-) tag. These tags assist in compound purification or separation but can later be removed, i.e., cleaved from the compound following recovery. Protease-specific cleavage sites can be used to facilitate the removal of the purification tag. The desired compound of the present invention can be purified further by removal of the cleaved purification tag.

Tags suitable for detection and quantitation include radioactive, fluorescent, luminescent, bioluminescent, or enzymatic tags. Suitable radioactive tags or labels include, without limitation, bismuth ($^{213}$Bi), carbon ($^{14}$C), chromium ($^{51}$Cr), gadolinium ($^{153}$Gd, $^{159}$Gd), gallium ($^{68}$Ga, $^{67}$Ga), germanium ($^{68}$Ge), holmium ($^{166}$Ho), indium ($^{11}$In, $^{113}$In, $^{112}$In, $^{111}$In), iodine ($^{131}$I, $^{125}$I, $^{123}$I, $^{121}$I), lanthanium ($^{140}$La), lutetium ($^{17}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn). Methods of radiolabeling compounds, are well known in the art, see e.g., U.S. Pat. No. 5,830,431 to Srinivasan et al., which is hereby incorporated by reference in its entirety. Radioactivity is detected and quantified using a scintillation counter or autoradiography. Suitable fluorescent tags include, without limitation, umbelliferone, fluorescein and derivatives thereof, fluorescein isothiocyanate, rhodamine and derivatives thereof, dichlorotriazinylamine fluorescein, dansyl chloride or phycoerythrin. Examples of luminescent material include, but are not limited to, luminol. Examples of bioluminescent materials include, but not limited to, luciferase, luciferin, and aequorin. The fluorescent, luminescent, and bioluminescent labels can be conjugated to the compound of the present invention using techniques disclosed in CURRENT PROTOCOLS IN IMMUNOLOGY (Coligen et al. eds., 1991), which is hereby incorporated by reference in its entirety. Fluorescence, luminescence, and bioluminescence can be detected and quantified using a fluorometer or luminometer.

Enzymatic tags generally catalyze a chemical alteration of a chromogenic substrate which can be measured using various techniques. For example, the enzyme tag may catalyze a color change in a substrate, which can be measured spectrophotometrically. Alternatively, the enzyme may alter the fluorescence or chemiluminescence of the substrate. Examples of suitable enzymatic tags include, without limitation, luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like.

In another embodiment of the present invention, the compounds of the present invention comprise a surface immobilization moiety. As used herein, a "surface immobilization moiety" is a moiety useful for attaching or coupling the compounds of the present invention to a solid surface, such as an array surface. Suitable surface immobilization moieties include, but are not limited to, alkenes, alkynes, azides, thiols, and carboxylic acids.

In another embodiment of the present invention, the compounds of the present invention comprise a pharmaceutically active moiety. The pharmaceutically active moiety can be any therapeutic agent, such as, for example, a biologic therapeutic (e.g., antibody, protein or peptide therapy, nucleic acid therapy, etc.), chemotherapeutic, radioactive agent, or small molecule.

Glycans and glycoproteins are involved in a wide variety of biological and pathological processes, including inflammation, infectious disease, cardiovascular disease, and cancer. Accordingly, the cell surface expression of glycans or glycoproteins during the aforementioned pathological processes are targeting moieties that can be used to target pharmaceutically active moieties or compounds directly to the diseased tissue or cells. For example, many cell surface glycans are considered biomarkers for various cancers. Accordingly, in one embodiment, the compounds of the present invention are suitable for delivering anti-cancer therapeutics to cancer cells expressing these glycans or glycoproteins. In accordance with this embodiment of the present invention, the compounds of the present invention are coupled to a pharmaceutically active inhibitor of cancer disease progression, such as a chemotherapeutic, an anti-angiogenic therapeutic, a stromal inhibitor, a bone-marrow derived cell inhibitor, a myeloid derived suppressor cell inhibitor, or an extracellular matrix protein inhibitor.

Suitable chemotherapeutic agents for coupling to the compounds of Formula I of the present invention include, without limitation, alkylating agents (e.g., chlorambucil, cyclophophamide, CCNU, melphalan, procarbazine, thiotepa, BCNU, and busulfan), antimetabolites (e.g., methotraxate, 6-mercaptopurine, and 5-fluorouracil), anthracyclines (e.g., daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Anti-angiogenic or anti-vasculogenic therapeutics suitable for coupling to a compound of Formula I of the present invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art and are under clinical development (see e.g., Wu et al., "Anti-Angiogenic Therapeutic Drugs for the Treatment of Human Cancer," *J Cancer Molecules* 4(2):37-45 (2008) and Bissell et al., "Why Don't We Get More Cancer?A Proposed Role of the Microenvironment in Restraining Cancer Progression," *Nat. Med.* 17(3):320-329 (2011), which are hereby incorporated by reference in their entirety). These angiogenic inhibitors include, without limitation, Endostatin (an endothelial cell proliferation and angiogenesis inhibitors), Gefitinib (an ErbB inhibitor), Lapatinib (a dual ErbB1/ErbB2 inhibitor), Erlotinib (HER1/EGFR inhibitor), Canertinib (a pan-ErbB inhibitor), Vatalanib (VEGF receptor inhibitor), Imatinib (multitargeted inhibitor of Bcr-Abl, c-kit, and PDGF-R inhibitor), Sunitinib (multi-targeted inhibitor of VEGFR, PDGFR, Kit, Flt3, Tet and CSF1R), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $\alpha_v\beta_3$ antibody).

Stromal inhibitors suitable for coupling to the compounds of Formula I of the present invention are known in the art (see Bissell et al., "Why Don't We Get More Cancer?A Proposed Role of the Microenvironment in Restraining Cancer Progression," *Nat. Med.* 17(3):320-329 (2011), which is hereby incorporated by reference in its entirety) and include, without limitation, MK-2461 (a small molecule inhibit of c-MET kinase), Anastrazole (an aromatase inhibitor), AMD070 (a CXCR4 inhibitor), IPI-926 (a hedgehog pathway inhibitor), AVE 1642 (a humanized monoclonal antibody targeting insulin-like growth factor-1 receptor), BGJ398 (a small molecule inhibitor of fibroblast growth factor receptors), Celecoxib (a COX-2 inhibitor), MK0822 (a cathepsin K inhibitor), Bortezomib (a 26S proteasome complex inhibitor), Zoledronate (a small-molecule pyrophosphate analog that inhibits the differentiation of myeloid cells and affects tumor-associated macrophages), Denosumab (a human monoclonal antibody the binds RANKL), and PG545, a heparan sulfate mimetic that inhibits heparanase activity.

Extracellular matrix protein inhibitors suitable for coupling to compounds of Formula I of the present invention include, without limitation, DX2400, an MMP-14 inhibitor, and PEGPH20, a covalently modified form of hyaluronidase which catalyzes the degradation of the extracellular matrix component hyaluroNa.

In another embodiment of the present invention, the compounds of the present invention are used to deliver an anti-inflammatory therapeutic to areas of inflammation. Suitable anti-inflammatory therapeutics that can be coupled to the compounds of Formula I include, without limitation, non-steroidal anti-inflammatory drugs (NSAID), analgesics, glucocorticoids, disease-modifying anti-rheumatic drugs, dihydrofolate reductase inhibitors (e.g., methotrexate), and biologic response modifiers.

Suitable NSAIDs include, without limitation, Cox-2 inhibitors (e.g., nimesulide, 4-hydroxynimesulide, flosulide, meloxicam, celecoxib, and Rofecoxib (Vioxx)), diclofenac, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, salsalate, sulindac and tolmetin.

Suitable analgesics for use in the present invention include, without limitation, acetaminophen, oxycodone, tramadol, and propoxyphene hydrochloride.

Suitable glucocorticoids for use in the present invention include, without limitation, cortisone, dexamethosone, hydrocortisone, methylpredisolone, prednisolone, and prednisone.

Suitable biological response modifiers, include B-cell inhibitors, such as Rituximab, or a T cell activation inhibitor such as, Leflunomide, Etanercept (Enbrel), or Infliximab (Remicade).

Suitable TNFα inhibitors include, without limitation, TNF-α antibodies (e.g., infliximab, etanercept, CytoFAb, AGT-1, afelimomab, PassTNF, and CDP-870), a matrix metalloproteinase inhibitor, a corticosteroid (e.g., mometasone, fluticasone, ciclesonide, budesonide, beclomethasone, beconase, flunisolide, deflazacort, betamethasone, methyl-prednisolone, dexamethasone, prednisolone, hydrocortisone, cortisol, triamcinolone, cortisone, corticosterone, dihydroxycortisone, beclomethasone dipropionate, and prednisone), a tetracycline TNF-α antagonist (e.g., doxycycline, minocycline, oxytetracycline, tetracycline, lymecycline, and 4-hydroxy-4-dimethylaminotetracycline), a fluoroquinolone TNF-α antagonist (e.g., norfloxacin, ofloxacin, ciprofloxacin, lomefloxacin, gatifloxacin, perfloxacin, and temafloxacin), and a quinolone TNF-α antagonist (e.g., vesnarinone and amrinone).

Another aspect of the present invention relates to a pharmaceutical composition that comprises a compound of Formula I and a pharmaceutically acceptable carrier. Acceptable pharmaceutical carriers include solutions, suspensions, emulsions, excipients, powders, or stabilizers. The carrier should be suitable for the desired mode of delivery.

In addition, the pharmaceutical composition of the present invention may further comprise one or more pharmaceutically acceptable diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

Another aspect of the present invention relates to a pharmaceutical delivery vehicle that comprises a compound of Formula I coupled to a pharmaceutically active moiety, and a pharmaceutically acceptable carrier.

Another aspect of the present invention is directed to a method of administering a pharmaceutical agent to a subject. This method involves administering to the subject, a delivery vehicle comprising a compound of Formula I coupled to the pharmaceutically active moiety of the pharmaceutical agent.

In accordance with this aspect of the present invention administration of the delivery vehicle comprising a compound of Formula I coupled to a pharmaceutical agent (i.e., a pharmaceutically active moiety) is carried out under conditions effective to deliver the pharmaceutical agent to one or more specific cells, where the one or more specific cells expresses a glycan or glycoprotein to which the compound of Formula I will bind to with high specificity.

As described supra, various glycans and glycoproteins serve as cancer biomarkers because of their high level of expression on certain cancer cells. Accordingly, the compound of Formula I, which is a carbohydrate/glycan receptor compound, can target delivery of an anti-cancer agent in a cancer cell specific manner. In one embodiment of the present invention, the glycan expressed on the cancer cell surface is a pyranose or pyranoside, e.g., mannose. Specific carbohydrates that can be targeted for anti-cancer therapy delivery through binding of the compound of Formula I of the present invention include, without limitation, galectin-1 and galectin-3 (expressed on colon cancer cells), galectin-9 (expressed on metastatic breast cancer cells), sialyl-lewisX (SLX) (expressed on pancreatic and lung cancer cells), SPan-1, TAG-72, and DU-PAN2 (expressed on pancreatic cancer cells), ST-439 (expressed on various cancer cells), carbohydrate antigen 125 (CA125) (expressed on ovarian cancer cells), CA19-9 (expressed on pancreatic, colorectal, gastric, and biliary cancer cells), CA15-3, CA27-29, and TAG 12 (expressed on breast cancer cells), and high mannose glycans (expressed on breast cancer cells). Other carbohydrate biomarkers of cancer that can be targeted for therapeutic delivery in accordance with this aspect of the invention are described in Jin et al., "Carbohydrate Recognition by Boronolectins, Small Molecules, and Lectins," *Medicinal Res. Rev.* 30(2): 171-257 (2010); Lorna et al., "High Mannose Glycans are Elevated during Breast Cancer Progression," *Mol. Cell. Proteomics* 10: 1-9 (2011); and Joo An et al., "Glycomics and Disease Markers," *Curr. Opin. Chem. Biol.* 13(5-6):601-607 (2009), which are hereby incorporated by reference in their entirety.

Another aspect of the present invention is directed to a method of detecting a carbohydrate in a sample. This method involves providing a compound of Formula I, and contacting the sample with the compound of Formula I under conditions effective for binding to occur between the compound and the carbohydrate, if present in the sample. The method further involves detecting any binding between the compound and the carbohydrate, if present in the sample.

In one embodiment of this aspect of the present invention, the carbohydrate or glycan being detected is a pyranose or pyranoside, e.g., mannose. The sample can be a serum, blood, plasma, cell, or other biological sample from a subject.

In one embodiment of this aspect of the invention, the compound of Formula I of the present invention includes a tag (e.g., a detectable label as described supra). Accordingly, detecting binding between the compound of the present invention and the carbohydrate present in the test sample is facilitated by detection of the detectable label. Detection of the carbohydrate in the sample based on binding of a tagged synthetic receptor compound of the invention can further be quantified using methods readily known to those of skill in the art. For example, when the tag is a fluorescent tag, a fluorometer can be used to quantitate the intensity of the fluorescent signal which corresponds to the concentration of the carbohydrate in the sample. Likewise, if the tag is a radiolabel, a densitometer can be used to quantitate the amount of label on an autoradiograph which corresponds to the concentration of carbohydrate in the sample.

Another aspect of the present invention relates to a method of diagnosing, in a subject, a condition characterized by a carbohydrate biomarker. This method involves obtaining a sample from the subject and contacting the sample with a compound of Formula I of the present invention. The method further involves detecting any binding between the compound of the invention and the carbohydrate in the sample, and diagnosing the condition in the subject based on the detection.

Conditions that can be diagnosed using this method of the present invention include, without limitation, inflammatory conditions, infectious diseases, cardiovascular disease, and cancer. In one embodiment of this aspect of the present invention, the condition to be diagnosed is cancer. Cancers that can be diagnosed using this method include, without limitation, colon cancer, pancreatic cancer, lung cancer, breast cancer, gastric cancer, biliary cancer, ovarian cancer, prostate cancer, and metastatic cancer. In accordance with this embodiment, the carbohydrate detected is a pyranoside, more preferably, the pyranoside is a mannose. Specific carbohydrate biomarkers of cancer that can be detected include, without limitation, galectin-1, galectin-3, galectin-9, SLX, SPan-1, DU-PAN2, ST-439, CA125, CA15-3, CA19-9, CA27-29, TAG72 and TAG12.

As described supra, using a tagged compound of Formula I of the present invention, the amount of carbohydrate that is present in the sample can be quantified. The relative concentration of carbohydrate that is detected can be used as a diagnostic or prognostic indicator for the cancerous condition.

Another aspect of the present invention is directed to a method of treating or preventing in a subject a condition mediated by a carbohydrate. This method involves selecting a subject having a condition mediated by a carbohydrate and administering to the selected subject a compound of Formula I under conditions effective for the compound to bind to the carbohydrate.

As discussed infra, cell surface expression of glycans and glycoproteins play a role in mediating inflammation, infectious disease, cardiovascular disease, and cancer. Accordingly, compounds of the present invention are particularly suitable for modulating these processes by acting as a therapeutic agent to block glycan or glycoprotein mediated cellular interactions and signaling that are involved in the progression of inflammation and disease. For example, many cell surface glycans are involved in mediating metastatic cancer cell spread. The use of the synthetic receptor compound of the present invention to inhibit or prevent glycan mediated cancer cell interactions will inhibit or prevent metastatic cancer progression.

In one embodiment of this aspect of the present invention the conditions is cancer, e.g., colon cancer, pancreatic cancer, lung cancer, breast cancer, gastric cancer, biliary cancer, ovarian cancer, and metastatic cancer. In accordance with this embodiment, the glycan bound by the compound of Formula I of the present invention is a pyranose or a pyranoside, e.g., mannose.

Another aspect of the present invention is directed to methods of making compounds of Formula I. The compounds of the present invention can be synthesized via solution phase synthesis, or alternatively solid phase synthesis using the synthetic processes described below.

In one embodiment of the present invention, compounds of Formula I are prepared in accordance with Scheme 1 as shown below.

Scheme 1

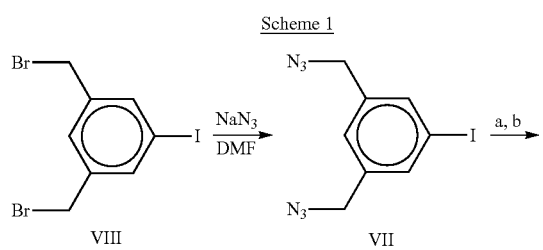

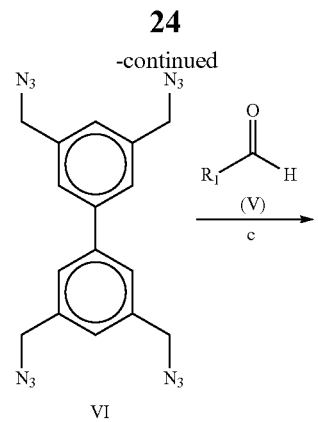

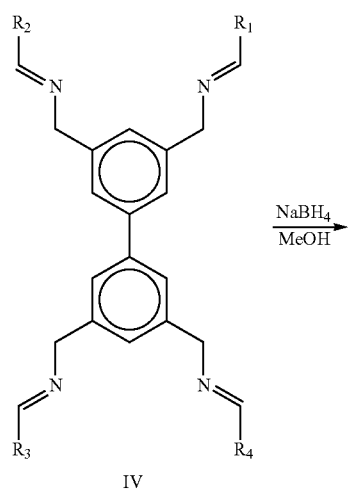

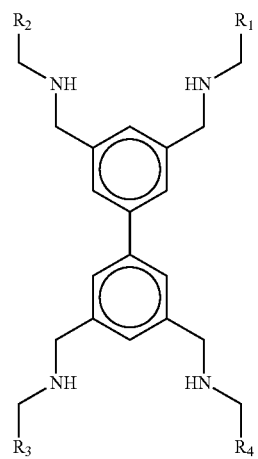

Reagents and conditions:
a) bis(pinacolato)diborane, (dppf)PdCl$_2$, K$_2$CO$_3$, DMF;
b) VII, (dppf)PdCl$_2$, Na$_2$CO$_3$;
c) PPh$_3$, C$_6$H$_6$.

In accordance with this embodiment of the present invention, the compound of Formula I can be prepared by providing a compound of Formula IV:

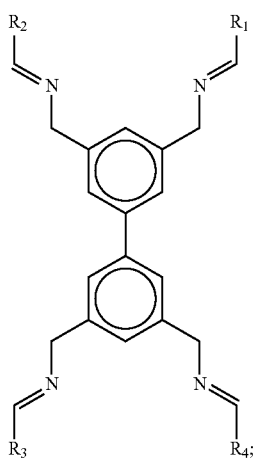

(IV)

and reacting a compound of Formula IV with a reducing agent under conditions effective to produce a compound of Formula I using methods that will be apparent to one of ordinary skill in the art. Suitable reducing agents include metal hydrides, in particular, metal borohydrides, such as sodium borohydride.

The compound of Formula IV above can be prepared by providing a compound of Formula VI:

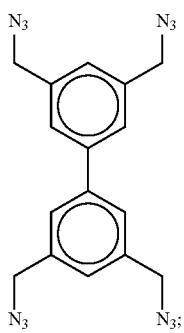

(VI)

providing an aldehyde of Formula V:

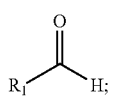

(V)

and reacting the compound of Formula V with the compound of Formula VI under conditions effective to produce a compound of Formula IV using methods that will be apparent to one of ordinary skill in the art. In accordance with this synthetic process, $R_1$, $R_2$, $R_3$, and $R_4$ of the compound of Formula IV are all the same.

The compound of Formula VI above can be prepared by providing a compound of Formula VII:

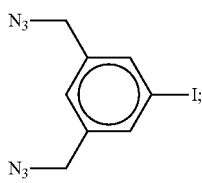

(VII)

and reacting a pair of the compound of Formula VII under conditions effective to form the compound according to Formula VI using methods that will be apparent to one of ordinary skill in the art.

The compound of Formula VII above can be prepared by providing a compound of Formula VIII:

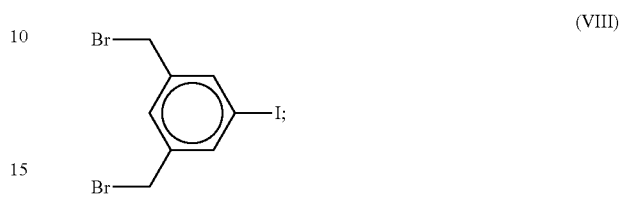

(VIII)

and reacting the compound of Formula VIII with an azide compound under conditions effective to form the compound according to Formula VII using methods that will be apparent to one of ordinary skill in the art. Suitable azide compounds for this reaction can be selected from the group consisting of sodium azide, potassium azide, cesium azide, and trimethylammonium azide.

In another embodiment of the present invention, a compound of Formula I is prepared in accordance with Scheme 2 as shown below.

Scheme 2

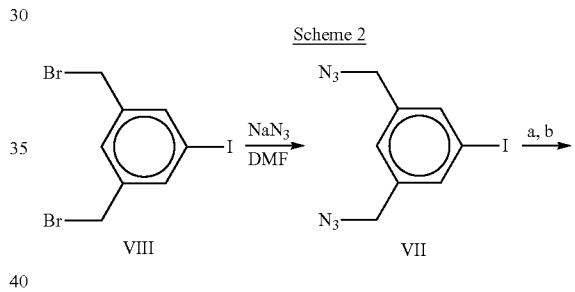

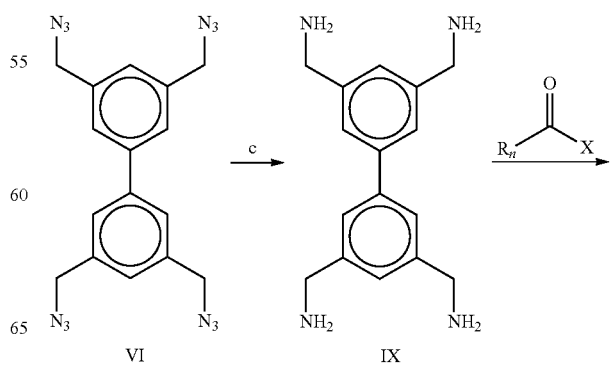

-continued

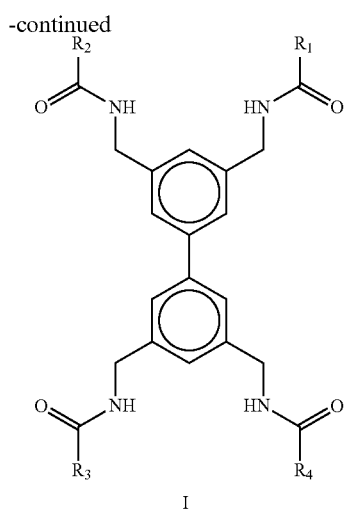

Reagents and conditions:
a) bis(pinacolato)diborane, (dppf)PdCl$_2$, K$_2$CO$_3$, DMF;
b) VII, (dppf)PdCl$_2$, Na$_2$CO$_3$;
c) PPh$_3$, H$_2$O.

In accordance with this embodiment of the present invention, compounds of Formula I can be prepared by providing a compound of Formula IX:

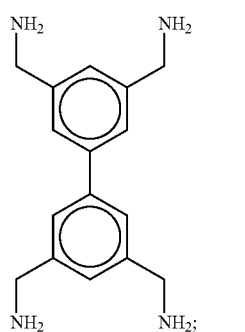

and reacting a compound of Formula IX with a carboxylic acid, or a reactive derivative thereof, under conditions effective to produce a compound of Formula I using methods that will be apparent to one of ordinary skill in the art. Suitable reactive derivatives of carboxylic acid that are suitable for reacting with a compound of Formula IX include, without limitation, activated esters, anhydrides, or acid halides (especially acid chlorides).

The compound of Formula IX above can be prepared by providing a compound of Formula VI:

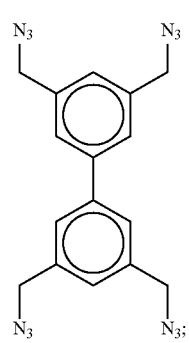

and reacting the compound of Formula VI with a reducing agent under conditions effective to produce a compound of Formula IX using methods that will be apparent to one of ordinary skill in the art. In one embodiment of the present invention, the reducing agent is triphenylphosphine.

In another embodiment of the present invention, a compound of Formula I is prepared in accordance with Scheme 3 as shown below.

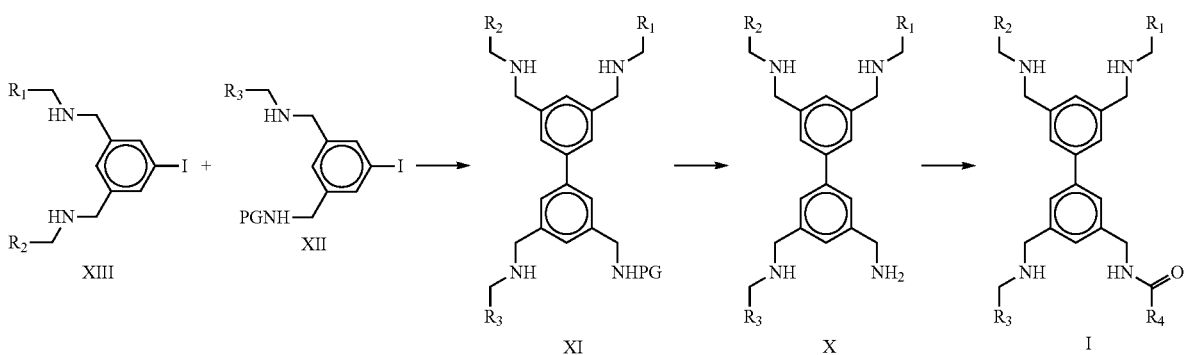
Scheme 3

-continued

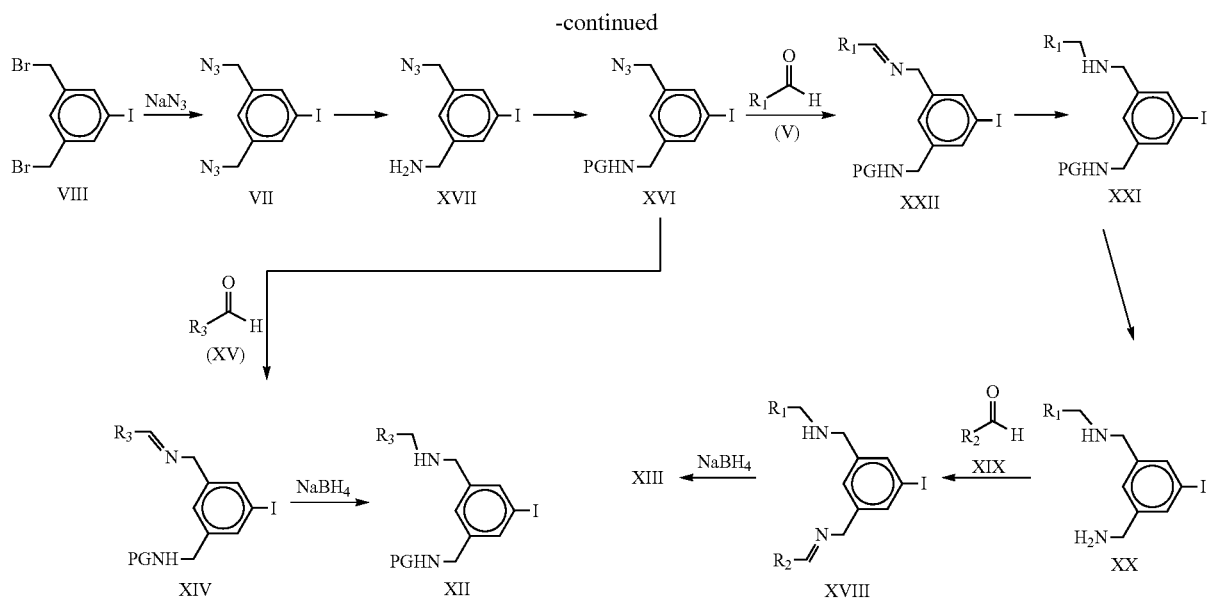

In accordance with this embodiment of the present invention, compounds of Formula I can be prepared by providing a compound of Formula X:

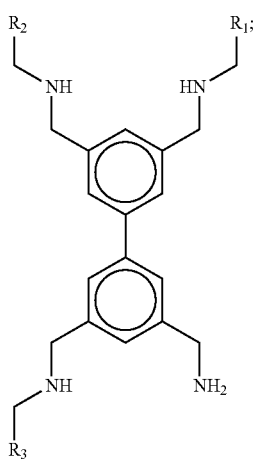

(X)

and reacting a compound of Formula X with a carboxylic acid or a reactive derivative thereof under conditions effective to produce a compound of Formula I using methods that will be apparent to one of ordinary skill in the art. As described above, suitable reactive derivatives of carboxylic acid include without limitation activated esters, anhydrides, or acid halides (especially acid chlorides).

The compound of Formula X above can be prepared by providing a compound of Formula XI:

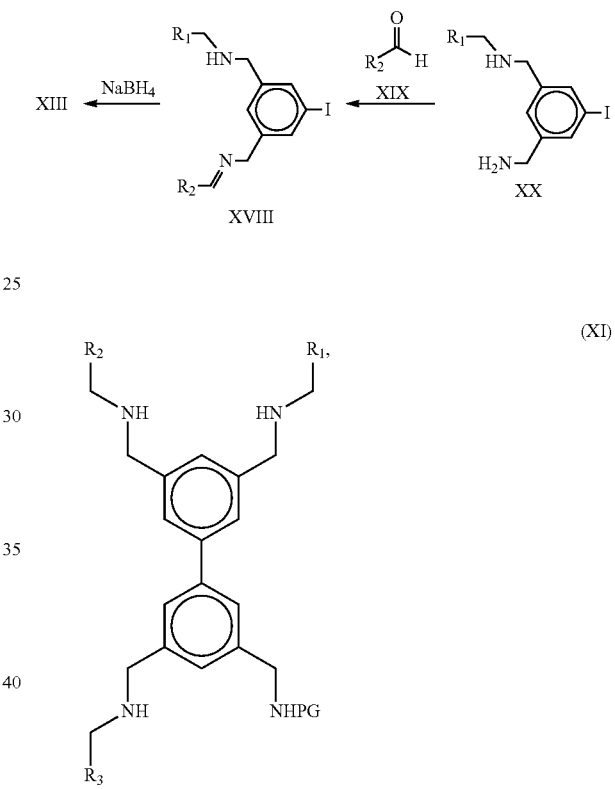

(XI)

where PG is a protecting group of an amine, and converting PG in the compound of Formula XI to hydrogen to produce a compound of Formula X using methods that will be apparent to one of ordinary skill in the art.

The protecting group is any group that is suitable for the protection of an amine. Such protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G. M. WUTS, PROTECTIVE GROUPS IN ORGANIC SYNTHESIS 494-615 (1999), which is hereby incorporated by reference in its entirety. Exemplary protecting groups for use in the synthetic methods of the present invention include, without limitation, tert-butyloxycarbonyl (Boc) and 9-Fluorenylmethyloxycarbonyl (Fmoc)

The compound of Formula XI above can be prepared by providing a compound of Formula XII:

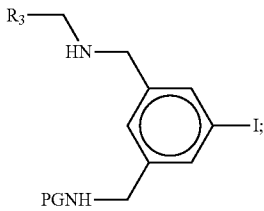
(XII)

providing a compound of Formula XIII:

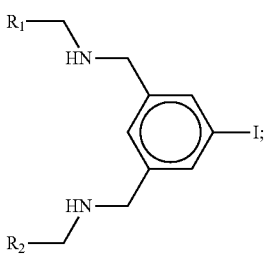
(XIII)

and reacting a compound of Formula XII with compound of Formula XIII under conditions effective to form the compound according to Formula XI using methods that will be apparent to one of ordinary skill in the art.

The compound of Formula XII above can be prepared by providing a compound of Formula XIV:

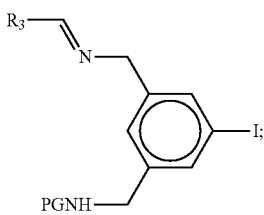
(XIV)

and reacting the compound of Formula XIV with the reducing agent under conditions effective to produce a compound of Formula XII using methods that will be apparent to one of ordinary skill in the art. Suitable reducing agents include metal hydrides, preferably, metal borohydrides. In one embodiment of the present invention, the reducing agent is sodium borohydride.

The compound of Formula XIV above can be prepared by providing a compound of Formula XVI:

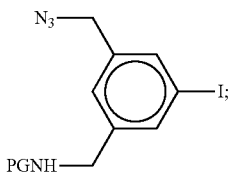
(XVI)

providing an aldehyde of Formula XV:

(XV)

and reacting the compound of Formula XVI with the compound of Formula XV under conditions effective to produce a compound of Formula XIV using methods that will be apparent to one of ordinary skill in the art.

The compound of Formula XVI above can be prepared by providing a compound of Formula XVII:

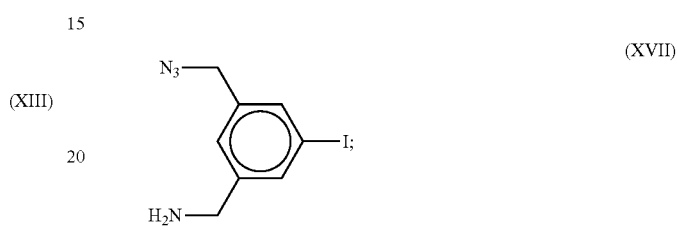
(XVII)

and reacting a compound of Formula XVII with a protecting group-introducing compound under conditions effective to form the compound according to Formula XVI. Suitable protecting group-introducing compounds include, without limitation, di-tert-buthyl dicarbonate for the introduction of BOC or fluorenyloxycarbonyl chloride for introducing Fmoc.

The compound of Formula XVII above can be prepared by providing a compound of Formula VII:

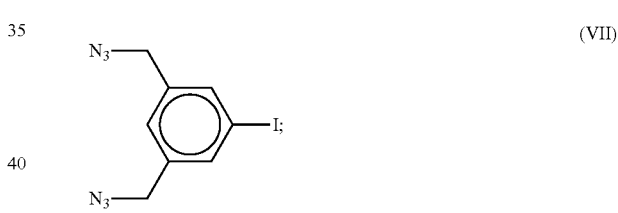
(VII)

and reacting a compound of Formula VII with 1 equivalent of a reducing agent under conditions effective to form the compound according to Formula XVII using methods that will be apparent to one of ordinary skill in the art. A suitable reducing agent for carrying out this reaction is triphenylphosphine.

The compound of Formula XIII can be prepared by providing a compound of Formula XVIII:

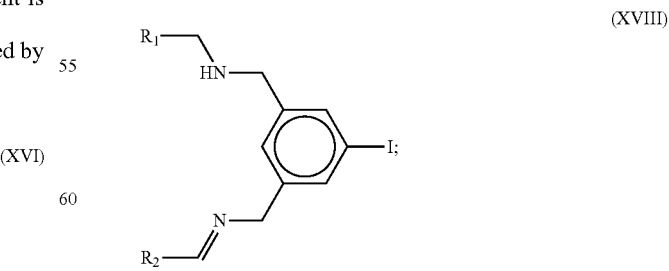
(XVIII)

and reacting the compound of Formula XVIII with the reducing agent under conditions effective to produce a compound of Formula XIII using methods that will be apparent to one of ordinary skill in the art. Suitable reducing agents include metal hydrides, preferably, metal borohydrides such as sodium borohydride.

The compound of Formula XVIII above can be prepared by providing a compound of Formula XX:

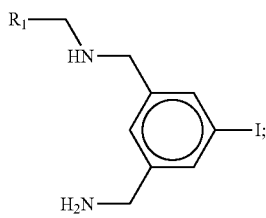

(XX)

providing an aldehyde of Formula XIX:

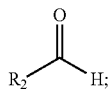

(XIX)

and reacting the compound of Formula XIX with the compound of Formula XX under conditions effective to produce a compound of Formula XVIII using methods that will be apparent to one of ordinary skill in the art.

The compound of Formula XX above can be prepared by providing a compound of Formula XXI:

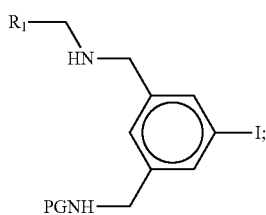

(XXI)

where PG is a protecting group of an amine, and converting PG in the compound of Formula XXI to hydrogen to produce a compound of Formula XX using methods that will be apparent to one of ordinary skill in the art. Suitable PGs include those described supra.

The compound of Formula XXI above can be prepared by providing a compound of Formula XXII:

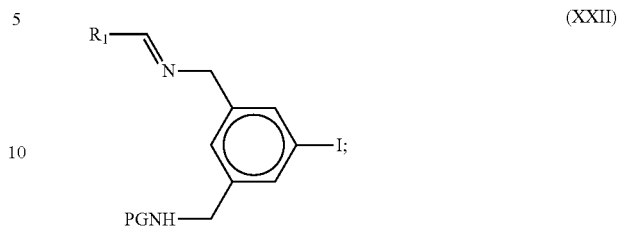

(XXII)

and reacting the compound of Formula XXII with a reducing agent under conditions effective to produce a compound of Formula XXI using methods that will be apparent to one of ordinary skill in the art. Suitable reducing agents include metal hydrides, preferably, metal borohydrides such as sodium borohydride The compound of Formula XXII can be prepared by providing a compound of Formula XVI:

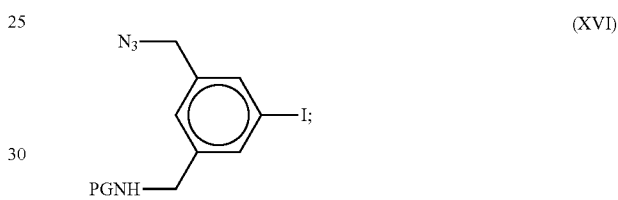

(XVI)

providing an aldehyde of Formula V:

(V)

and reacting the compound of Formula XVI with the compound of Formula V under conditions effective to produce a compound of Formula XXII using methods that will be apparent to one of ordinary skill in the art.

In another embodiment of the present invention, a compound of Formula I is prepared in accordance with Scheme 4 as shown below.

Scheme 4

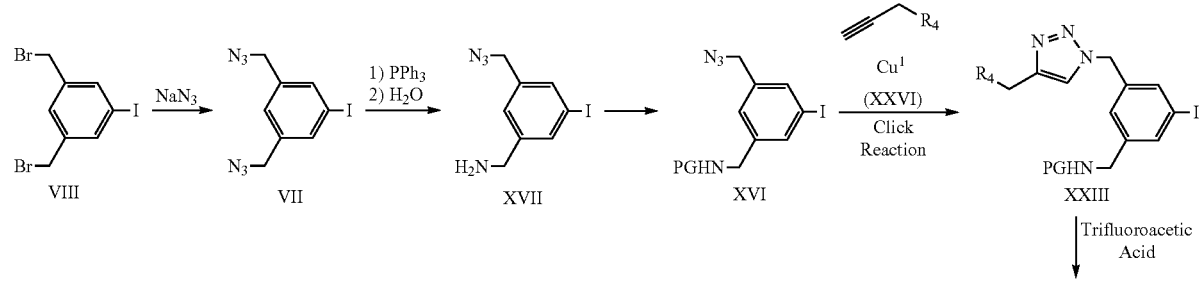

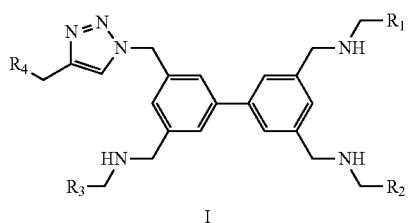

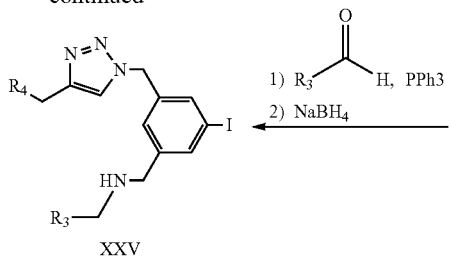

In accordance with this embodiment of the present invention, the compound of Formula I is prepared by providing a compound of Formula XXV

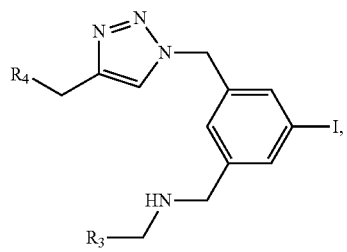
(XXV)

providing a compound of Formula XIII

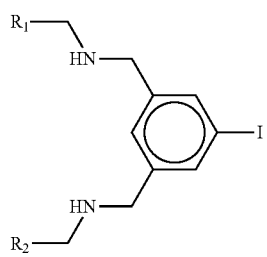
(XIII)

and reacting the compound of Formula XXV with the compound of Formula XIII under conditions effective to produce a compound of Formula I using methods that will be apparent to one of ordinary skill in the art.

The compound of Formula XXV above can be prepared by providing a compound of Formula XXIV

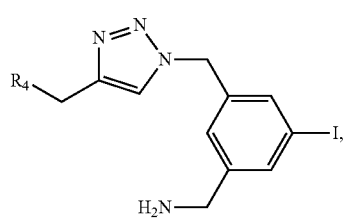
(XXIV)

providing a compound of Formula XV

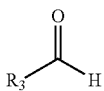
(XV)

and reacting the compound of Formula XXIV with the compound of Formula XV under conditions effective to produce a compound of Formula XXV using methods that will be apparent to one of ordinary skill in the art.

The compound of Formula XXIV above can be prepared by providing a compound of Formula XXIII

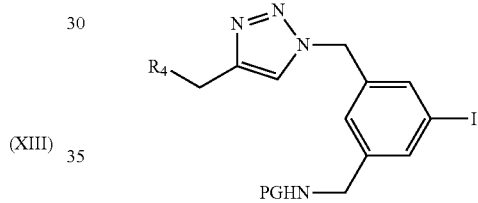
(XXIII)

where PG is a protecting group of an amine, and converting PG in the compound of Formula XXIII to hydrogen to produce a compound of Formula XXIV using methods that will be apparent to one of ordinary skill in the art. Suitable PGs include those described supra.

The compound of Formula XXIII above can be prepared by providing a compound of Formula XVI

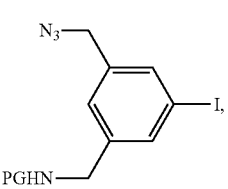
(XVI)

providing a compound of Formula XXVI

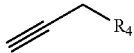
(XXVI)

and reacting the compound of Formula XVI with the compound of Formula XXVI under conditions effective to produce a compound of Formula XXIII using methods that will be apparent to one of ordinary skill in the art.

In one embodiment of the present invention, the compound of Formula XXIII is produced using click chemistry. Click chemistry techniques are well known in the art as described by Kolb et al., *Angew. Chem, Int. Ed.* 40:2004-2021 (2001); Kolb et al., *Drug Discovery Today* 8:1128-1137 (2003); Rostovtsev et al., *Angew. Chem, Int. Ed.* 41:2596-2599 (2002); Tomoe et al., *J. Organic Chem.* 67:3057-3064 (2002); Wang et al., *J. Amer. Chem. Soc.* 125:3192-3193 (2003); Lee et al., *J. Amer. Chem. Soc.* 125:9588-9589 (2003); Lewis et al., *Angew. Chem., Int. Ed.* 41:1053-1057 (2002); Manetsch et al., *J. Amer. Chem. Soc* 126:12809-12818 (2004); Mocharla et al., *Angew. Chem. Int. Ed.* 44:116-120 (2005), which are hereby incorporated by reference in their entirety). Although a number of click chemistry functional groups can be utilized, such as those described in the above references, the use of cycloaddition reactions is preferred, particularly the reaction of azides with alkynyl groups. In the presence of Cu(I) salts, terminal alkynes and azides undergo 1,3-dipolar cycloaddition forming 1,4-disubstituted 1,2,3-triazoles. In the presence of Ru(II) salts, terminal alkynes and azides undergo 1,3-dipolar cycloaddition forming 1,5-disubstituted 1,2,3-triazoles (Fokin et al., *Organic Letters* 127:15998-15999 (2005), which is hereby incorporated by reference in its entirety). Alternatively, a 1,5-disubstituted 1,2,3-triazole can be formed using azide and alkynyl reagents (Krasinski et al., *Organic Letters* 6(8):1237-1240 (2004), which is hereby incorporated by reference in its entirety). Hetero-Diels-Alder reactions or 1,3-dipolar cycloaddition reactions can also be used (Jorgensen K A, *Angew. Chem. Int. Ed.* 39:3558-3588 (2000); Tietze et al., *Top. Curr. Chem.* 189:1-120 (1997), which are hereby incorporated by reference in their entirety).

EXAMPLES

The following examples are provided to illustrate embodiments of the present invention but they are by no means intended to limit its scope.

Material and Methods for Examples 1-5

General Synthetic Methods:

All solvents were dried using a Pure Solv MD-6 solvent purification system. All reagents and starting materials were purchased from commercial sources and used without further purification unless otherwise noted. Aqueous solutions were prepared from nanopure water purified from a Milli-Q plus system (Millipore Co.), with a resistivity over 18 MΩ cm-1. Chromatography purifications were performed using Sorbent Technologies Silica Gel (60 Å, 65×250 mesh). Thin-layer chromatography (TLC) was carried out using aluminum sheets precoated with silica gel 60 (EMD 40-60 mm, 230-400 mesh with 254 nm dye). TLC plates were visualized by UV-light and stained using a p-anisaldehyde or phosphomolybdic acid solution if required. All reactions were carried out under an inert atmosphere of nitrogen using standard Schlenk techniques unless otherwise noted. Compound 2 (Rukavishnikov et al., *Tet. Lett.* 40:6353-56 (1999), which is hereby incorporated by reference in its entirety), octyl α-D-mannopyranoside (Polakova et al., *Carb. Res.* 345:1339-1347 (2010), which is hereby incorporated by reference in its entirety), and α-D-N-acetylglucosaminopyranoside (Aguilera et al., *J. Med. Chem.* 41: 4599-4606 (1998), which is hereby incorporated by reference in its entirety) were synthesized according to published literature procedures. Deuterated solvents were purchased from Cambridge Isotope Laboratories Inc. and used as received. NMR spectra were obtained on either a Bruker AVANCE 400 and 500 MHz spectrometers. All chemical shifts are reported in δ units using the solvent residual signal as an internal standard and the coupling constant values (J) are reported in Hertz (Hz). The following abbreviations are used for signal multiplicities: s, singlet; d, doublet; t, triplet; q, quartet; m, multiplet; and br, broad. Electrospray Ionization Mass Spectroscopy (ESI-MS) spectra were acquired on an Agilent LC/MSD Trap XCT system. High-resolution mass spectral analyses were carried out on an Agilent 6200 LC/MSD TOF System.

Synthesis of 1,3-Bis(azidomethyl)-5-iodobenzene (Compound 3 of Scheme 5)

Figure 10A:
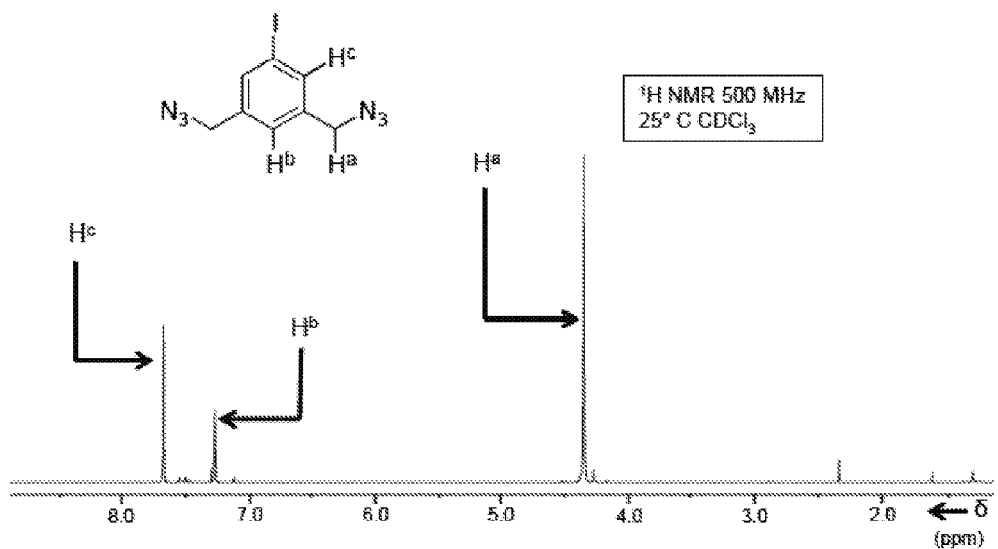
FIGS. 10A-10C show NMR and high-resolution mass spectrometry (HRMS) data for intermediate compound 3 (Scheme 5).
Figure 10B:
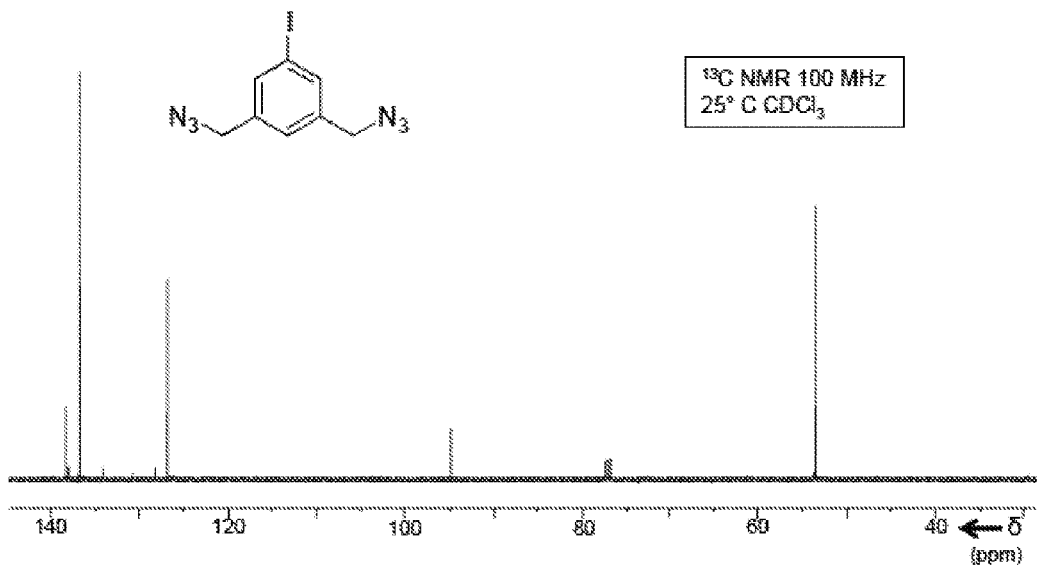
Figure 10C:
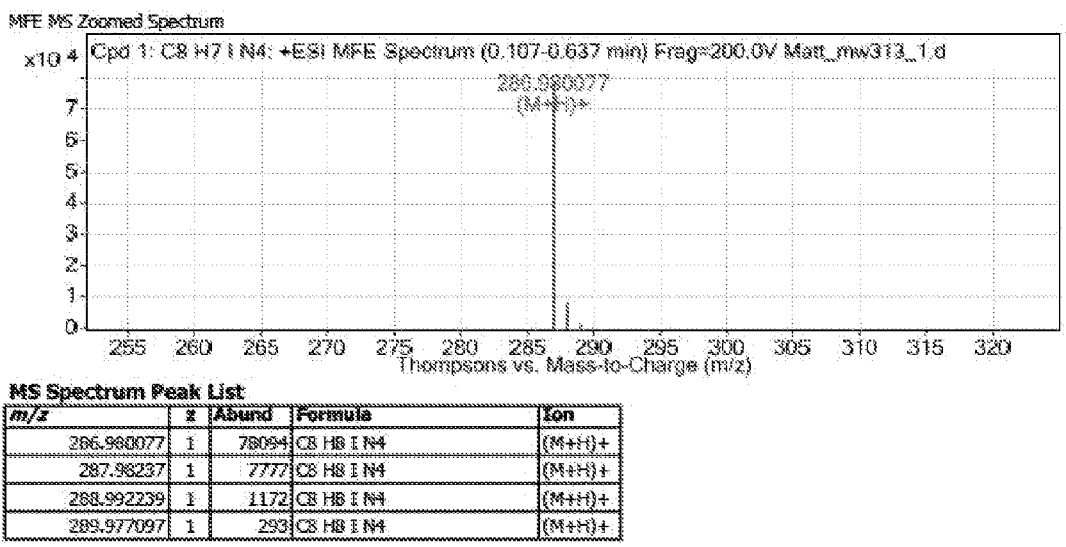

Compound 2 (1.0 g, 2.6 mmol), DMF (50 mL) and sodium azide (834 mg, 12.8 mmol) were added to a round-bottom flask, and the mixture was heated to 110° C. under $N_2$. After 16 h, the solution was cooled to room temperature, diluted with 50 mL of $CH_2Cl_2$, and stirred for an additional 2 h. The resulting mixture was filtered, and the filtrate was concentrated under reduced pressure. The resulting residue was purified by column chromatography ($SiO_2$, Hexanes) to provide 3 (701 mg, 84%) as a viscous orange oil. $^1$H NMR (400 MHz, $CDCl_3$) δ=7.65 (s, 2H), 7.24 (s, 1H), 4.33 (s, 4H). $^{13}$C NMR (100 MHz, $CDCl_3$) δ=138.15, 136.56, 126.69, 94.75, 53.55. HRMS (ESI): m/z calcd for $C_8H_8IN_4$ $[M+H-N_2]^+$ 286.9794. Found: 286.9800. NMR and high-resolution mass spectroscopy (HRMS) data is shown in FIGS. 10A-10C.

Synthesis of 3,3',5,5'-tetrakis(azidomethyl)-1,1'-biphenyl (Compound 4 of Scheme 5)

Figure 11A:
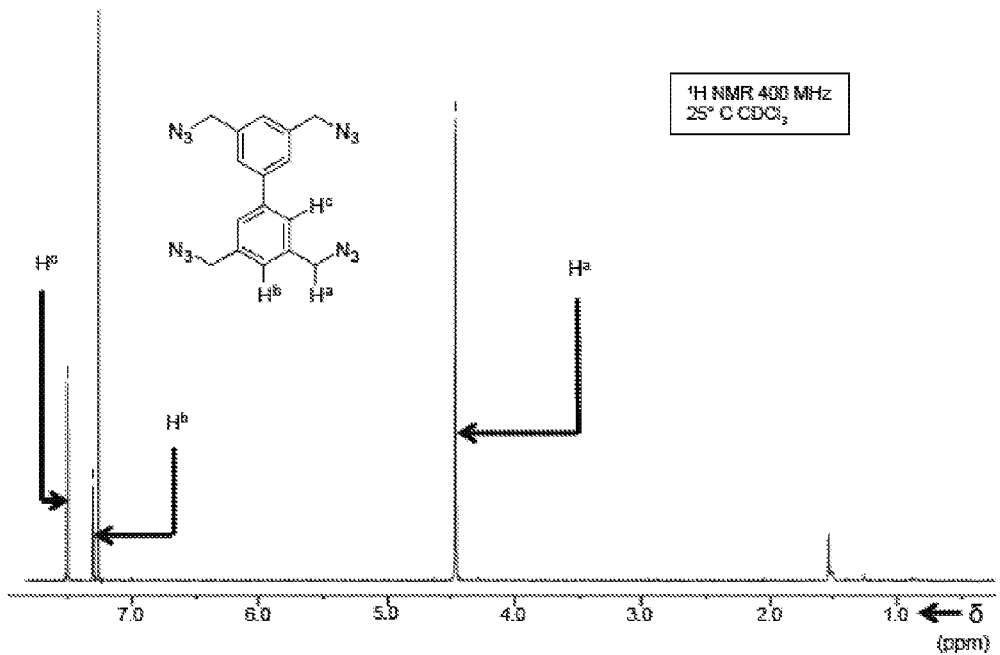
FIGS. 11A-11C show NMR and HRMS data for intermediate compound 4 (Scheme 5).
Figure 11B:
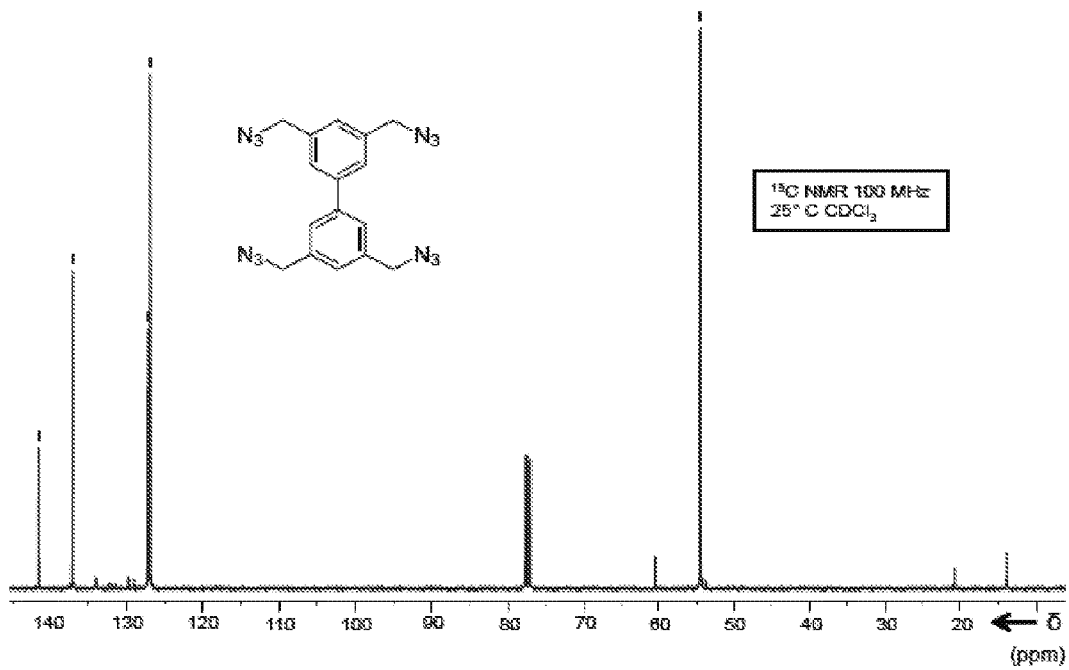
Figure 11C:
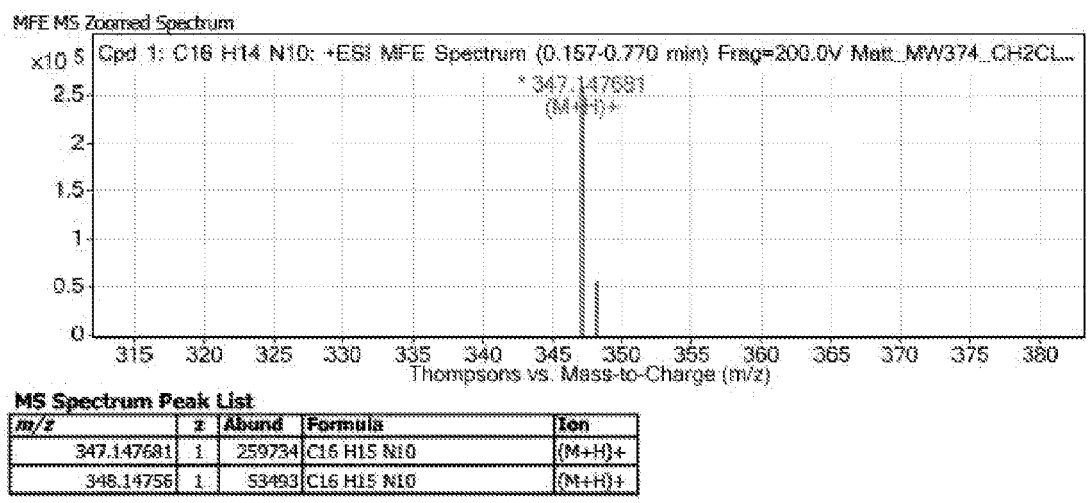
Figure 12A:
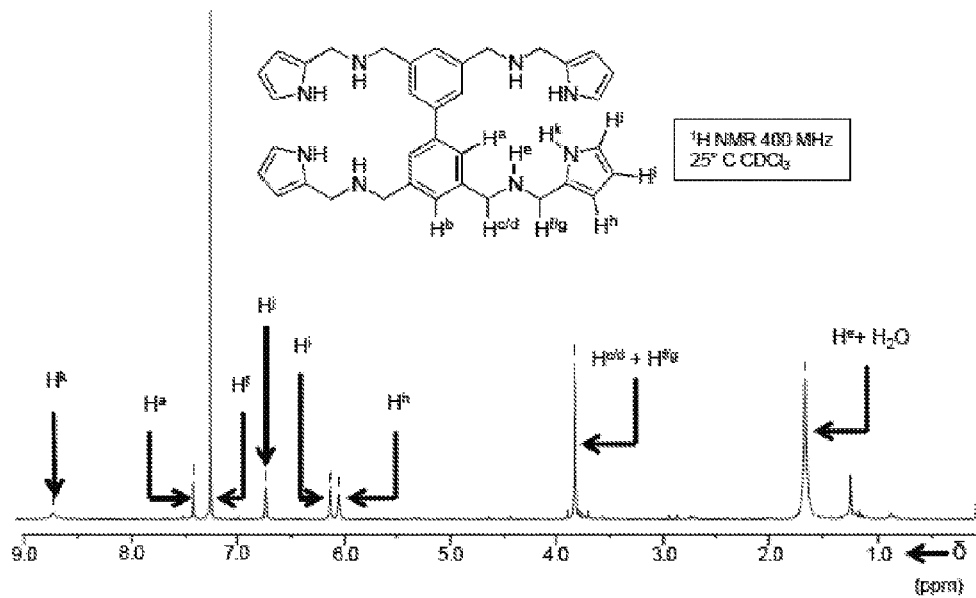
FIGS. 12A-12D show NMR and HRMS data for compound 1 (Formula IB) (Scheme 5).
Figure 12B:
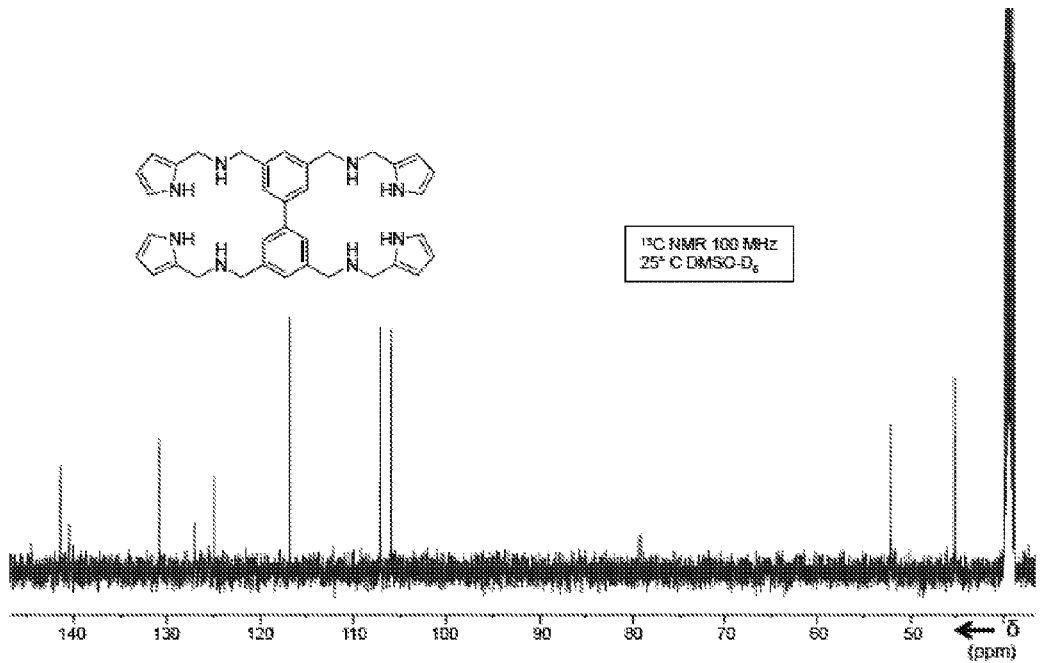
Figure 12C:
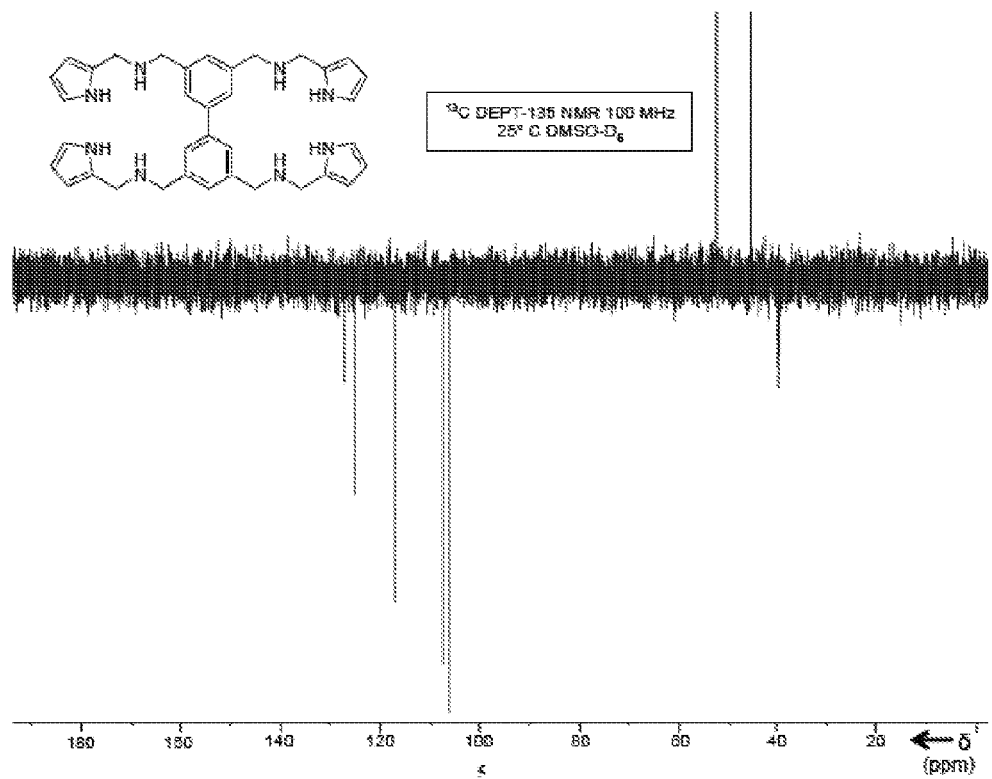
Figure 12D:
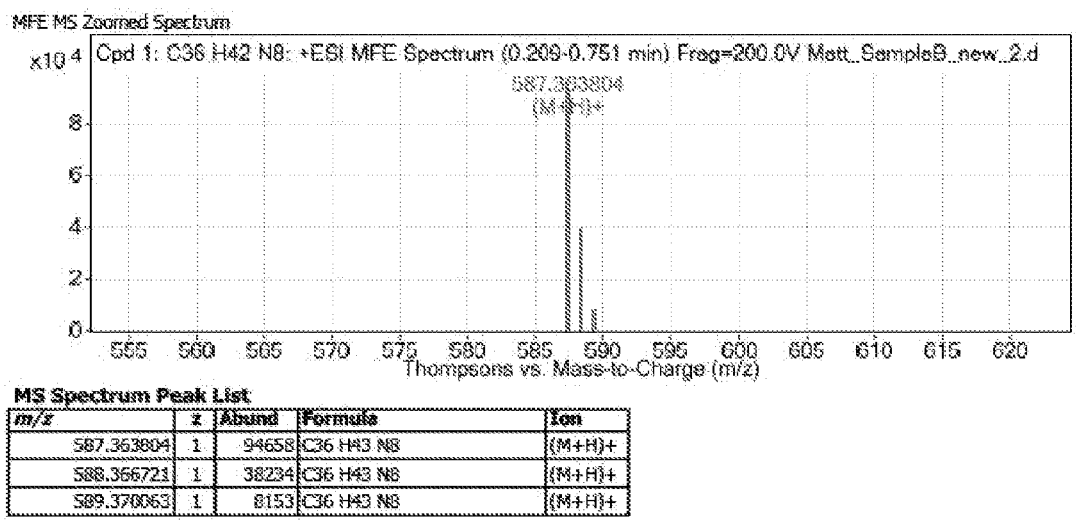

A solution of (dppf)$PdCl_2$ (650 mg, 0.89 mmol), bis-pinacolatoboron (2.50 g, 9.8 mmol), $K_2CO_3$ (2.40 g, 25.0 mmol), DMF (180 mL), and 3 (2.8 g, 8.9 mmol) were heated to 80° C. under $N_2$ and stirred for 5 h. Subsequently, DMF (60 mL), 3 (2.81 g, 8.9 mmol), (dppf)$PdCl_2$ (350 mg, 0.48 mmol), and $Na_2CO_3$ (26.3 mL, 2.0 M aq.) were added to the solution. The reaction mixture was stirred at 80° C. for 16 h, after which the mixture was diluted with water and EtOAc (60 mL 1:1), and extracted with EtOAc (3×30 mL). The organic fractions were combined, washed with brine (50 mL), dried over anhydrous $MgSO_4$, concentrated under reduced pressure, and purified by column chromatography ($SiO_2$, 1:4 EtOAc:hexanes) to yield 4 (3.16 g, 95%) as a pink oil. $^1$H NMR (400 MHz, $CDCl_3$) δ=7.50 (s, 4H), 7.30 (s, 2H), 4.46 (s, 8H). $^{13}$C NMR (100 MHz, $CDCl_3$) δ=141.46, 136.97, 127.00, 126.77, 54.46. HRMS (ESI): m/z calcd for $C_{16}H_{15}N_{10}$ $[M+H-N_2]$ 347.1481. Found: 347.1476. NMR and high-resolution mass spectroscopy (HRMS) data is shown in FIGS. 11A-11C.

Synthesis of N,N',N'N"N'"-([1,1'-biphenyl]-3,3',5,5'-tetrayltetrakis(methylene))tetrakis (1-(1H-pyrrol-2-yl)methanamine) (Compound 1 of Scheme 5)

Compound 4 (0.500 g, 1.34 mmol), PhMe (30 mL) and $PPh_3$ (1.47 g, 5.6 mmol) were heated to 90° C. and stirred for 1 h before the addition of 1H-pyrrole-2-carbaldehyde (530 mg, 5.6 mmol). The reaction mixture was stirred for 12 h at 90° C., cooled to room temperature and concentrated under reduced pressure. The resulting residue was dissolved in MeOH (30 mL) and $NaBH_4$ (304 mg, 8.04 mmol) was added to the solution over 20 min at room temperature. After stirring for 1 h, the reaction mixture was poured into water/brine (30 mL 1:1) and extracted with $CH_2Cl_2$ (4×70 mL). The organic fractions were combined, dried over anhydrous $MgSO_4$, concentrated under reduced pressure and purified by column chromatography ($SiO_2$, 9:1:1 $CH_2Cl_2$:MeOH:$NH_3$(Conc)) to provide 1 (625 mg, 80%) as a yellow solid. $^1$H NMR (CDCl$_3$, 400 MHz) δ=8.73 (s, 4H, br), 7.42 (s, 4H), 7.26 (s, 2H), 6.74 (s, 4H), 6.14 (d, 4H), 6.06 (d, 4H), 3.84 (s, 16H, br), 1.68 ppm (s, 4H, br). 13C NMR (DMSO-D$_6$, 100 MHz) δ=141.61 (CH), 140.66 (CH), 131.07 (CH), 127.27 (CH), 125.17 (CH), 117.14 (CH), 107.40 (CH), 106.22 (CH), 79.45 (CH$_2$), 52.73 (CH$_2$) ppm. HRMS (ESI): m/z calcd for C$_{36}$H$_{43}$N$_8$ [M+H]$^+$ 587.3532. Found: 587.3638. NMR and high-resolution mass spectroscopy (HRMS) data is shown in FIGS. 12A-12D.

$^1$H NMR Titrations.

$^1$H NMR titrations were performed in CDCl$_3$ at a field strength of either 500, 800, or 900 MHz at 25, 20, 15, 10, or 5° C. The $^1$H NMR resonances corresponding to both pyranoside and host were assigned through $^1$H-$^1$H COSY and NOESY experiments. The experimental temperatures were verified through calibration with a 100% methanol standard (Ammann et al., *J. Magn. Reson.* 46:319-321 (1982), which is hereby incorporated by reference in its entirety). $^1$H NMR dilution experiments to determine K$_{dimer}$ at all temperatures were accomplished through the incremental addition of a 62.5 mM solution of 1 to neat CDCl$_3$. K$_{dimer}$ values at 25, 20, 15, 10, and 5° C. were determined to be 13.0, 15.3, 16.9, 20.8, and 24.2±0.5 M$^{-1}$ respectively.

The equilibria involved in a CDCl3 mixture of β-Man and 1 are K$_{dimer}$, K$_1$, K$_2$, and K$_3$, which are expressed by the following relationships:

$$K_{dimer} = \frac{[H_2]}{[H]^2} \quad (1)$$

$$K_1 = \frac{[HG]}{[H][G]} \quad (2)$$

$$K_2 = \frac{[HG_2]}{[HG][G]} \quad (3)$$

$$K_3 = \frac{[H_2G]}{[HG][H]} \quad (4)$$

Likewise, mass balance equations relating the known total concentrations of 1 ([H]$_t$) and pyranoside ([G]$_t$) with their corresponding equilibrium concentrations can be derived:

$$[H]_t = [H] + 2[H_2] + [HG] + [HG_2] + 2[H_2G] \quad (5)$$

$$[G]_t = [G] + +[HG] + 2[HG_2] + [H_2G] \quad (6)$$

Combining equations (1) through (6) yields the following relationships:

$$[H]_t = =[H] + 2K_{dimer}[H]^2 + K_1[H][G] + K_1K_2[H][G]^2 + 2K_1K_3[H]^2[G] \quad (7)$$

$$[G]_t = [G] + K_1[H][G] + 2K_1K_2[H][G]^2 + K_1K_3[H]^2[G] \quad (8)$$

Combining equations (7) and (8) yields equation (9), which can be solved for [G] to give equation (10):

$$[G]_t - 2[H]_t = [G] - 2[H] - 4K_{dimer}[H]^2 - K_1[H][G] - 3K_1K_3[H]^2[G] \quad (9)$$

$$[G] = \frac{[G]_t - 2[H]_t + 2[H] + 4K_{dimer}[H]^2}{1 - K_1[H] - 3K_1K_3[H]^2} \quad (10)$$

Combining equations (8) and (10) gives polynomial equation (11), which, when subjected to the boundary conditions specified by equations (7) and (8), can be solved iteratively to obtain the equilibrium concentration of free host for any value of [H]$_t$, [G]$_t$, K$_{dimer}$, K$_1$, K$_2$, and K$_3$.

$$0 = (-6K_{dimer}[K_1K_3]^6)[H]^2 + (16K_{dimer}^2K_1K_2 - 8K_{dimer}K_1^2K_3 - 3[K_1K_3]^2)[H]^3 + (16K_{dimer}K_1K_2 - 4K_1^2K_3 - 2K_{dimer}K_1^2 + 3[K_1K_3]^2[H]_t - 6[K_1K_3]^2[G]_t + 4K_{dimer}K_1K_3[H]^4 + (-16K_{dimer}K_1K_2[H]_t + 8K_{dimer}K_1K_3[G]_t + 4K_1K_2 + 4K_1^2K_3[H]_t - 5K_1^2K_3[G]_t - K_1^2 - 2K_1K_3[H]^3 + (-8K_1K_2[H]_t + 4K_1K_2[G]_t + K_1^2[H]_t - K_1^2[G]_t + 2K_1K_3[H]_t + 2K_1K_3[G]_t + 2K_{dimer})[H]^2 + (-4K_1K_2[G]_t[H]_t + 4K_1K_2[H]_t^2 + K_1K_2[G]_t^2 + K_1[G]_t + 1)[H] - [H]_t \quad (11)$$

By following a similar protocol, models can be derived for other sets of equilibria, including K$_1$ and K$_2$ (Equation (12)) and K$_{dimer}$, K$_1$, and K$_3$ (Equation (13)).

$$0 = K_1K_2[G]^3 + (-K_1K_2[G]_t + K_1 + 2K_1K_2[H]_t)[G]^2 + (-K_1[G]_t + K_1[H]_t + 1)[G] - [G]_t \quad (12)$$

$$0 = 2K_{dimer}K_1K_3[H]^4 + 2(K_{dimer}K_1 + K_1K_3)[H]^3 + (K_1 + 2K_{dimer} + 2K_1K_3[G]_t - K_1K_3)[H]^2 + (1 + K_1[G]_t - K_1[H]_t)[H] - [H]_t \quad (13)$$

The addition of 1 to a CDCl$_3$ pyranoside solution or vice versa resulted in the perturbation of the chemical shifts (δ) corresponding to resonances of both 1 and pyranoside. This is the result of an exchange process involving 1 (H) and pyranoside (G) equilibria products exchanging fast on the NMR timescale, resulting in the averaging of chemical shifts of protons in differing chemical environments. Accordingly, equilibrium constants, K$_a$, can be quantified by first defining a model that includes the correct set of equilibria (see equations 12 and 13 above), calculating the hypothetical concentrations of equilibrium species and the corresponding chemical shifts, and finally fitting the resulting data to the experimental results (Thordarson, *Chem. Soc. Rev.* 40:1305-1323 (2011), which is hereby incorporated by reference in its entirety). Theoretical chemical shifts for 1 (H) and pyranoside (G) were calculated with Eq. 14 and Eq. 15.

$$\delta_{host} = \frac{[H]\delta_H + 2[H_2]\delta_{H_2} + [HG]\delta_{HG} + [HG_2]\delta_{HG_2} + 2[H_2G]\delta_{H_2G}}{[H]_t} \quad (14)$$

$$\delta_{guest} = \frac{[G]\delta_G + [HG]\delta_{HG} + 2[HG_2]\delta_{HG_2} + [H_2G]\delta_{H_2G}}{[G]_t} \quad (15)$$

Fittings were conducted in Microsoft Excel 2007 using the Solver feature. All observable H and G peaks were simultaneously fitted by minimizing the total sum of squared residuals (SSR, Eq. 4), where w$_i$ are the weights assigned to each resonance, using the binding constants (K$_{dimer}$, K$_1$, K$_2$, K$_3$) and the individual chemical shifts (δ$_H$, δ$_G$, δ$_{H2}$, δ$_{HG}$, δ$_{HG2}$, and δ$_{H2G}$) as fitting parameters.

$$SSR = \sum_i w_i(\delta_i^{exp} - \delta_i^{calc})^2 \quad (16)$$

The binding constant describing the dimerization process, K$_{dimer}$, was determined through $^1$H NMR dilution experiments and was held constant throughout the fitting process. β-GlcNAc binding constants at 10 and 5° C. could not be determined due to significant signal broadening.

Molecular Modeling.

Initial structures for receptor 1 with β-Man were determined with distance constraints according to the experimental NMR data using the Maestro software package from Schrodinger, LLC (New York, N.Y.). All minimizations used the AMBER* force field (Case et al., *J. Comput. Chem.* 26:1668-1697 (2005), which is hereby incorporated by reference in its entirety) with conjugate gradients and a dielectric constant of 4.8 Debyes with extended cutoff to treat remote interactions. A maximum number of 5000 iterations using the PRCG method and a convergence threshold of 0.05 were used. For the conformational searches, a Monte-Carlo mixed torsional/low-mode sampling method (Kolossvary & Guida, *J. Comput. Chem.* 20:1671-1684 (1999), which is hereby incorporated by reference in its entirety) was used with a maximum number of 3000 steps, 100 steps per rotatable bond, 50.0 kJ mol$^{-1}$ energy window, and a distance of 3.0-6.0 Å for low-mode movements. The initial results found through such minimizations were used as input for further conformational searches. The conformational search protocol yielded only one 1:β-Man conformer, which was further optimized with density functional theory (B3LYP/6-31G+(d)) using Gaussian 09.

Example 1

Carbohydrate Receptor Synthesis

Receptor 1 was prepared in a five step synthetic sequence from 1,3-bis(bromomethyl)-5-iodobenzene 2 in a 64% overall yield (Scheme 5). After substitution to provide diazide 3, a one-pot Suzuki coupling of two equivalents of 3 yielded tetra-azide 4. An aza-Wittig reaction between 4 and 1H-pyrrole-2-carbaldehyde furnished tetra-imine 5, which finally produced receptor 1 upon reductive amination with NaBH$_4$. The reactions were characterized by $^1$H NMR, 13C NMR, and high resolution mass spectrometry, and all spectra were consistent with the proposed structures (see FIGS. 10-12).

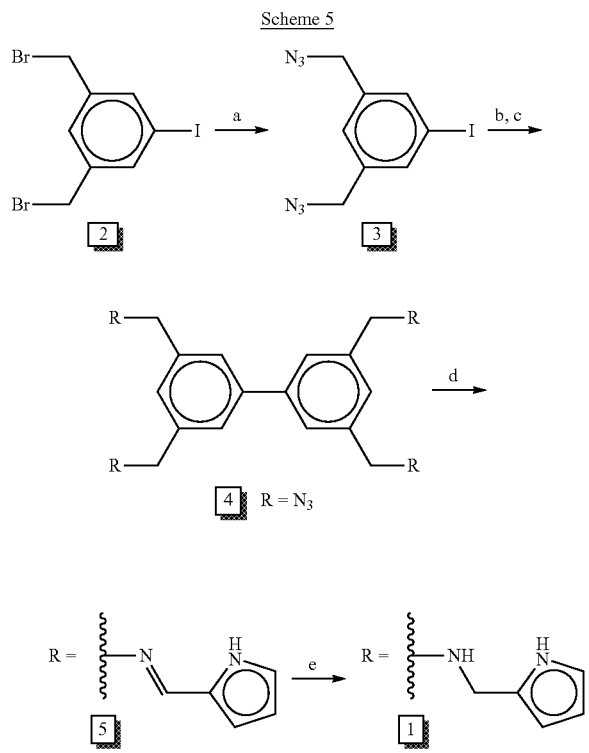

Scheme 5

Reagents and conditions:
a) NaN$_3$, DMF, 84%;
b) bis(pinacolato)diborane, (dppf)PdCl$_2$, K$_2$CO$_3$, DMF;
c) 3, (dppf)PdCl$_2$, Na$_2$CO$_3$, 95%, two steps;
d) 1H-pyrrole-2-carbaldehyde, PPh$_3$, C$_6$H$_6$;
e) NaBH$_4$, MeOH, 80%, two steps.

Example 2

Pyranoside Binding

The binding affinity and selectivity of 1 for eight octylpyranosides (FIG. 1), which were chosen as guests, because they are common terminal residues found on cell surface glycolconjugates and are used as standards for assaying synthetic receptor selectivity (ESSENTIALS OF GLYCOBIOLOGY (Ajit Varki et al. eds., Cold Spring Harbor Laboratory Press 1999); Werz et al., *ACS Chem. Biol.* 2:685-691 (2007), which are hereby incorporated by reference in their entirety), were investigated by variable temperature $^1$H NMR titrations in CDCl$_3$. Chloroform facilitates the binding studies of new carbohydrate receptors (Davis & Wareham, *Angew. Chem. Int. Ed.* 38:2978-2996 (1999); Mazik, *RSC Adv.* 2:2630-2642 (2012); Mazik, Chem. Soc. Rev. 38:935-956 (2009); Jin et al., *Med. Res. Rev.* 30:171-257 (2010), which are hereby incorporated by reference in their entirety) because the solvent does not compete for hydrogen bonding between host and guest, thereby enhancing polar noncovalent bonds. These titrations revealed that the selectivity of 1 for octylmannosides arises through a cooperative, multistep equilibrium (FIG. 2). In solution, 1 exists as a dimer, 1$_2$, that comes apart to form 1:1 complexes with the eight pyranosides with little selectivity. Upon altering the 1:pyranoside ratio from 1:1, two new mannoside-selective binding modes emerge that are both the result of positive cooperativity at 25° C. When the concentration of mannoside is increased, 1:2 receptor:pyranoside complexes form only with α-Man (1:α-Man$_2$) and β-Man (1:β-Man$_2$). If instead, the concentration of 1 increases with respect to pyranoside, a 2:1 receptor:monosaccharide complex forms only with 13-Man (1$_2$:β-Man). To understand the origin of the preferential binding of mannosides by 1, these binding stoichiometries and the structures of 1$_2$:β-Man$_2$:α-Man$_2$, and 1:β-Man$_2$ were established through a variety of 1D and 2D NMR methods, and all values of K$_1$, K$_2$, K$_3$, ΔH° and ΔS° were determined for each of these equilibria (see FIGS. 15-32).

Example 3

1:2 Receptor:Pyranoside Binding

Figures 3A, 3B, 3C:
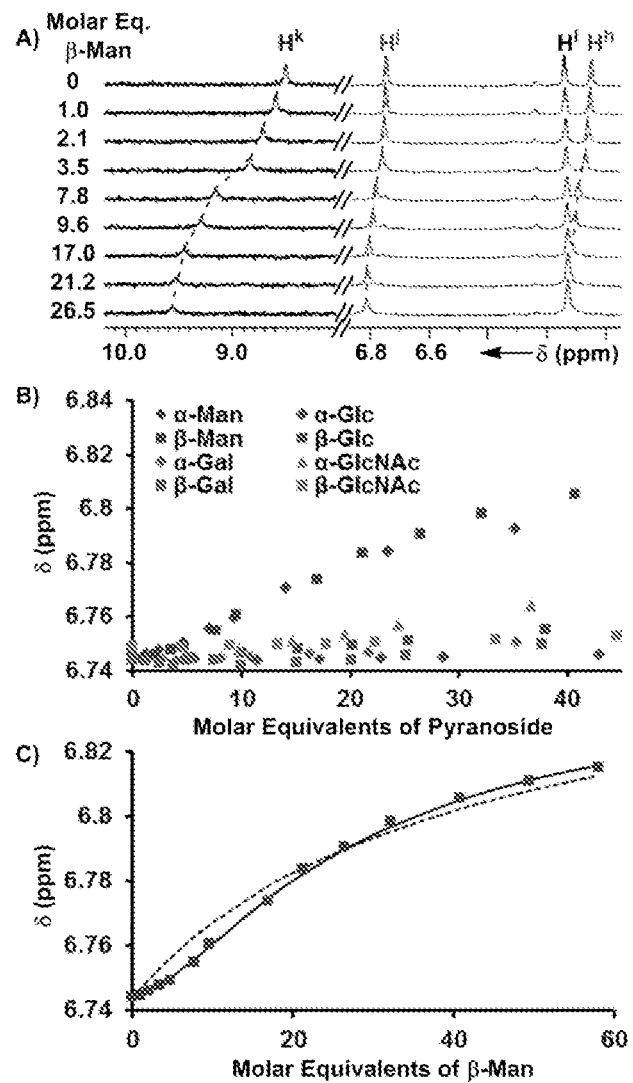
FIGS. 3A-3C demonstrate 1:2 receptor:pyranoside binding.
Figure 16:
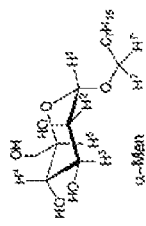
FIG. 16 is a table showing $^1$H NMR (900 MHz, 25° C.) chemical shift data for a 1.0 mM solution of α-Man in CDCl$_3$ upon incremental addition of compound 1 (Scheme 5).
Figure 16:
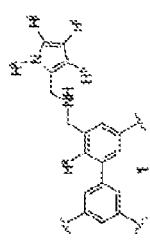
Figures 17A, 17B:
Figures 18A, 18B, 18C, 18D, 18E:
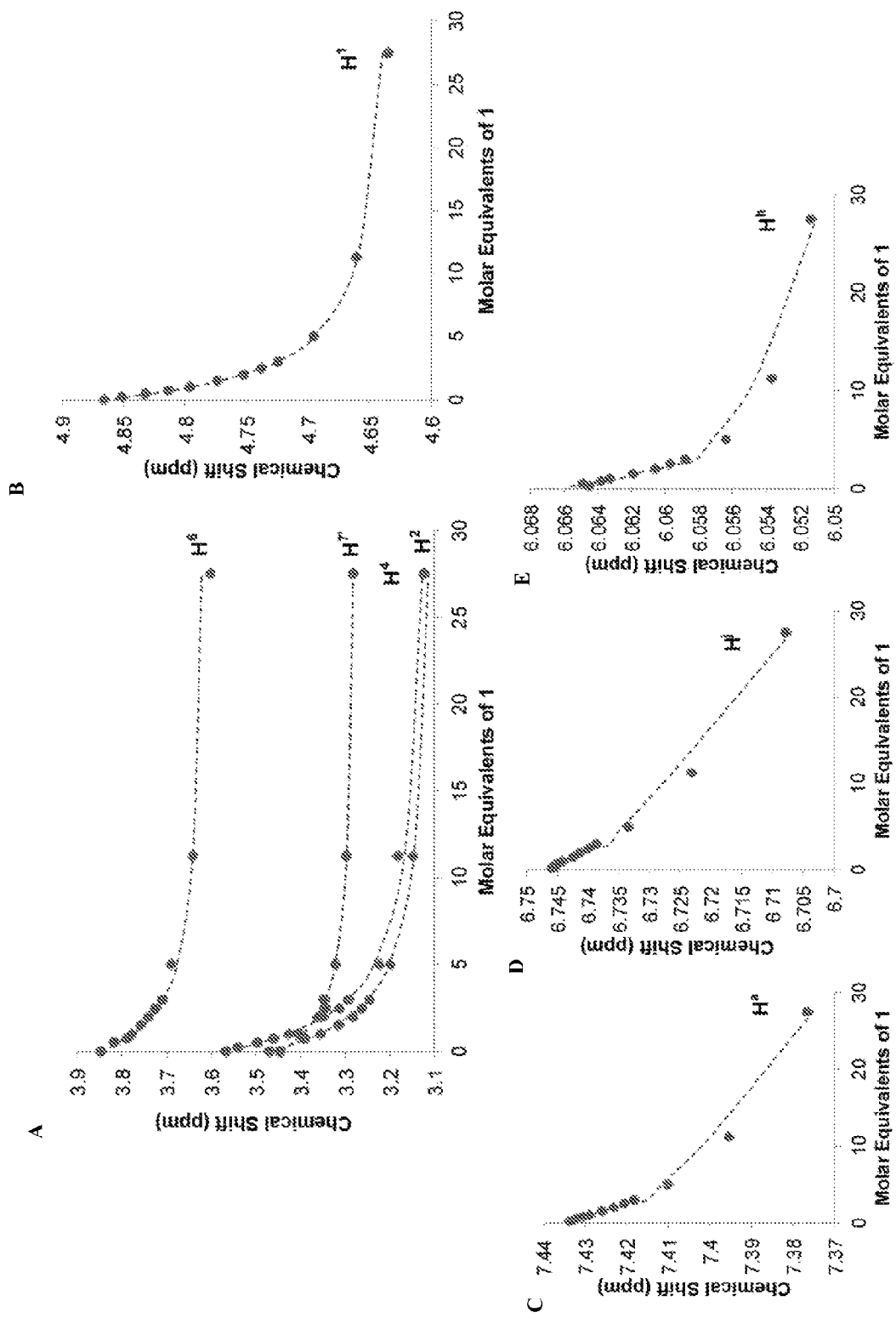
FIGS. 18A-18E are graphs fitting the experimental data (circles) with the 1:1 model (dashed line) corresponding to the $^1$H NMR titration of α-Glc with compound 1 (Scheme 5) at 25° C.
Figure 19A:
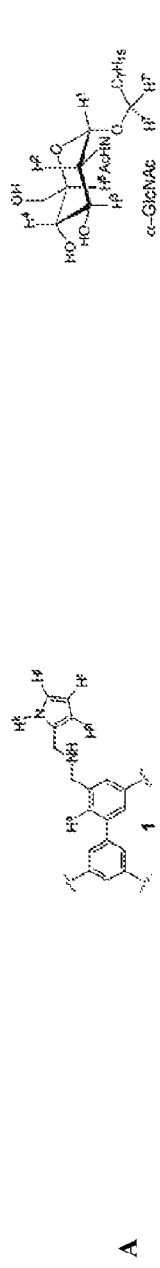
Figures 20A, 20B, 20C, 20D, 20E:
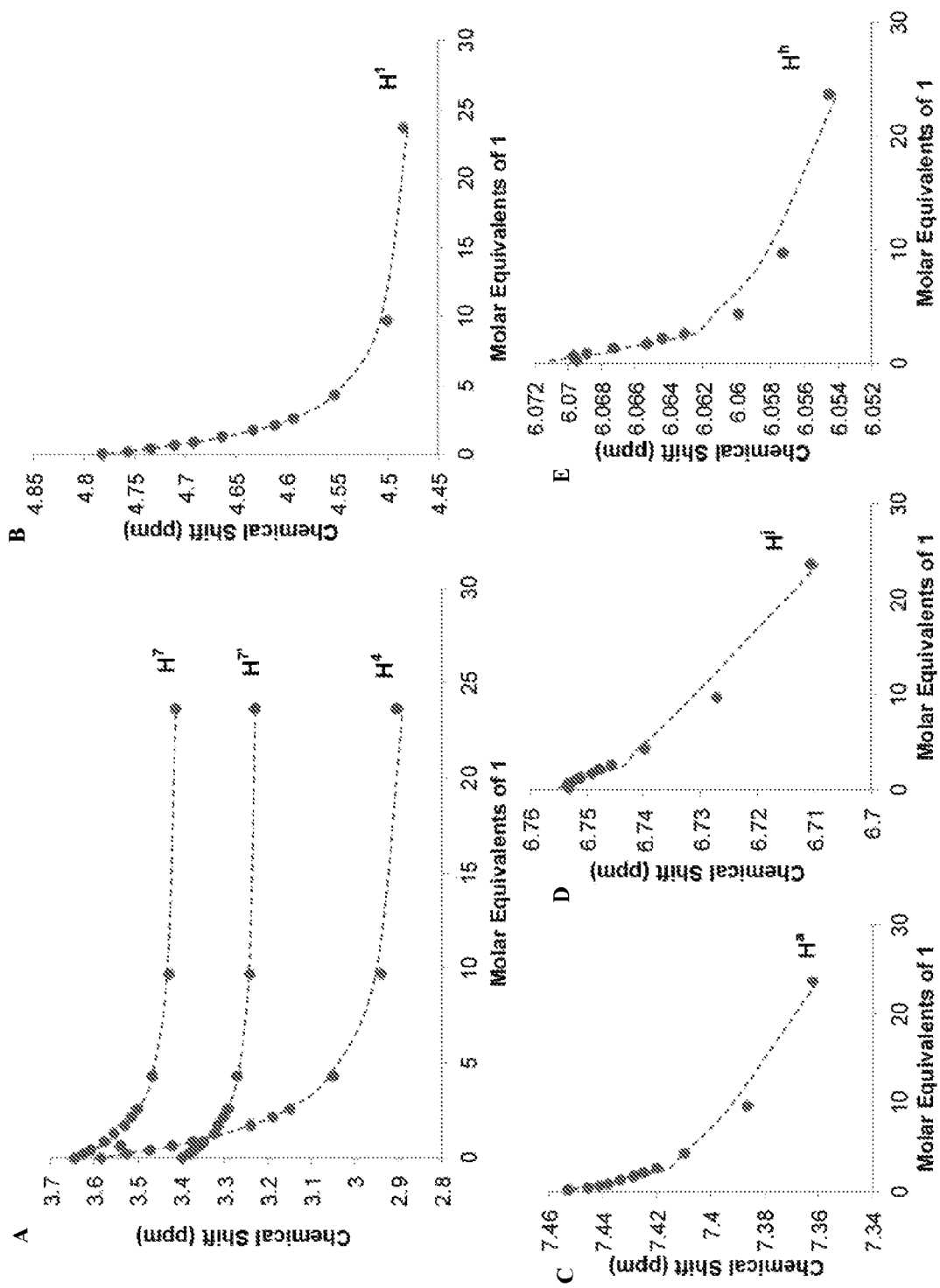
FIGS. 20A-20E are graphs fitting the experimental data (circles) with the 1:1 model (dashed line) corresponding to the $^1$H NMR titration of α-GlcNAc with compound 1 (Scheme 5) at 25° C.
Figures 21A, 21B:
Figures 22A, 22B:
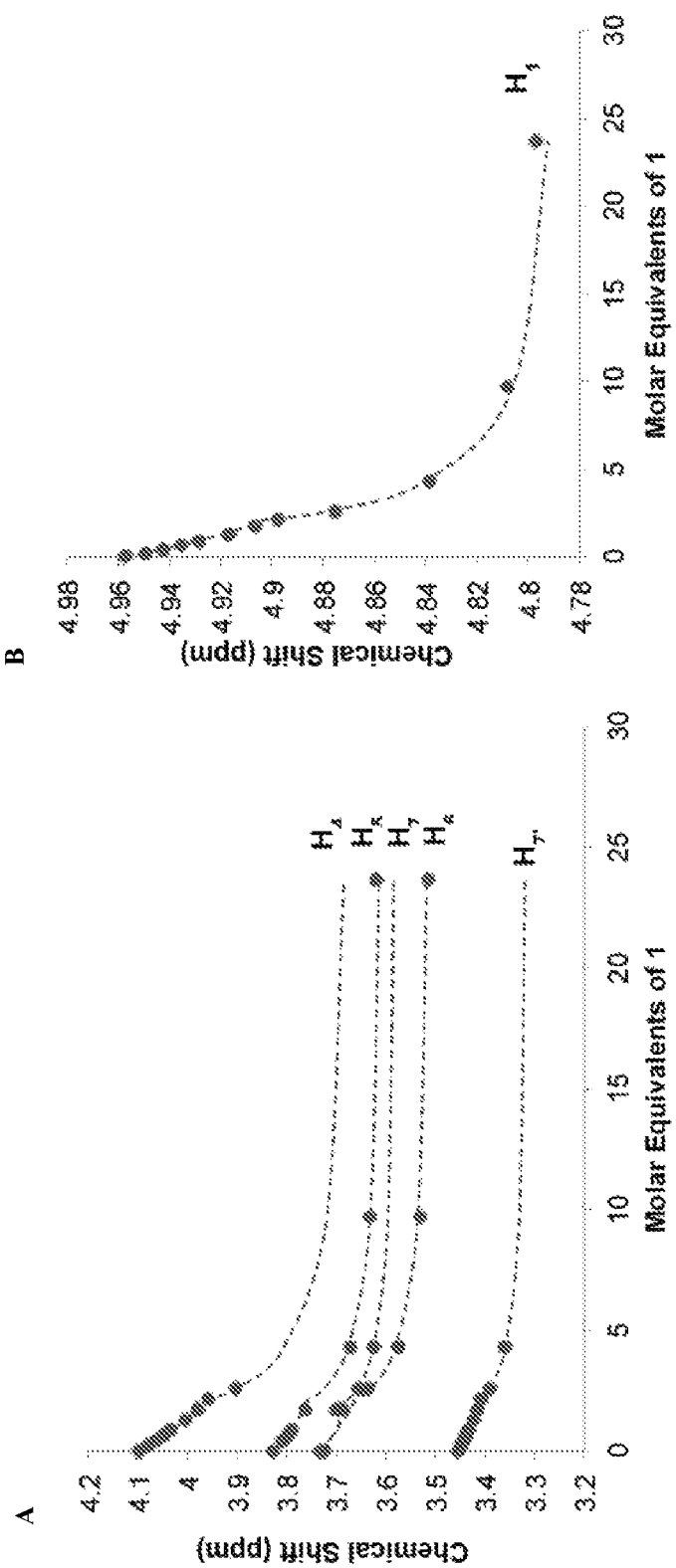
FIGS. 22A-22E are graphs fitting the experimental data (circles) with the 1:1 model (dashed line) and 2:1 model (solid line) corresponding to the $^1$H NMR titration of α-Gal with compound 1 (Scheme 5) at 25° C.
Figures 22C, 22D, 22E:
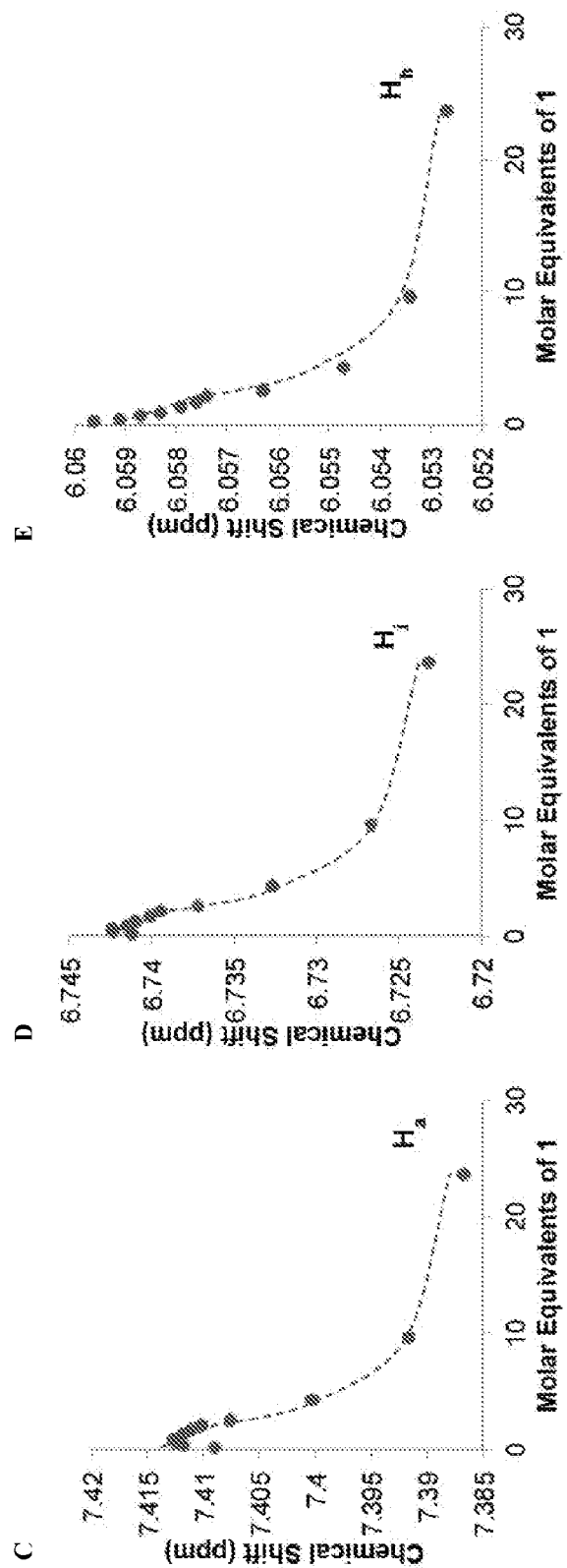
Figures 24A, 24B:
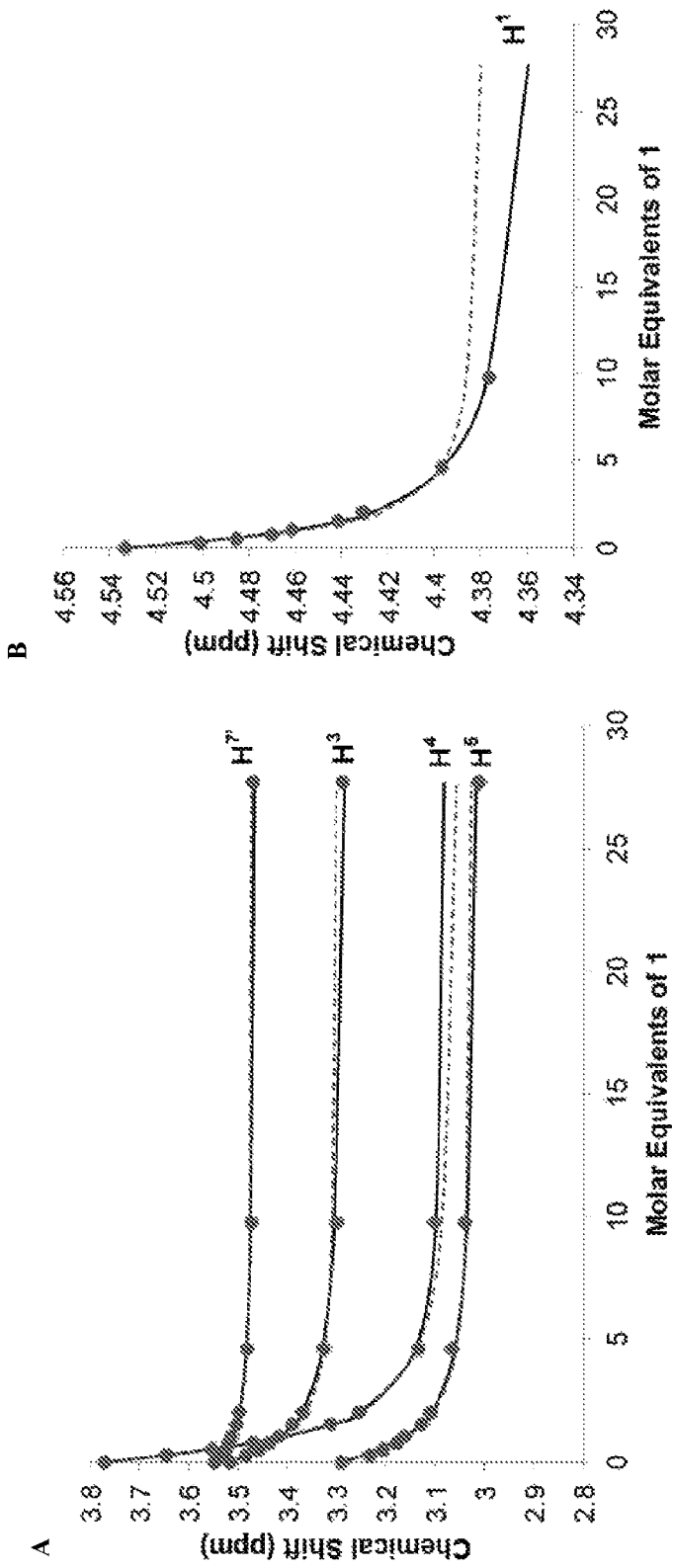
FIGS. 24A-24E are graphs fitting the experimental data (circles) with the 1:1 model (dashed line) and 2:1 model (solid line) corresponding to the $^1$H NMR titration of β-Man with compound 1 at 25° C.
Figures 24C, 24D, 24E:
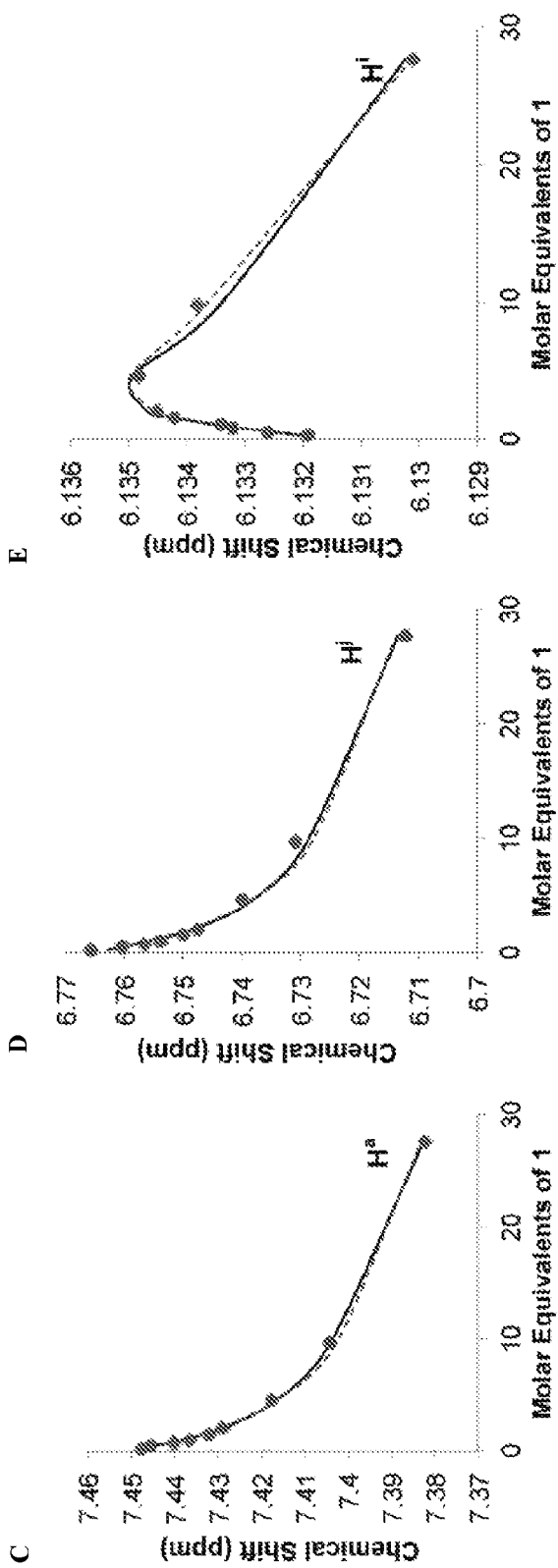
Figures 26A, 26B, 26C, 26D, 26E:
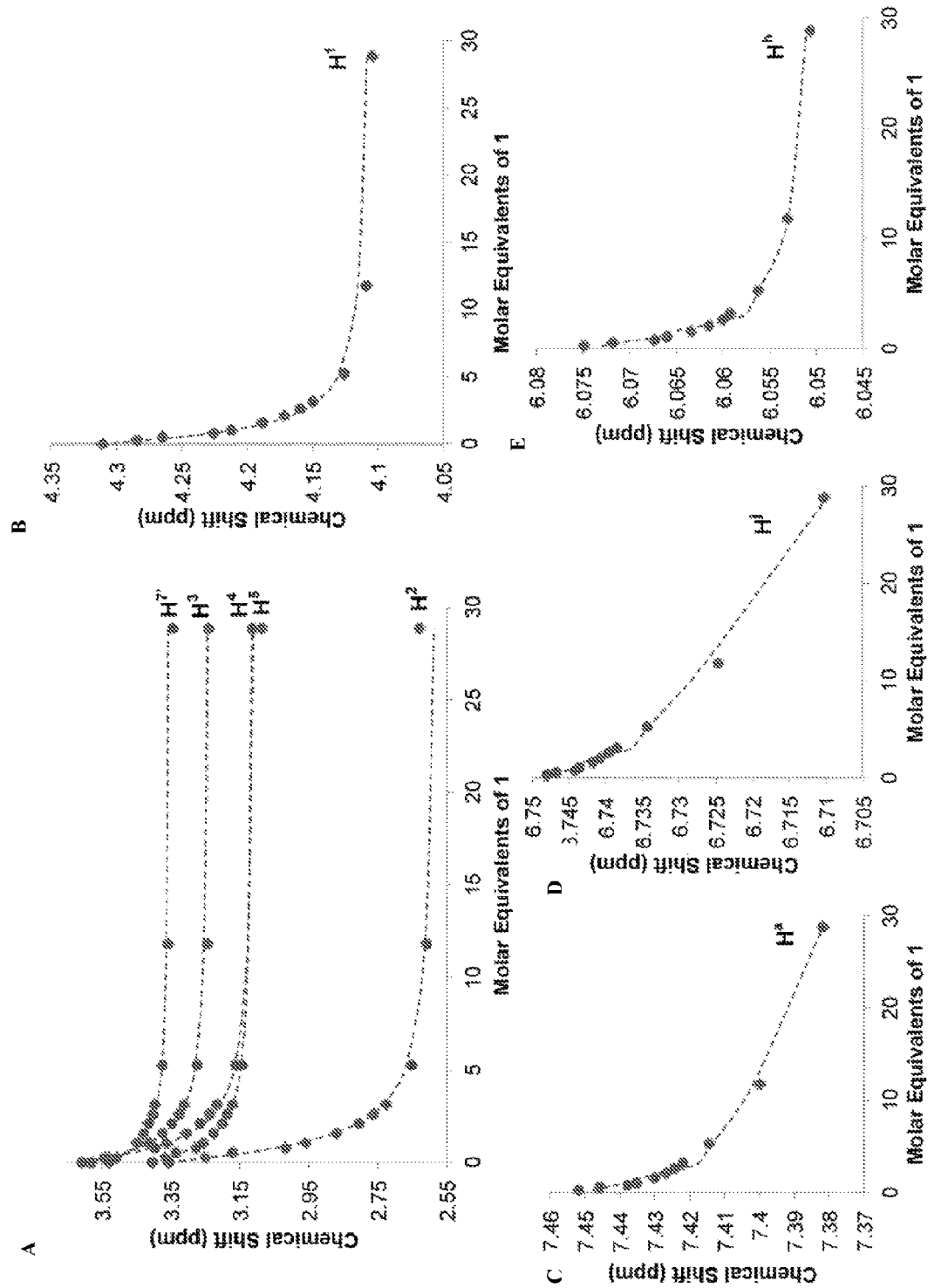
FIGS. 26A-26E are graphs fitting the experimental data (circles) with the 1:1 model (dashed line) corresponding to the $^1$H NMR titration of β-Glc with compound 1 at 25° C.
Figures 27A, 27B:
Figures 28A, 28B, 28C, 28D, 28E:
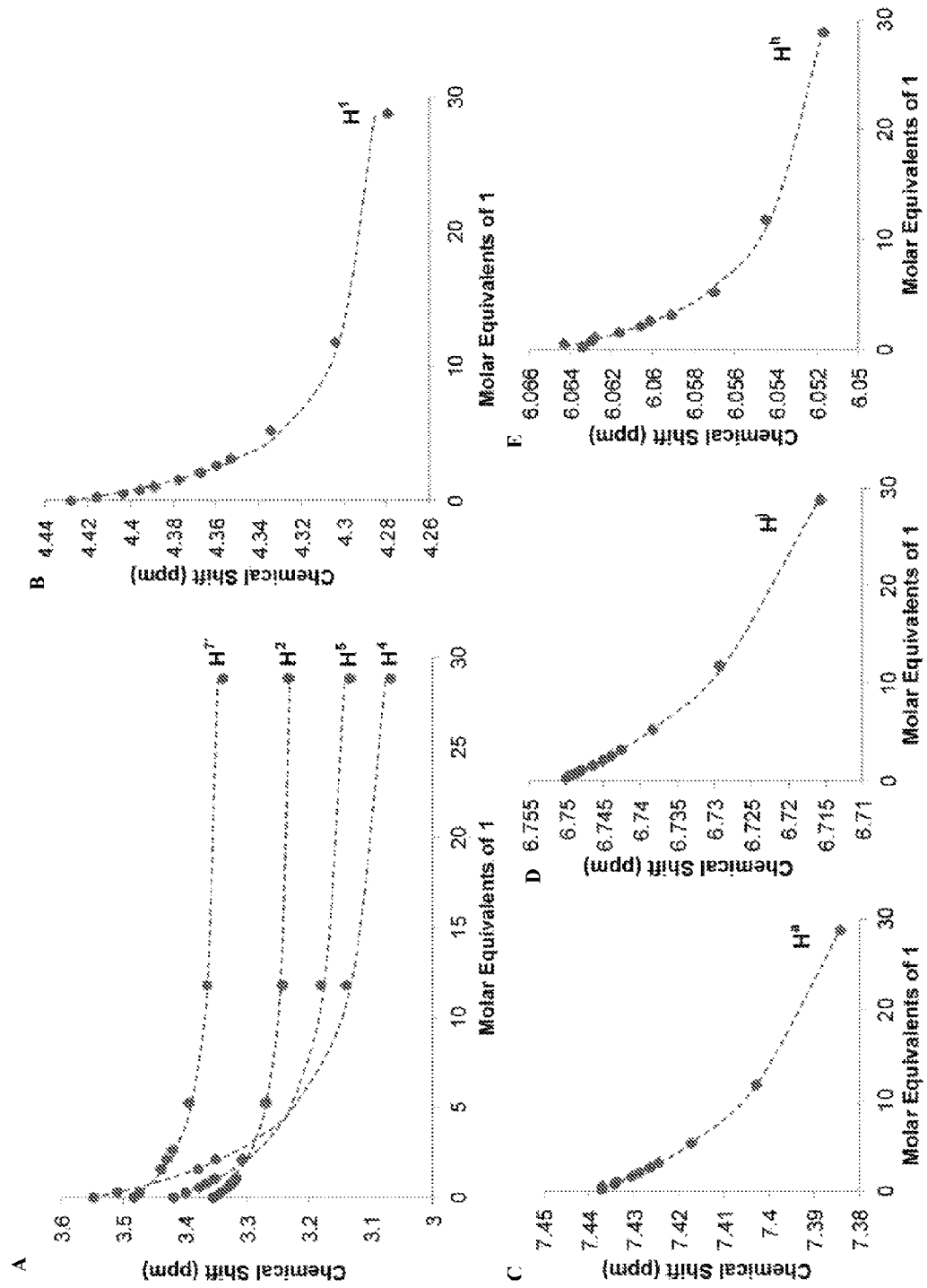
FIGS. 28A-28E are graphs fitting the experimental data (circles) with the 1:1 model (dashed line) corresponding to the $^1$H NMR titration of β-GlcNAc with compound 1 at 25° C.

The quantification of K$_{dimer}$, K$_1$, K$_2$, and K$_3$ from a single $^1$H NMR titration experiment under the fast exchange regime is possible by fitting the chemical shift changes, Δδ, but the large number of fitting parameters often results in multiple points of convergence (Thordarson, *Chem. Soc. Rev.* 40:1305-1323 (2011), which is hereby incorporated by reference in its entirety). Thus, the binding of pyranosides was first studied under conditions where receptor 1 was maintained at a low concentration (<70 μM) to minimize the contribution of the K$_{dimer}$ and K$_3$ equilibria (FIG. 2). Once the values of K$_1$ and K$_2$ were determined, their values were held invariant in subsequent peak shift fittings, which facilitated the quantification of the other K$_a$s. The incremental addition of a 10-12 mM solution of each of the eight octylpyranoside to a dilute solution of 1 (58.6 μM) induced changes in the $^1$H NMR chemical shifts corresponding to the protons of 1, owing to a fast exchange between bound and unbound substrates on the NMR timescale (FIG. 3A and FIGS. 15A-15K). Notably, the change of mannoside proton chemical shifts, Δδ, was significantly greater than the other pyranosides, suggesting that the overall binding free energy, ΔG°, was greater for mannosides than other pyranosides (FIG. 3B and FIG. 16). When the observed chemical shifts were plotted against the molar equivalents of pyranoside (FIG. 3C), the observed perturbations for the mannoside protons follow a sigmoidal pattern, indicating that multiple equilibria in addition to 1:1 complexation are occurring in the titration (Wilcox et al., *J. Am. Chem. Soc.* 114:10189-10197 (1992), which is hereby incorporated by reference in its entirety). The titration induced peak shifts occurring upon addition of both anomers of glucose (α/β-Glc), galactose (α/β-Gal), and N-acetylglucosamine (α/β-GlcNAc) produced no such sigmoidal curve and instead follow the hyperbolic shape of a 1:1 binding isotherm (FIG. 3B; see also FIGS. 17-30) (KENNETH A. CONNORS, BINDING CONSTANTS: THE MEASUREMENT OF MOLECULAR COMPLEX STABILITY (John Wiley & Sons, Inc. 1987), which is hereby incorporated by reference in its entirety). Since the concentration of pyranosides was intentionally kept low, the saturation region of the binding isotherm was only reached for the mannosides (FIG. 3C), thus $K_1$ could not be determined for the other pyranosides from these experiments, although these values were obtained by titrating 1 into solutions of pyranoside as described below.

The chemical shift changes that occur because of the interaction of 1 with α- and β-Man were subjected to a global nonlinear fitting analysis with a model incorporating $K_{dimer}$, $K_1$, and $K_2$, and satisfactory fits to the Δδs were obtained to provide macroscopic $K_a$s indicating the presence of 1:2 receptor:mannoside complexes 1:α-Man$_2$ and 1:β-Man$_2$ (FIG. 3C and FIGS. 24A-24E). For an allosteric receptor possessing two equivalent binding sites, the experimentally measured $K_a$s must be corrected for the existence of two identical 1:1 intermediates to obtain microscopic association constants that accurately describe the association of each binding site (Connors et al., *J. Org. Chem.* 53:2023-2026 (1988); Hunter & Anderson, *Angew. Chem. Int. Ed.* 48:7488-7499 (2009); Ercolani & Schiaffino, *Angew. Chem. Int. Ed.* 50:1762-1768 (2011), which are hereby incorporated by reference in their entirety). Since there are two identical pathways by which α/β-Man can associate with 1 to form a 1:1 complex, the macroscopic $K_a$ for the first association process was divided by 2 to obtain microscopic association constant $K_1$. Likewise, as there are two identical pathways for dissociation in 1:Man$_2$, the macroscopic $K_a$ for the second association process was multiplied by 2 to obtain microscopic association constant $K_2$ (Table 1). The interaction parameter, a, is the ratio of a microscopic $K_a$ in the cooperativity, or reference $K_a$, and is a quantitative measure of cooperativity (Connors et al., *J. Org. Chem.* 53:2023-2026 (1988); Hunter & Anderson, *Angew. Chem. Int. Ed.* 48:7488-7499 (2009); Ercolani & Schiaffino, *Angew. Chem. Int. Ed.* 50:1762-1768 (2011), which are hereby incorporated by reference in their entirety). Since both binding sites are identical, the reference $K_a$ is equivalent to $K_1$ and thus $\alpha = K_2/K_1$. An a value greater than 1 indicates that the first association event enhances the second, i.e. positive cooperativity (Connors et al., *J. Org. Chem.* 53:2023-2026 (1988); Hunter & Anderson, *Angew. Chem. Int. Ed.* 48:7488-7499 (2009); Ercolani & Schiaffino, *Angew. Chem. Int. Ed.* 50:1762-1768 (2011), which are hereby incorporated by reference in their entirety). Likewise, the binding is negatively cooperative if a is less than 1, and the binding is non-cooperative if a is equal to 1. From an analysis of the microscopic $K_a$s, α-Man and β-Man were both found to possess a values of 13.7 and 7.6, respectively, with receptor 1, indicating a high degree of positive cooperativity occurs between 1 and both mannosides (Table 1).

TABLE 1

Binding constants ($K_a$s, 25° C.) and thermodynamic parameters (ΔH°, ΔS°) associated with the 1:1 (upper value), 1:2 (middle value), and 2:1 (lower value) 1: pyranoside binding determined by NMR titrations and the intrinsic median binding concentration $BC_{50}^0$ calculated from $K_{dimer}$, $K_1$, $K_2$, and $K_3$ for each pyranoside interacting with 1 in CDCl$_3$ at 25° C.

| Glycoside | Log K | ΔH° (kcal mol$^{-1}$) | ΔS° (e.u.) | $BC_{50}^0$ (mM) |
|---|---|---|---|---|
| α-Glc | 2.75 ± 0.04 | −12.5 ± 0.3 | −29 ± 1 | |
| | a | — | — | 1.86 ± 0.16 |
| | a | — | — | |
| β-Glc | 3.16 ± 0.01 | −16.5 ± 0.1 | −41 ± 1 | |
| | a | — | — | 0.70 ± 0.02 |
| | 0.39$^b$ | −6.6 ± 0.4 | −21 ± 1 | |
| α-Man | 2.57 ± 0.19 | c | c | |
| | 3.71 ± 0.10 | c | c | 0.46 ± 0.05 |
| | a | — | — | |
| β-Man | 2.46 ± 0.31 | −20.5 ± 0.8 | −57 ± 3 | |
| | 3.34 ± 0.11 | −20.2 ± 1.2 | −52 ± 4 | 0.73 ± 0.10 |
| | 2.45 ± 0.09 | −11.0 ± 0.4 | −26 ± 2 | |
| α-Gal | 2.18 ± 0.02 | −13.1 ± 0.5 | −34 ± 2 | |
| | a | — | — | 7.74 ± 0.31 |
| | a | — | — | |
| β-Gal | 2.59 ± 0.03 | −15.4 ± 0.8 | −40 ± 3 | |
| | a | — | — | 2.74 ± 0.18 |
| | a | — | — | |
| α-GlcNAc | 2.53 ± 0.02 | −11.4 ± 0.2 | −26 ± 1 | |
| | a | — | — | 3.18 ± 0.14 |
| | a | — | — | |
| β-GlcNAc | 2.65 ± 0.05 | −11.8 ± 0.5 | −27 ± 4 | |
| | a | — | — | 2.37 ± 0.26 |
| | a | — | — | |

The thermodynamic origin of this positive allosteric cooperativity in the formation of 1:β-Man$_2$ was investigated by determining ΔH° and ΔS° associated with each binding step. The $^1$H NMR titrations between 1 and β-Man were repeated at 20, 15, and 10° C., and $K_1$ and $K_2$ values for each temperature were obtained and subjected to Van't Hoff analyses (FIG. 32D) to provide the thermodynamic parameters associated with each binding event. Notably, the ΔH°s of association for the first and second binding step are identical, −20.5±0.8 and −20.2±1.2 kcal mol$^{-1}$ respectively, suggesting that both equivalents of β-Man bind 1 with an identical number of noncovalent interactions and that the mannosides do not interact with each other when bound to 1. A comparison of the corresponding ΔS° values indicates a decrease in the unfavorable ΔS° occurs in the second binding step compared to the first, −52±4 and −57±3 e.u. respectively (FIG. 32D).

Figure 4:
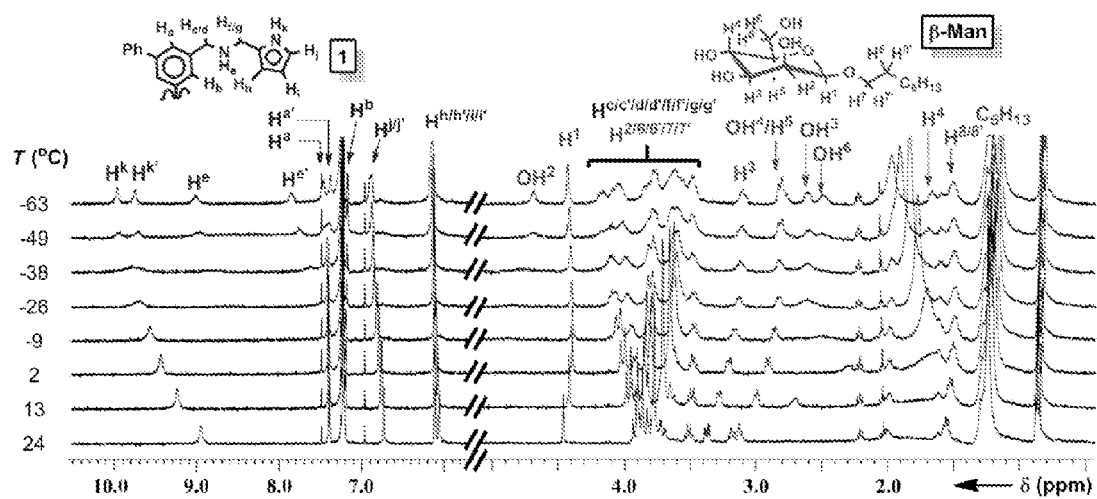
FIG. 4 is a variable temperature 1H NMR (400 MHz, CDCl$_3$) spectra of compound 1 (1.0 mM) and β-Man (2.0 mM).
Figure 13:
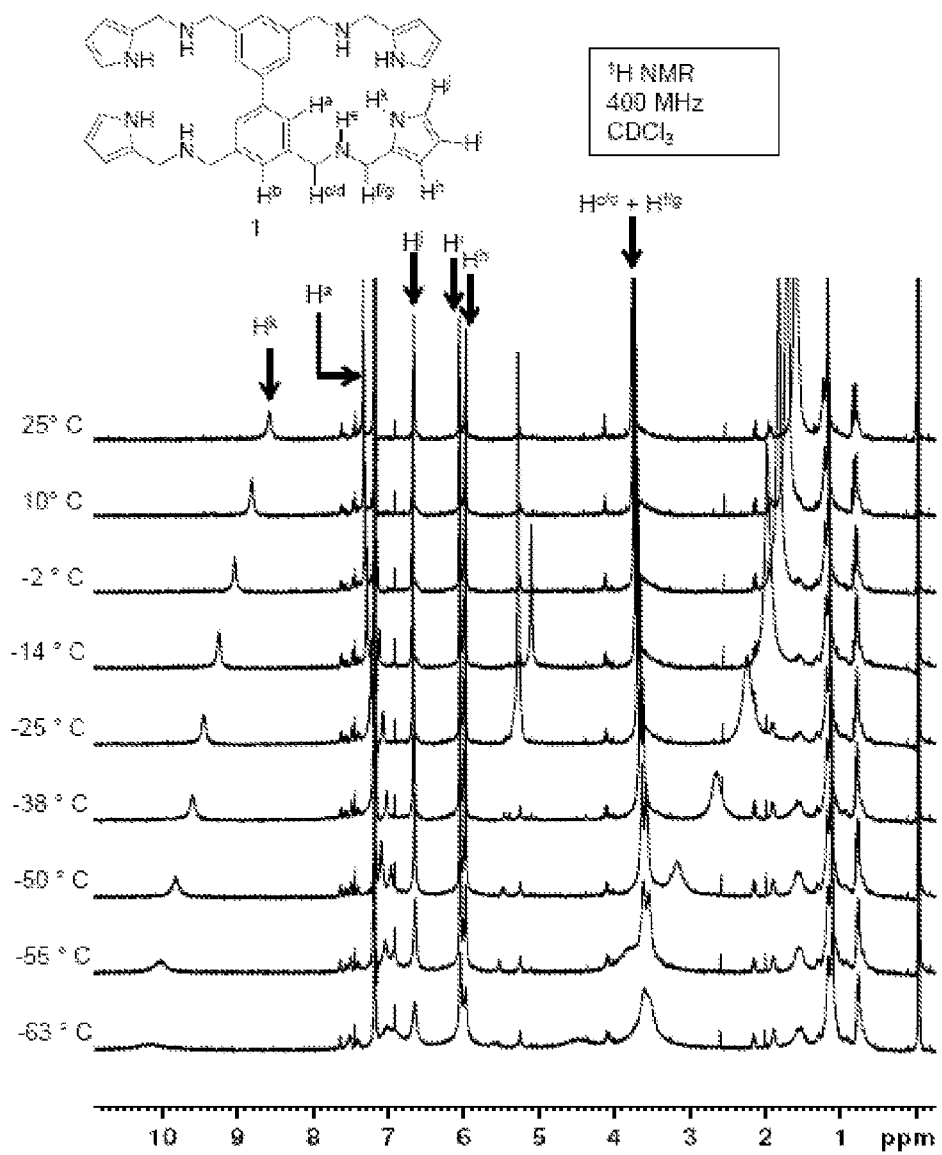
FIG. 13 is a variable temperature 1H NMR (400 MHz, CDCl$_3$) spectra of 1.0 mM solution of compound 1 (Scheme 5) in CDCl$_3$.
Figure 14:
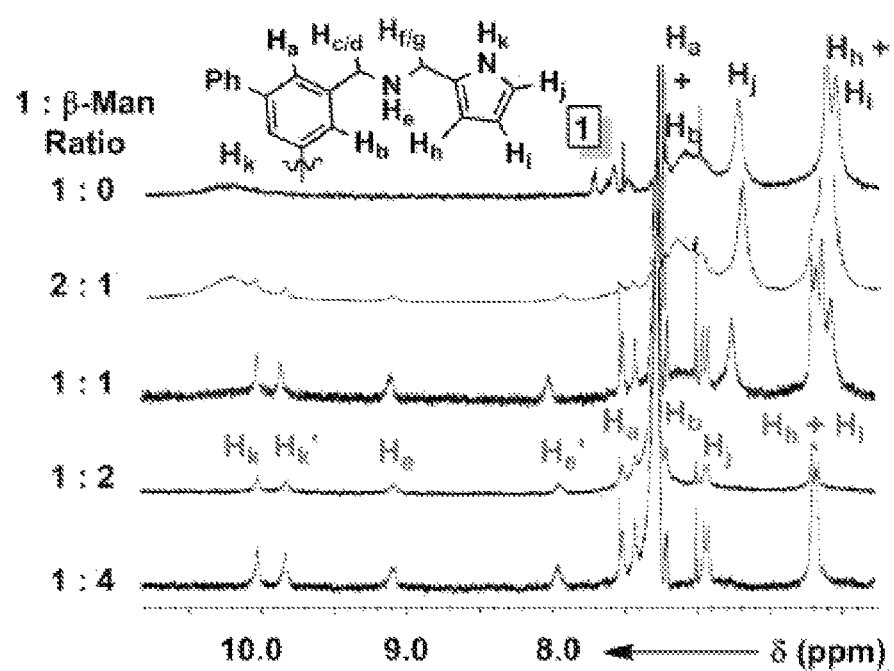
FIG. 14 is a $^1$H NMR (400 MHz, CDCl$_3$, −63° C.) of compound 1 (Scheme 5) (6.0 mM for 2:1 1:β-Man; 1.0 mM for all other ratios) and β-Man. The blue and purple signals correspond to 1 and 1; β-Man$_2$ respectively.
Figure 15G:
Figure 15H:

The geometries of 1:β-Man and 1:β-Man$_2$ were determined by 1D and 2D $^1$H NMR and computational modeling to understand the structural origin of the cooperative binding. The $^1$H NMR spectrum of a solution of 1 (1 mM) and β-Man (2 mM) in CDCl$_3$ exhibits averaged signals for all protons at 25° C. because of a fast exchange of the signals corresponding to 1, β-Man, 1:β-Man$_2$, and 1:β-Man. Upon cooling, the $^1$H NMR resonances corresponding to 1, except H$^b$, decoalesce into two sets of peaks at −40° C. (FIG. 4), indicating a partial desymmetrization occurring with receptor 1. No decoalescence was observed for the resonances corresponding to β-Man signals upon cooling the solution (FIG. 4), suggesting that both equivalents of β-Man occupy identical chemical environments in the 1:β-Man$_2$ complex. In the absence of β-Man (FIG. 13), the signals corresponding to 1 in the $^1$H NMR spectrum do not decoalesce at low temperature, but rather are β-Man. A comparison of the $^1$H NMR spectra at −63° C. with varying ratios of 1:β-Man revealed that the broad signals corresponding to free 1 disappear when more than two molar equivalents of β-Man are present in solution, further confirming the 1:2 stoichiometry of the complex (FIG. 14). The $^1$H NMR spectrum at −63° C. (1.0 mM 1, 2.0 mM β-Man, CDCl$_3$) is useful for determining the structure of 1:β-Man$_2$ (FIG. 4). Two sets of signals are observed for the receptor and only one for the mannoside, indicating that both pyranosides are bound to two aminopyrrolitic arms of 1 and are symmetrically equivalent, resulting in a complex that exhibits C$_2$ symmetry. A configuration where each mannose binds to two aminopyrrolitic arms on the same aromatic ring would render both H$^b$ protons of receptor 1 symmetrically equivalent, which is consistent with the lack of decoalescence of the H$^b$ peak in 1:β-Man$_2$. The two amine protons, H$^e$ and H$^{e'}$, shift considerably downfield to 9.1 and 7.9 ppm (FIG. 4), indicating that both protons are involved in H-bonding (Friebolin, *Basic One- and Two-Dimensional NMR Spectroscopy* (Wiley-VCH, 4$^{th}$ ed. 2005), which is hereby incorporated by reference in its entirety). Likewise, the large complexation-induced shift (CIS) of H$^4$ from 3.7 to 1.2 ppm is consistent with a C—H$\cdots$π interaction between H$^4$ and a phenyl ring of 1. Finally, the $^1$H-$^1$H ROESY spectrum of the mixture revealed a through-space correlation between the octyl chain (presumably H$^9$) and pyrrole proton H$^{j'}$ (FIGS. 24, 25, and 35) which confirms that the octyl chain of β-Man is within close proximity to one of the aminopyrrolitic arms of 1.

Figures 5A, 5B, 5C:
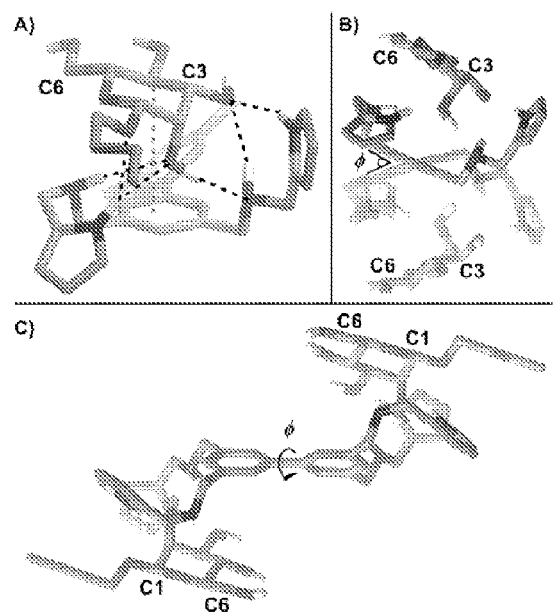
FIGS. 5A-5C show the energy minimized structure (DFT, B3LYP/6-31+(d)) for 1:β-Man from an initial binding geometry obtained by an AMBER* mixed low-mode/torsional Monte Carlo conformation search.

With NMR providing a general understanding of how β-Man sits within 1, a molecular mechanics (AMBER*) (Case et al., *J. Comput. Chem.* 26:1668-1697 (2005), which is hereby incorporated by reference in its entirety) Monte Carlo conformational search was utilized to model the binding geometry of the 1:β-Man complex. The identical values of ΔH° that were determined for each binding step and the C$_2$ symmetry observed in the $^1$H NMR spectrum of the 1:β-Man$_2$ complex indicate that the mannosides occupy identical binding sites on the receptor. Proton H$^4$ was constrained to be within close proximity of the biphenyl ring system in accordance with the experimentally observed C—H$\cdots$π interaction, and the octyl chain was positioned near one arm of 1 with a restricted distance of 2-4 Å between H$^9$ and H$^{j'}$ as dictated by the observed NOE between these two protons. The conformational searches yielded only one minimum energy structure for 1:β-Man, which was further optimized using density functional theory (B3LYP/6-31G+(d)). The resulting calculated structure (FIG. 5A) is in excellent agreement with the experimental 1D $^1$H NMR data because all polar hydrogens shifted significantly downfield (H$^k$, H$^{k'}$, H$^e$, H$^{e'}$, and OH$^2$) participate in H-bonds, and a C—H$\cdots$π interaction is present between H$^4$ and a phenyl ring of 1. Likewise, the protons of the hydroxyl groups bound to the C3, C4, and C6 of β-Man do not participate in H-bonding in the calculated structure, and the corresponding peaks are observed in the $^1$H NMR region typical for hydroxyl protons not participating in H-bonding (2.4-2.8 ppm).

Computational methods were employed to understand the source of cooperativity in receptor 1 by examining the dihedral about the biphenyl bond (ϕ, FIG. 5B/C) as this is the only dynamic element of the receptor that is shared by both binding sites. While desolvation contributes significantly to ΔS°, it is not a source of cooperativity as both binding sites and mannosides are solvated identically. Previously, both restricted bond rotations (Wakabayashi et al., *Angew. Chem. Int. Ed.* 48:6667-6670 (2009); Ayabe et al., *Angew. Chem. Int. Ed.* 41:2790-2792 (2002); Raker & Glass, *J. Org. Chem.* 67:6113-6116 (2002), which are hereby incorporated by reference in their entirety) and induced torsional strain (Ercolani, *Org. Lett.* 7:803-805 (2005), which is hereby incorporated by reference in its entirety) have been cited as a source of positive cooperativity in a system where rotation must be halted to bind two equivalents of a substrate. A comparison of the DFT (B3LYP/6-31G+(d)) minimized structures corresponding to 1, 1:β-Man, and 1:β-Man$_2$ revealed ϕ values of 40.2°, 38.5°, and 39.1° respectively, indicating that the contribution of torsional strain towards the observed cooperativity is negligible because ϕ in the bound state is close to the preferred ϕ of unbound 1. More likely, the presence of a bound β-Man restricts the rotation about ϕ and incurs an entropic penalty that is only paid in the first association.

Example 4

1:1 and 2:1 Receptor:Pyranoside Binding

Figures 6A, 6B:
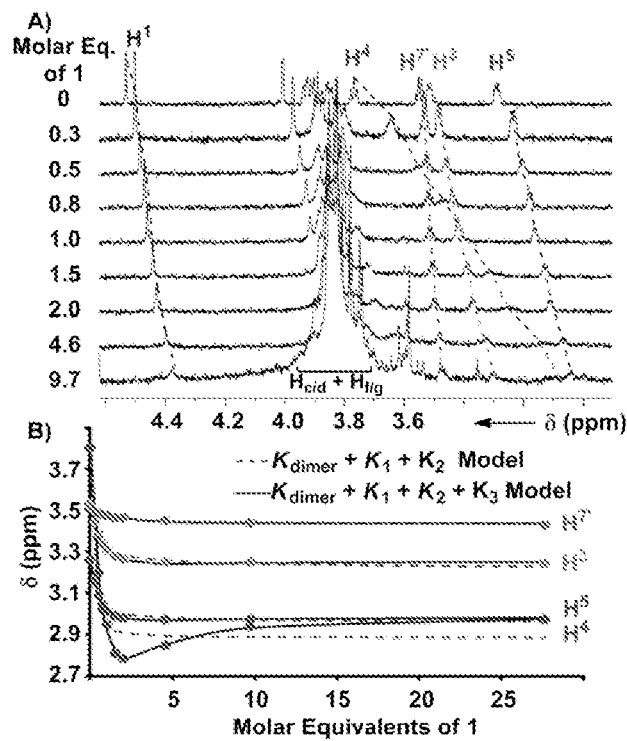
FIG. 6A is a $^1$H NMR (900 MHz, CDCl$_3$, 25° C.) spectra obtained upon the titration of a 62.5 mM solution of compound 1 to a 0.98 mM solution of β-Man with dashed lines illustrating the induced changes in δ.
FIG. 6B is a graph showing the chemical shifts, δ, of β-Man as a function of molar equivalents of compound 1 at 5° C. The theoretical global fits with a model incorporating $K_{dimer}$, $K_1$, and $K_2$ (dashed line) and with $K_{dimer}$, $K_1$, $K_2$, and $K_3$ (solid line) are shown.

The K$_1$ and K$_3$ of the binding of 1 to pyranosides (FIG. 2) were determined by titrating a solution of 1 (53.0-62.5 mM) into a 1.0 mM CDCl$_3$ solution of each octyl glycoside (FIG. 1) until a large excess of 1 was reached. Addition of 1 produced considerable changes in the $^1$H NMR resonances of the receptor and all eight pyranosides (FIG. 6A and FIGS. 15A-15K). For each non-mannoside, K$_1$ was determined by subjecting all resolvable resonances from each titration at 25° C. to a global nonlinear fitting analysis with a model combining K$_1$ and K$_{dimer}$ (13.0±0.5 M$^{-1}$), which was measured independently by $^1$H NMR dilution experiments (Table 1). Likewise, when the observed upfield chemical shift changes associated with α-Man were fit to a model incorporating K$_{dimer}$ and the previously determined values of K$_1$ and K$_2$, excellent fits for the peak shifts were obtained (Table 1). However, the peak shifts for the β-Man titration could only be fit accurately when the formation of a complex consisting of two molecules of 1 and one molecule of β-Man (1$_2$:β-Man, FIG. 2) was considered (FIG. 6B). The observed Δδs were fit to a model consisting of K$_{dimer}$, K$_1$, K$_2$, and K$_3$, with every binding constant except K$_3$ held invariant, to determine K$_3$ for β-Man. The values of log K$_1$ for binding between 1 and all pyranosides range from 2.5 to 3.3 with the highest values associated with α- and β-Man and β-Glc (Table 1). Importantly, little difference exists between the K$_1$s for the eight pyranosides, indicating that little selectivity occurs in the first binding event. In contrast to the modest selectivity found in K$_1$, 2:1 binding is only observed for β-Man at 25° C. (K$_3$=282 M$^{-1}$), although a value of K$_3$=3 M$^{-1}$ for β-Glc can be extrapolated from a Van't Hoff plot (FIG. 32B). Interestingly, a second receptor association does not occur with α-Man suggesting that the octyl chain at the anomeric position, which would be orientated away from the biphenyl base of 1 in 1:α-Man (FIG. 5A), interferes with the association of a second receptor.

The cooperativity that facilitates the formation of 1$_2$:β-Man can also be understood through the interaction parameter, a, which is the ratio between the values of K$_3$ in the presence and in the absence of cooperativity, the latter being the reference K$_a$ (Connors et al., *J. Org. Chem.* 53:2023-2026 (1988); Hunter & Anderson, *Angew. Chem. Int. Ed.* 48:7488-7499 (2009); Ercolani & Schiaffino, *Angew. Chem. Int. Ed.* 50:1762-1768 (2011), which are hereby incorporated by reference in their entirety). Since the two faces of β-Man are inequivalent, the two receptors do not bind to identical sites, thus K$_1$ is not an appropriate reference K$_a$. Rather, since K$_3$ describes the binding of the β-face (Rose et al., *Proc. Nat'l. Acad. Sci. U.S.A.* 77:2439-3441 (1980), which is hereby incorporated by reference in its entirety) of β-Man, which contains H$^1$, H$^3$, and H$^5$, in the presence of a receptor bound to the α-face, which contains H$^4$, the reference K$_a$ would describe the receptor binding to the β-face in the absence of a receptor bound to the α-face. From the −63° C. $^1$H-$^1$H ROESY spectrum of 1:β-Man$_2$, there are no observable NOEs between the pyranoside protons on the β-face and the biphenyl base of receptor 1 (FIG. 33). Likewise, a ROESY spectrum performed at conditions that would produce significant quantities of the 1:1 1:β-Man complex (0.5 mM 1, 1.0 mM β-Man, 25° C.) revealed only a NOE between $H^4$ of the α-face and $H^a$ (FIG. 34). Under these experimental conditions, a 1:1 binding event between 1 and the β-face does not occur to any appreciable extent, so an approximate baseline value of $K_a \leq 104$ $M^{-1}$ was obtained. (The detection limit of the NMR instrument used is roughly 10 nmol, which corresponds to a concentration of 0.02 mM. Using the derived equilibrium constants, the concentration of 1:β-Man was determined to be 0.11 mM under the experimental conditions. Since no NOEs are observed on the β-face of fβ-Man, the concentration of the receptor bound to this face is at or below the detection limit. Under the experimental conditions, a 1:1 complex at 0.02 mM would result from an equilibrium constant of 104 $mM^{-1}$). Thus, an estimated $K_3 \geq 282$ $M^{-1}$ is evidence for positive cooperativity in $K_3$ with β-Man, with a corresponding α of at least 2.7.

To determine why $K_3$ occurs exclusively with β-Man at room temperature, $\Delta H°$ and $\Delta S°$ of association for each binding event between 1 and all pyranosides were obtained by repeating the $^1H$ NMR titrations at 20, 15, 10, and 5° C. and subjecting the resulting $K_a$s to van't Hoff analyses (Table 1 and FIGS. 32A-32D). All monosaccharides fit satisfactorily to a $K_{dimer}+K_1$ model at all temperatures, except for β-Man at all temperatures and β-Glc, at 15, 10, and 5° C., which required inclusion of the 2:1 receptor:pyranoside equilibrium ($K_3$) to achieve satisfactory fits to the titration data (FIGS. 32A-32D). When comparing the thermodynamic parameters for the formation of each 1:1 complex, a decrease in $\Delta H°$ occurs with a decrease in magnitude of $\Delta S°$, which can be rationalized within the context of enthalpy-entropy compensation (Liu & Guo, *Chem. Rev.* 101:673-695 (2001), which is hereby incorporated by reference in its entirety). Notably, the two β-monosaccharides with the highest 1:1 binding enthalpies, β-Man and β-Glc, are the only pyranosides that participate in $K_3$. The large difference in $\Delta H°$ between 1:β-Man and 1:β-Glc, -20.5 and -16.5 kcal $mol^{-1}$ respectively, suggests that the high selectivity in $K_3$ for β-Man is the result of 1 forming more noncovalent contacts with β-Man than with β-Glc, resulting in a more preorganized 1:1 complex. The $\Delta H°$s for the formation of $1_2$:β-Glc and $1_2$:β-Man, -6.6 and -11.0 kcal $mol^{-1}$ respectively, suggest that significantly more non-covalent contacts are formed in the latter, indicating that the selectivity for β-Man in the second binding event is enthalpically driven.

Figures 7A, 7B:
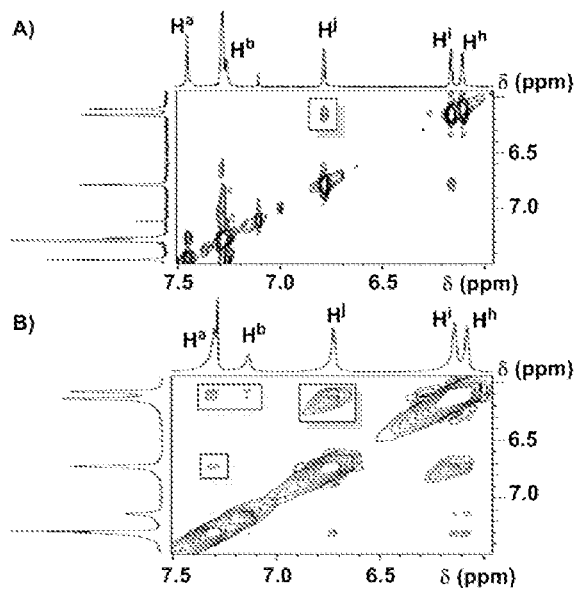
FIGS. 7A-7B show selected portions of a $^1$H-$^1$H ROESY spectra.
Figure 8:
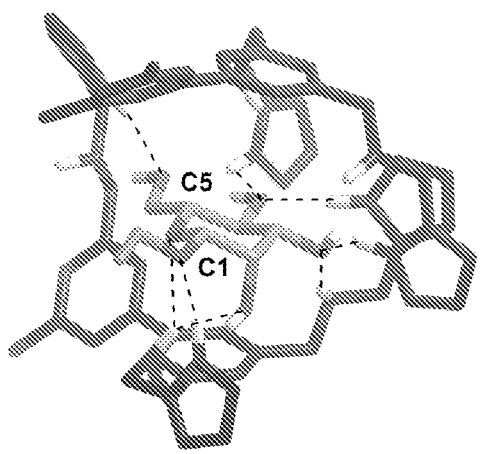
FIG. 8 depicts the energy minimized structure (AMBER*) for 1$_2$:β-Man obtained by a mixed low-mode/torsional Monte Carlo conformation search. The carbons of compound 1 that bind the α-face are colored green, and the carbons of compound 1 bound to the β-face are colored red for clarity, nitrogens are blue, oxygens are red, and intermolecular hydrogen bonds are denoted by dashed lines. Upon the association of the second equivalent of compound 1, 3 new H-bonds are observed with the β-face.

The binding geometries of 1:β-Man and $1_2$:β-Man were determined and compared to understand how the preorganization of 1:β-Man facilitates the formation of $1_2$:β-Man. A $^1H$-$^1H$ ROESY experiment that was performed under conditions (1.0 mM β-Man, 0.5 mM 1, CDCl$_3$, 298 K) that would predominantly result in a 1:1 complex (1:β-Man: 1:β-Man$_2$=2:1.5) displayed a NOE between $H^4$ and $H^a$ (FIG. 34), which is consistent with the previously determined binding geometry for 1:β-Man. Notably, in the 1:β-Man geometry, a significant portion of β-Man is exposed to solvent because one of the arms of 1 is orientated downwards underneath the n-octyl chain of β-Man which provides a window for a second equivalent of 1 to bind onto the exposed β-face of β-Man. The structure of $1_2$:β-Man was determined by performing a $^1H$-$^1H$ ROESY experiment with a concentrated 2:1 receptor:pyranoside CDCl$_3$ mixture (12.0 mM and 6.0 mM respectively) at -10° C. where $1_2$:β-Man would be the major species in solution. NOEs were observed between protons located on the biphenyl base and pyrroles (FIG. 7B), suggesting a geometry where one molecule of β-Man is encaged by two molecules of 1, and the two molecules of 1 are in close contact. By using a similar AMBER* conformational search that was used to obtain the 1:β-Man structure, a $1_2$:β-Man structure was obtained (FIG. 8) that is consistent with the thermodynamic data and the 1D and 2D $^1H$ NMR spectra. Notably, noncovalent interactions between the second equivalent of 1 and OH$_4$ and OH$_3$ of β-Man are observed in the calculated structure, thereby explaining the high $\Delta H°$ of the second binding event. Also in the calculated $1_2$:β-Man structure, pyrrole protons of one molecule of 1 are within close proximity (<4.0 Å) to biphenyl protons $H^a$ and $H^b$ of the second molecule of 1, which is consistent with the experimentally observed NOEs between these atoms. In contrast, the $^1H$-$^1H$ ROESY of β-Glc and 1 under conditions that favor the 1:1 complex (20° C., 3.0 mM of 1, 1.0 mM of β-Glc) revealed that the axial protons on both faces of β-Glc have observable NOEs with the biphenyl base of 1 (FIG. 36), indicating that more than one binding geometry exists at equilibrium since 1 cannot interact with both faces of β-Glc simultaneously. Because the entropic penalty for the preorganization of 1:β-Glc has not been paid, it is speculated that the $\Delta S°$ associated with a second molecule of 1 binding to the 1:1 complex becomes prohibitively high, preventing the formation of a 2:1 complex. It should be noted that in the calculated structure of $1_2$:β-Man only three arms of each equivalent of 1 participate in binding to β-Man, so the fourth arms can be replaced in future receptors to increase function.

The structures of 1:β-Man and $1_2$:β-Man and the thermodynamic binding parameters explain the high selectivity of $K_3$ towards β-Man. The preference for β-Man over α-Man arises because the n-octyl chain of α-Man is perpendicular to the pyranoside ring, which interferes with a second association of 1. The preference of the second association event occurring for β-Man over other β-pyranosides because the observed $\Delta H°$ for the formation of 1:β-Man is nearly 4 kcal $mol^{-1}$ greater than the next highest 1:1 $\Delta H°$ (β-Glc), highlighting the dominant role of enthalpy in selectivity. Notably, the axial C2 hydroxyl group of mannosides is positioned to form two N—H⋯O bonds and one O—H⋯N bond with two secondary amines and one pyrrole of 1. Additional non-covalent interactions—such as a C—H⋯π interaction with $H^4$ and the aromatic ring and three N—H⋯O bonds between receptor 1 and the oxygens at C1 and C3 of β-Man—result in a tightly bound 1:β-Man complex, thus explaining why 1 exhibits cooperativity with mannosides and not its epimers such as galactosides or glucosides. Additionally, in the 1:β-Man geometry, a significant portion of the mannoside is exposed to solvent because one of the arms of 1 is orientated downwards underneath the n-octyl chain of β-Man, which provides a window for a second equivalent of 1 to bind. Because 1 is flexible, each equivalent of 1 that is bound to β-Man adopts a different conformation, so a 2:1 receptor: pyranoside complex is unlikely to form from a highly preorganized receptor.

Example 5

Implications of Competing Equilibria on the Selectivity of 1

Figures 9A, 9B:
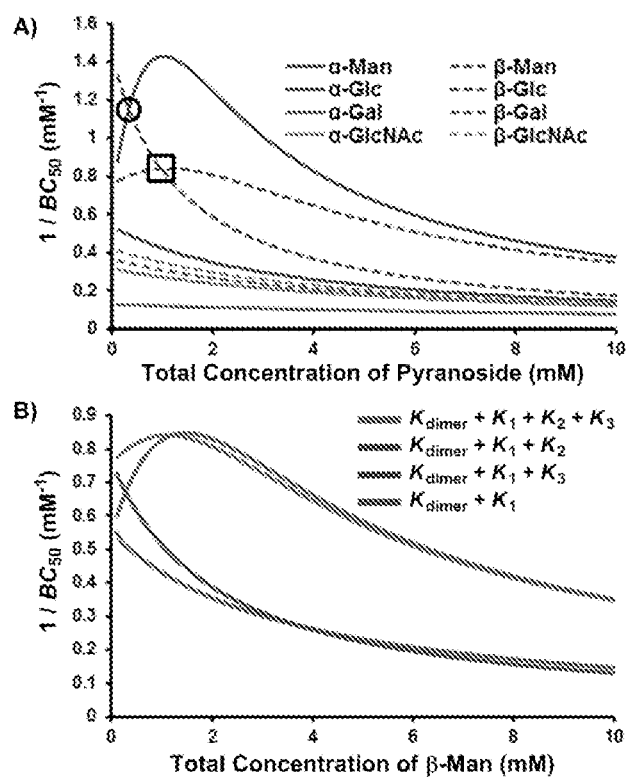
FIGS. 9A-9B show 1/BC$_{50}$ plots describing the pyranoside concentration dependence for the overall binding strength (1/BC$_{50}$) of receptor compound 1 toward each pyranoside, where higher values are indicative of stronger binding and crossover points, marked within a circle for β-Glc→α-Man and square for β-Glc→β-Man, denote changes in binding preference with increasing pyranoside concentration (FIG. 9A); and the influence of each positive cooperative binding equilibria ($K_2$ and $K_3$) on the BC$_{50}$ value of receptor 1 for β-Man (FIG. 9B).

In the presence of β-Man, the 1:1 complex, 1:β-Man, can either bind a second molecule of pyranoside, to form 1:β-Man$_2$ ($K_2$), or 1, to form $1_2$:β-Man ($K_3$). The outcome of these two competing processes is dependent on the concentrations of each substrate, with $K_2$ dominating at high concentrations of β-Man relative to 1, whereas $K_3$ is preferred the presence of excess 1. Thus, the numerous equilibria operating simultaneously in a solution of 1 and pyranoside ($K_{dimer}$, $K_1$, $K_2$ and $K_3$) and the concentration dependence of cooperative binding complicate the analysis of the overall selectivity of 1 for the eight pyranosides. To simplify the analysis of saccharide receptors that possess multiple binding pathways, the median binding concentration, $BC_{50}$, has previously been employed to describe binding strength (Nativi et al., *J. Am. Chem. Soc.* 129:4377-4385 (2007); Vacca et al., *J. Am. Chem. Soc.* 126:16456-16465 (2004), which are hereby incorporated by reference in their entirety). The $BC_{50}$ values of each of the pyranosides—defined as the total concentration of receptor 1 needed to bind 50% of the available pyranosides in solution—were computed over a pyranoside concentration range of 0 to 10.0 mM to probe both the magnitude and concentration dependence of the selectivity of 1 for the eight pyranosides (FIG. 9A). Note that all equilibria present in a receptor/pyranoside mixture contribute toward the calculated $BC_{50}$ value, and a higher $1/BC_{50}$ value is indicative of a higher overall binding strength.

The $1/BC_{50}$ plots reveal the effects of positive cooperativity on the binding affinity of 1 toward mannosides. Molecules with $K_2$ possess parabolic curves in the $1/BC_{50}$ plot. This is particularly evident in α-Man which possesses the highest affinity for 1 compared to all other pyranosides at a 0.8 mM pyranoside concentration. Interestingly, for β-Man, which exhibits cooperativity in both $K_2$ and $K_3$, a broader parabolic shape is observed, and little concentration dependence on the overall binding strength occurs between 0 and 4.0 mM of β-Man. When the calculated $1/BC_{50}$ plot is compared to a hypothetical plot in which only $K_1$ and $K_3$ are present, it was found that the presence of $K_3$ induces a substantial increase in selectivity at low concentrations (<1.5 mM) of β-Man (FIG. 9B). Alternatively, when a hypothetical plot is generated with only $K_1$ and $K_2$, $K_2$ enhanced selectivity when [β-Man] is greater than 1.0 mM, thus demonstrating the direct contribution of cooperative, complex equilibria on selectivity in saccharide receptors (FIG. 9B). Moreover, these plots confirm that pyranoside concentration controls which equilibrium, i.e. $K_2$ or $K_3$, prevails. At concentrations below 1.0 mM of β-Man, higher stoichiometry binding is achieved through $K_3$, while at greater β-Man concentrations, $K_2$ dominates.

As each $1/BC_{50}$ plot is a measure of affinity between 1 and pyranosides, comparing the plots of two or more pyranosides provides a means of assessing selectivity. Thus, the concentration of α-Man where the maximum $1/BC_{50}$ value is obtained (0.8 mM) is also where the maximum selectivity occurs for α-Man relative to the other pyranosides. Beyond this value, the selectivities gradually approach 2:1 mannoside:pyranoside, which is a consequence of the differences in binding stoichiometry—receptor 1 can accommodate two molecules of mannosides and only binds 1:1 for the other pyranosides. Importantly, crossover points in the $BC_{50}$ plots are observed between β-Glc and the mannosides (FIG. 9A), meaning that the selectivity of 1 changes as a function of pyranoside concentration. At low pyranoside concentrations (<0.3 mM), receptor 1 binds β-Glc with the highest affinity owing to its high value of $K_1$, which effectively competes with the cooperative binding of 1 toward mannosides. From 0.3 mM to 1.0 mM, the binding order for 1 is α-Man>β-Glc>β-Man. At higher pyranoside concentrations (>1.0 mM), the binding order for 1 changes to α-Man>β-Man>β-Glc as a result of the 2:1 binding stoichiometry that occurs only with mannosides. Consequently, a new concentration dependence has been discovered that governs the stoichiometry of the resulting complex and the pyranoside preference of the receptor.

While $1/BC_{50}$ plots describe the concentration dependent affinity of 1 for different pyranosides, a standardized metric describing the binding ability of receptors exhibiting multiple equilibria, the intrinsic median binding concentration, $BC_{50}^0$, has been employed by others. $BC_{50}^0$ is calculated by the integration of the inverse $BC_{50}$ function versus the molar fraction of bound receptor, $\chi_H$ (Nativi et al., *Chem. Eur. J.* 17:4814-4820 (2011), which is hereby incorporated by reference in its entirety):

$$1/BC_{50}^0 = 2\int_{\chi_H=0}^{\chi_H=1} 1/BC_{50}(\chi_H)d\chi_H \qquad (17)$$

The $BC_{50}^0$ values of the pyranosides for receptor 1 were determined using Eq. 17. For the mannose-selective synthetic lectins developed by the Roelens group, the reported $BC_{50}^0$ values range from 13.5 mM to 83 μM, with the latter corresponding to an outstanding chiral diaminopyrrolitic receptor for β-Man in acetonitrile (Nativi et al., *Chem. Eur. J.* 17:4814-4820 (2011), which is hereby incorporated by reference in its entirety). For receptor 1, the two pyranosides that exhibit positive cooperativity, α-Man and β-Man, have lower $BC_{50}^0$ values of 460 and 730 μM, respectively, than were observed for the other pyranosides, where $BC_{50}^0$ values range from 1860 to 7740 μM, except for β-Glc($BC_{50}^0$=700 μM). The ratio of $BC_{50}^0$ values has been used to compare the selectivities of carbohydrate receptors for mannosides (Nativi et al., *Chem. Eur. J.* 17:4814-4820 (2011), which is hereby incorporated by reference in its entirety) and range from excellent (16.8:1 for α-Man:α-Gal) to modest (1.5:1 for α-Man:β-Glc) for 1. However, because of the concentration dependent switching of selectivities, $BC_{50}^0$ does not fully reflect the binding behavior of 1 because they suggest that 1 binds β-Glc preferentially over β-Man rather than reflect the subtleties of concentration dependent selectivity.

Discussion of Examples 1-5

Flexible supramolecular host 1 was developed to examine how the ability to rearrange and dynamically sample conformational and thermodynamic space could reveal new modes for carbohydrate recognition. The association between 1 and eight octylpyranosides was studied by variable temperature 1H NMR titrations to determine $K_a$s, and Van't Hoff analyses were performed to derive the thermodynamic parameters for each association event. These studies revealed that 1, which possesses four aminopyrrolitic arms and aromatic rings forms N—H···O, O—H···N, and C—H···π interactions with pyranoside guests, resulting in 1:1 host:guest complexes with similar affinities for all eight pyranosides. Upon altering the host:guest ratio beyond 1:1, new equilibria emerge that lead to the formation of 1:2 and 2:1 receptor:pyranoside complexes exclusively with mannosides at 25° C. The geometries of these complexes were determined by 1D and 2D $^1$H NMR spectroscopy and molecular modeling to reveal a $C_2$-symmetric structure for $1:\beta$-Man$_2$ and a cage structure for $1_2:\beta$-Man that were consistent with all data sets. Importantly, the structure of $1_2:\beta$-Man indicates that only three of the four aminopyrrolitic arms are involved in binding, suggesting that the fourth arm could be replaced to increase the functionality of future receptors and enhance binding in competitive solvents.

Mannosides are important targets, because they are both diagnostic and prognostic for several cancers (de Leoz et al., *Mol. Cell. Proteomics* 10:M110.002717 (2011); Ann et al., *Curr. Opin. Chem. Biol.* 13:601-607 (2009), which are hereby incorporated by reference in their entirety), and receptors that target mannosides could be used for detection and delivery, so developing synthetic carbohydrate receptors remains a major area of research. An analysis of the binding constants for the first and second association events for 1:β-Man$_2$ (K$_1$ and K$_2$) and 1$_2$:β-Man (K$_1$ and K$_3$) indicates that the binding is cooperative—that the first association event facilitates the second. The selectivity of 1 for mannosides arises as a direct result of the preorganization of the 1:1 complex. The flexible receptor 1 achieves selectivity between pyranosides that may differ only by the orientation of a single hydroxyl group, despite the entropic penalty that must be paid to organize the complexes. In fact, the lack of preorganization in the strong 1:β-Glc complex precludes the formation of a stable 1$_2$:β-Glc structure, so entropy actually determines selectivity. Although receptor 1 does not achieve the same overall affinity as the best rigidly preorganized mannose-specific receptors, the selectivity is comparable despite the differences in binding mechanisms, thus confirming the hypothesis that increasing the receptor dynamics reveals new binding geometries because of the ability of flexible hosts to dynamically explore conformational space.

Finally, it should be noted that synthetic carbohydrate receptors can provide insight into the subtleties of natural lectin-carbohydrate interactions and reveal how carbohydrate recognition conveys complex information in biological networks. Eukaryotic cell surfaces are coated with a carbohydrate layer, the glycocalyx, where the multivalent presentation of carbohydrates on a cell surface enhances binding affinity, a phenomenon termed the cluster glycoside effect (Lundquist & Toone, *Chem. Rev.* 102:555-578 (2002), which is hereby incorporated by reference in its entirety). Interestingly, the selectivity of 1 changes with pyranoside concentration, where 1 preferentially binds glycosides at low concentration (<0.3 mM) and mannosides at concentrations representative of glycoside clusters. While concentration dependent selectivity may be unprecedented with synthetic carbohydrate receptors, multivalency and cooperativity are ubiquitous in biology, so concentration dependent switching may commonly occur with natural lectins which could have implications for hierarchical organization and information transfer in biological networks.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound of Formula I:

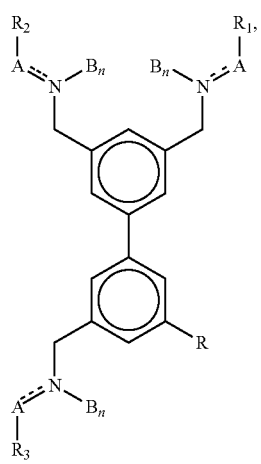

(I)

R is a moiety of Formula II

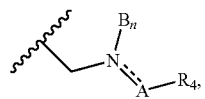

(II)

or a moiety of Formula III

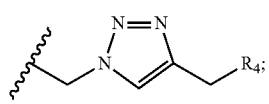

(III)

----- is a single or a double bond;

A is selected from the group consisting of: (1) —CH$_2$—; (2) —C(O)—; and 3) =CH—;

B is H, and n is 0 or 1;

each of R$_1$, R$_2$, R$_3$, and R$_4$ is a heterocycle or a heteroaryl containing 1-5 heteroatoms selected from the group consisting of nitrogen, sulfur, and oxygen, wherein R$_1$, R$_2$, R$_3$, and R$_4$ can be the same or different;

R$_1$, R$_2$, R$_3$, and R$_4$ can be optionally substituted 1 to 4 times with substituents selected from the group consisting of halogen, C$_{1-6}$ alkyl, C$_{2-6}$ alkenyl, C$_{2-6}$ alkynyl, C$_{3-6}$ cycloalkyl, aryl, —OR$_5$, —CN, —NO$_2$, —NR$_5$R$_6$, —COOR$_5$, —COR$_5$, —CONHR$_5$, and —CN;

and each of R$_5$ and R$_6$ is independently H or C$_{1-6}$ alkyl.

2. A compound according to claim 1, wherein one or more of R$_1$, R$_2$, R$_3$, and R$_4$ is a substituted or unsubstituted heteroaromatic ring selected from the group of pyridine, pyrazine, pyrimidine, pyridazine, imidazole, pyrrole, oxazole, isoxazole, triazine, thiazole, isothiazole, indazole, purine, quinoline, isoquinoline, quinoxaline, quinazoline, cinnoline, acridine, benzoxazole, benzisoxazole, benzothiazole, thiophene, furan, benzofuran, benzothiophene, and oxadiazole.

3. The compound according to claim 1, wherein R is a moiety of Formula II

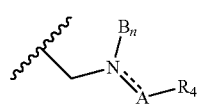

(II)

or Formula III

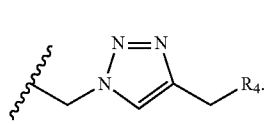

(III)

4. The compound of claim 1 having a structure of Formula IA

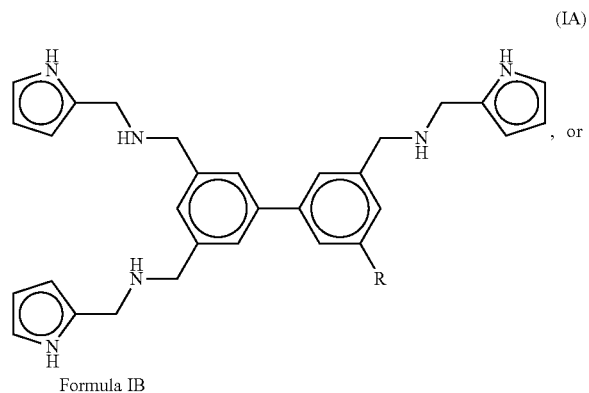

Formula IB

5. A pharmaceutical formulation comprising:
   a compound according to claim 1 and
   a pharmaceutically acceptable carrier.
6. A pharmaceutical delivery vehicle comprising:
   a compound according to claim 1 coupled to a pharmaceutically active moiety and
   a pharmaceutically acceptable carrier.
7. A method of detecting a carbohydrate in a sample, said method comprising:
   providing a compound according to claim 1;
   contacting the sample with the compound under conditions effective for binding to occur between the compound and the carbohydrate; and
   detecting any binding between the compound and the carbohydrate, if present, in the sample.
8. The method according to claim 7, wherein the carbohydrate is a pyranoside.
9. The method according to claim 8, wherein the pyranoside is mannose.
10. The method according to claim 7 further comprising:
    quantifying the carbohydrate present in the sample based on said detecting.
11. A method of diagnosing, in a subject, a condition selected from the group consisting of cancer, inflammatory disease, cardiovascular disease, and an infectious disease, said method comprising:
    obtaining a sample from the subject;
    providing a compound according to claim 1;
    contacting the sample with the compound under conditions effective for binding to occur between the compound and the carbohydrate, if present, in the sample;
    detecting any binding between the compound and the carbohydrate; and
    diagnosing the condition in the subject based on said detecting.
12. The method according to claim 11, wherein the carbohydrate is mannose.
13. The method according to claim 11 further comprising:
    quantifying the carbohydrate present in the sample based on said detecting, wherein said diagnosing is based on said quantifying.
14. A method of treating or preventing in a subject a condition mediated by a carbohydrate selected from the group consisting of cancer, inflammatory disease, cardiovascular disease, and an infectious disease said method comprising:
    selecting a subject having a carbohydrate-mediated condition and
    administering to the selected subject a compound of claim 1, under conditions effective for the compound to bind to the carbohydrate.
15. The method according to claim 14, wherein the carbohydrate is a mannose.

* * * * *